(12) United States Patent
Strober et al.

(10) Patent No.: US 9,072,716 B2
(45) Date of Patent: Jul. 7, 2015

(54) METHODS OF TREATING AND PREVENTING INFLAMMATORY BOWEL DISEASE INVOLVING IL-13 AND NKT CELLS

(75) Inventors: Warren Strober, Bethesda, MD (US); Ivan Fuss, Kensington, MD (US); Peter Mannon, Chevey Chase, MD (US); Jan Preiss, Berlin (DE); Raj Puri, Potomac, MD (US); Koji Kawakami, Kyoto (JP); Stefan Fichtner-Feigl, Bethesda, MD (US); Atsushi Kitani, Rockville, MD (US)

(73) Assignee: The United States of America, as represented by the Secretary Department of Health by Human Servies, Washington, DC (US)

( * ) Notice: Subject to any disclaimer, the term of this patent is extended or adjusted under 35 U.S.C. 154(b) by 1328 days.

(21) Appl. No.: 11/918,711

(22) PCT Filed: Apr. 14, 2006

(86) PCT No.: PCT/US2006/014393
§ 371 (c)(1),
(2), (4) Date: Nov. 10, 2008

(87) PCT Pub. No.: WO2006/113614
PCT Pub. Date: Oct. 26, 2006

(65) Prior Publication Data
US 2009/0092543 A1    Apr. 9, 2009

Related U.S. Application Data

(60) Provisional application No. 60/671,624, filed on Apr. 15, 2005.

(51) Int. Cl.
*A61K 51/08* (2006.01)
*A61K 38/20* (2006.01)
*A61K 31/00* (2006.01)
*A61K 38/16* (2006.01)
*C07K 14/54* (2006.01)

(52) U.S. Cl.
CPC ............ *A61K 38/2086* (2013.01); *A61K 31/00* (2013.01); *A61K 38/164* (2013.01); *C07K 14/5437* (2013.01)

(58) Field of Classification Search
None
See application file for complete search history.

(56) References Cited

U.S. PATENT DOCUMENTS

| | | | | |
|---|---|---|---|---|
| 5,614,191 | A | * 3/1997 | Puri et al. | 424/178.1 |
| 6,143,871 | A | 11/2000 | Bonnefoy et al. | |
| 6,296,843 | B1 | * 10/2001 | Debinski | 424/85.2 |
| 6,518,061 | B1 | 2/2003 | Puri et al. | |
| 7,598,058 | B2 | 10/2009 | Debinski et al. | |
| 2002/0042387 | A1 | 4/2002 | Raz et al. | |
| 2004/0043921 | A1 | 3/2004 | Bonnefoy et al. | |

FOREIGN PATENT DOCUMENTS

| | | |
|---|---|---|
| AU | 2002315115 | 6/2002 |
| AU | 2002315115 | 1/2009 |
| CA | 2489540 | 6/2002 |
| EP | 02742057.9 | 6/2002 |
| EP | 06750435.7 | 4/2006 |
| GB | 2403952 | 1/2005 |
| HK | 05112119.6 | 12/2005 |
| JP | 2004-515561 | 6/2002 |
| NZ | 537726 | 6/2002 |
| WO | WO 00/02583 | 1/2000 |
| WO | WO 00/02923 | 1/2000 |
| WO | PCT/US02/18790 | 6/2002 |
| WO | WO-03/080675 | 10/2003 |
| WO | WO2004001655 | * 12/2003 |
| WO | WO-2005/121177 | 12/2005 |
| WO | WO-2006/003407 | 1/2006 |
| WO | PCT/US06/014393 | 4/2006 |
| WO | WO-02/18422 | 3/2007 |
| WO | PCT/US2006/014393 | 4/2007 |
| ZA | 2005/0375 | 6/2002 |
| ZA | 2005/0375 | 8/2006 |

OTHER PUBLICATIONS

Thompson et al. (J. Biol. Chem. 1999, 274:29944-29950).*
Wang, Journal of Drug Targeting, 1996, vol. 4, No. 4, pp. 195-232.*
Blanchard et al., J Immunol 2004; 172:3775-3783.*
Heller et al., Gastroenterology. Aug. 2005;129(2):550-64.*
Park et al., Int. J. Cancer: 114, 80-87 (2005).*
Shaoul et al., Journal of Pediatric Gastroenterology and Nutrition 38:488-493, May 2004.*
U.S. Appl. No. 10/517,898, filed Jun. 14, 2002, Strober.
Balk, S. P., Bleicher, P. A., and Terhorst, C. (1989). Isolation and characterization of a cDNA and gene coding for a fourth CD1 molecule. Proc Natl Acad Sci U S A 86, 252-256.
Bendelac, A. (1995). Positive selection of mouse NK1+ T cells by CD1-expressing cortical thymocytes. J Exp Med 182, 2091-2096.
Bleicher, P. A., Balk, S. P., Hagen, S. J., Blumberg, R. S., Flotte, T. J., and Terhorst, C. (1990). Expression of murine CD1 on gastrointestinal epithelium. Science 250, 679-682.
Blumberg, R. S., Terhorst, C., Bleicher, P., McDermott, F. V., Allan, C. H., Landau, S. B., Trier, J. S., and Balk, S. P. (1991). Expression of a nonpolymorphic MHC class I-like molecule, CD1D, by human intestinal epithelial cells. J Immunol 147, 2518-2524.
Boirivant, M., Fuss, I. J., Chu, A., and Strober, W. (1998). Oxazolone colitis: A murine model of T helper cell type 2 colitis treatable with antibodies to interleukin 4. J Exp Med 188, 1929-1939.

(Continued)

*Primary Examiner* — Zachary Skelding
(74) *Attorney, Agent, or Firm* — Locke Lord LLP; Bryan D. Zerhusen; Gabriel J. McCool

(57) ABSTRACT

The present invention provides a method of treating or preventing the inflammatory response of ulcerative colitis or Crohn's disease in a subject comprising administering to the subject an effective amount of a substance that inhibits the binding of IL-13 to IL-13 receptors on NKT cells or delivers an effector molecule to the NKT cells.

10 Claims, 20 Drawing Sheets

(56) References Cited

OTHER PUBLICATIONS

Bonish B, Jullien D, Dutronc Y, Huang BB, Modlin R, Spada FM, Porcelli SA, Nickoloff BJ. Overexpression of CD1d by keratinocytes in psoriasis and CD1d-dependent IFN-gamma production by NK-T cells. J Immunol. Oct. 1, 2000;165(7):4076-85.

Brown, KD, Zurawski SM, Mosmann TR, Zurawski G. A family of small inducible proteins secreted by leukocytes are members of a new superfamily that includes leukocyte and fibroblast-derived inflammatory agents, growth factors, and indicators of various activation processes J. Immunol. 142 (2), 679-687 (1989).

Brown, M. A., and Hural, J. (1997). Functions of IL-4 and control of its expression. Crit Rev Immunol 17, 1-32.

Brown, TE, Bankhurst AD, Strickland RG. Natural killer cell function and lymphocyte subpopulation profiles in inflammatory bowel disease. J Clin Lab Immunol. Jul. 1983;11(3):113-7.

Camoglio L, Te Velde AA, Tigges AJ, Das PK, Van Deventer SJ. Altered expression of interferon-gamma and interleukin-4 in inflammatory bowel disease. Inflamm Bowel Dis. Nov. 1998;4(4):285-90.

Ceponis, P. J., Botelho, F., Richards, C. D., and McKay, D. M. (2000). Interleukins 4 and 13 increase intestinal epithelial permeability by a phosphatidylinositol 3-kinase pathway. Lack of evidence for STAT 6 involvement. J Biol Chem 275, 29132-29137.

Chen, H., and Paul, W. E. (1997). Cultured NK1.1+ CD4+ T cells produce large amounts of IL-4 and IFN- gamma upon activation by anti-CD3 or CD1. J Immunol 159, 2240-2249.

Cui, J., Shin, T., Kawano, T., Sato, H., Kondo, E., Toura, I., Kaneko, Y., Koseki, H., Kanno, M., and Taniguchi, M. (1997). Requirement for Valpha14 NKT cells in IL-12-mediated rejection of tumors. Science 278, 1623-1626.

del Mar Cabrera M, Valle J, Pajares JM, Romero I, Zomeno M, Mate J. Expression of the Kp43 (CD 94) receptor by natural killer (NK) cells in ulcerative colitis. Hepatogastroenterology. Sep.-Oct. 2001;48(41):1316-20.

Desreumaux P, Brandt E, Gambiez L, Emilie D, Geboes K, Klein O, Ectors N, Cortot A, Capron M, Colombel JF. Distinct cytokine patterns in early and chronic ileal lesions of Crohn's disease. Gastroenterology. Jul. 1997;113(1):118-26.

Dolganov, et al. "Coexpression of the interleukin-13 and interleukin-4 genes correlates with their physical linkage in the cytokine gene cluster on human chromosome 5q23-31" *Blood* 87 (8), 3316-3326 (1996).

Donaldson, D. D., Whitters, M. J., Fitz, L. J., Neben, T. Y., Finnerty, H., Henderson, S. L., O'Hara, R. M., Jr., Beier, D. R., Turner, K. J., Wood, C. R., and Collins, M. (1998). The murine IL-13 receptor alpha 2: molecular cloning, characterization, and comparison with murine IL-13 receptor alpha 1. J Immunol 161, 2317-2324.

Fiocchi C, Tubbs RR, Youngman KR. Human intestinal mucosal mononuclear cells exhibit lymphokine-activated killer cell activity. Gastroenterology. Mar. 1985;88(3):625-37.

Fiorentino, D. F., Ziotnik, A., Vieira, P., Mosmann, T. R., Howard, M., Moore, K. W., and O'Garra, A. (1991). IL-10 acts on the antigen-presenting cell to inhibit cytokine production by Th1 cells. J Immunol 146, 3444-3451.

Fort, M. M., Cheung, J., Yen, D., Li, J., Zurawski, S. M., Lo, S., Menon, S., Clifford, T., Hunte, B., Lesley, R., et al. (2001). IL-25 induces IL-4, IL-5, and IL-13 and Th2-associated pathologies in vivo. Immunity 15, 985-995.

Fuss, I. J., Neurath, M., Boirivant, M., Klein, J. S., de la Motte, C., Strong, S. A., Fiocchi, C., and Strober, W. (1996). Disparate CD4+ lamina propria (LP) lymphokine secretion profiles in inflammatory bowel disease. Crohn's disease LP cells manifest increased secretion of IFN-gamma, whereas ulcerative colitis LP cells manifest increased secretion of IL-5. J Immunol 157, 1261-1270.

Ginsburg CH, Dambrauskas JT, Ault KA, Falchuk ZM. Impaired natural killer cell activity in patients with inflammatory bowel disease: evidence for a qualitative defect. Gastroenterology. Oct. 1983;85(4):846-51.

Gumperz, J. E., Roy, C., Makowska, A., Lum, D., Sugita, M., Podrebarac, T., Koezuka, Y., Porcelli, S. A., Cardell, S., Brenner, M. B., and Behar, S. M. (2000). Murine CD1d-restricted T cell recognition of cellular lipids. Immunity 12, 211-221.

Hayakawa, K., Lin, B. T., and Hardy, R. R. (1992). Murine thymic CD4+ T cell subsets: a subset (Thy0) that secretes diverse cytokines and overexpresses the V beta 8 T cell receptor gene family. J Exp Med 176, 269-274.

Inoue S, Matsumoto T, Iida M, Mizuno M, Kuroki F, Hoshika K, Shimizu M. Characterization of cytokine expression in the rectal mucosa of ulcerative colitis: correlation with disease activity. Am J Gastroenterol. Sep. 1999;94(9):2441-6.

Ishikawa, H., Hisaeda, H., Taniguchi, M., Nakayama, T., Sakai, T., Maekawa, Y., Nakano, Y., Zhang, M., Zhang, T., Nishitani, M., et al. (2000). CD4(+) v(alpha)14 NKT cells play a crucial role in an early stage of protective immunity against infection with Leishmania major. Int Immunol 12, 1267-1274.

Kadivar K, Defelice ML, Markowitz JE, Baldassano RN, Brown KA. Intestinal interleukin-13 in pediatric inflammatory bowel disease patients. [abstract]. J. Pediatr Gastroenterol Nutr. 2001 33(3):372.

Kaneko, Y., Harada, M., Kawano, T., Yamashita, M., Shibata, Y., Gejyo, F., Nakayama, T., and Taniguchi, M. (2000). Augmentation of Valpha14 NKT cell-mediated cytotoxicity by interleukin 4 in an autocrine mechanism resulting in the development of concanavalin A-induced hepatitis. J Exp Med 191, 105-114.

Kawano, T., Cui, J., Koezuka, Y., Toura, I., Kaneko, Y., Motoki, K., Ueno, H., Nakagawa, R., Sato, H., Kondo, E., et al. (1997). CD1d-restricted and TCR-mediated activation of valpha14 NKT cells by glycosylceramides. Science 278, 1626-1629.

Koyasu, S. (1994). CD3+CD16+NK1.1+B220+ large granular lymphocytes arise from both alpha-beta TCR+CD4-CD8- and gamma-delta TCR+CD4-CD8- cells. J Exp Med 179, 1957-1972.

Kucharzik T, Lugering N, Adolf M, Domschke W, Stoll R. Synergistic effect of immunoregulatory cytokines on peripheral blood monocytes from patients with inflammatory bowel disease. Dig Dis Sci. Apr. 1997;42(4):805-12.

Kumar, H., Belperron, A., Barthold, S. W., and Bockenstedt, L. K. (2000). Cutting edge: CD1d deficiency impairs murine host defense against the spirochete, *Borrelia burgdorferi*. J Immunol 165, 4797-4801.

Lakatos L. Immunology of inflammatory bowel diseases. Acta Physiol Hung. 2000;87(4):355-72.

Lantz, O., and Bendelac, A. (1994). An invariant T cell receptor alpha chain is used by a unique subset of major histocompatibility complex class I-specific CD4+ and CD4-8- T cells in mice and humans. J Exp Med 180, 1097-1106.

Lee, P. T., Benlagha, K., Teyton, L., and Bendelac, A. (2002). Distinct functional lineages of human V(alpha)24 natural killer T cells. J Exp Med 195, 637-641.

Lugering N, Kucharzik T, Stein H, Winde G, Lugering A, Hasilik A, Domschke W, Stoll R. IL-10 synergizes with IL-4 and IL-13 in inhibiting lysosomal enzyme secretion by human monocytes and lamina propria mononuclear cells from patients with inflammatory bowel disease. Dig Dis Sci. Apr. 1998;43(4):706-14.

Mack DR, Beedle S, Warren J, Davis J, Gross T. Peripheral blood intracellular cytokine analysis in children newly diagnosed with inflammatory bowel disease. Pediatr Res. Mar. 2002;51(3):328-32.

Manzano L, Alvarez-Mon M, Abreu L, Antonio Vargas J, de la Morena E, Corugedo F, Durantez A. Functional impairment of natural killer cells in active ulcerative colitis: reversion of the defective natural killer activity by interleukin 2. Gut. Feb. 1992;33(2):246-51.

Minty, A., Asselin, S., Bensussan, A., Shire, D., Vita, N., Vyakarnam, A., Wijdenes, J., Ferrara, P., and Caput, D. (1997). The related cytokines interleukin-13 and interleukin-4 are distinguished by differential production and differential effects on T lymphocytes. Eur Cytokine Netw 8, 203-213.

Miyamoto, K., Miyake, S., and Yamamura, T. (2001). A synthetic glycolipid prevents autoimmune encephalomyelitis by inducing TH2 bias of natural killer T cells. Nature 413, 531-534.

Mizoguchi, A., Mizoguchi, E., and Bhan, A. K. (1999). The critical role of interleukin 4 but not interferon gamma in the pathogenesis of colitis in T-cell receptor alpha mutant mice. Gastroenterology 116, 320-326.

(56) References Cited

OTHER PUBLICATIONS

Moore, K. W., O'Garra, A., de Waal Malefyt, R., Vieira, P., and Mosmann, T. R. (1993). Interleukin-10. Annu Rev Immunol 11, 165-190.

Neurath, M. F., Fuss, I., Kelsall, B. L., Stuber, E., and Strober, W. (1995). Antibodies to interleukin 12 abrogate established experimental colitis in mice. J Exp Med 182, 1281-1290.

Park, S. H., Roark, J. H., and Bendelac, A. (1998). Tissue-specific recognition of mouse CD1 molecules. J Immunol 160, 3128-3134.

Parronchi, P., Romagnani, P., Annunziato, F., Sampognaro, S., Becchio, A., Giannarini, L., Maggi, E., Pupilli, C., Tonelli, F., and Romagnani, S. (1997). Type 1 T-helper cell predominance and interleukin-12 expression in the gut of patients with Crohn's disease. Am J Pathol 150, 823-832.

Radford-Smith G, Jewell DP. Cytokines and inflammatory bowel disease. Baillieres Clin Gastroenterol. Mar. 1996;10(1):151-64.

Roark, J. H., Park, S. H., Jayawardena, J., Kavita, U., Shannon, M., and Bendelac, A. (1998). CD1.1 expression by mouse antigen-presenting cells and marginal zone B cells. J Immunol 160, 3121-3127.

Rogler G, Andus T. Cytokines in inflammatory bowel disease. World J Surg. Apr. 1998;22(4):382-9.

Sartor, R. B. (1995). Current concepts of the etiology and pathogenesis of ulcerative colitis and Crohn's disease. Gastroenterol Clin North Am 24, 475-507.

Saubermann LJ, Beck P, De Jong YP, Pitman RS, Ryan MS, Kim HS, Exley M, Snapper S, Balk SP, Hagen SJ, Kanauchi O, Motoki K, Sakai T, Terhorst C, Koezuka Y, Podolsky DK, Blumberg RS. Activation of natural killer T cells by alpha-galactosylceramide in the presence of CD1d provides protection against colitis in mice. Gastroenterology. Jul. 2000;119(1):119-28.

Scheiffele, F., Fuss, I. (2002). Induction of TNBS colitis in mice, vol. 15.19, John Wiley & Sons, Inc.).

Shinoda M, Haruta J, Tanimoto M, Ando T, Hosokawa T, Ina K, Kusugami K. Lamina propria mononuclear cells express and respond to interleukin-2 differently in Crohn's disease and ulcerative colitis. Intern Med. Sep. 1996;35(9):679-85.

Singh B, Powrie F, Mortensen NJ. Immune therapy in inflammatory bowel disease and models of colitis. Br J Surg. Dec. 2001;88(12):1558-69.

Smiley, S. T., Kaplan, M. H., and Grusby, M. J. (1997). Immunoglobulin E production in the absence of interleukin-4-secreting CD1-dependent cells. Science 275, 977-979.

Sonoda, K. H., Exley, M., Snapper, S., Balk, S. P., and Stein-Streilein, J. (1999). CD1-reactive natural killer T cells are required for development of systemic tolerance through an immune-privileged site. J Exp Med 190, 1215-1226.

Spada, F. M., Koezuka, Y., and Porcelli, S. A. (1998). CD1d-restricted recognition of synthetic glycolipid antigens by human natural killer T cells. J Exp Med 188, 1529-1534.

Strober W, Fuss IJ, Blumberg RS. The immunology of mucosal models of Inflammation. Annu Rev Immunol. 2002;20:495-549. Epub Oct. 4, 2001.

Strober, S., Cheng, L., Zeng, D., Palathumpat, R., Dejbakhsh-Jones, S., Huie, P., and Sibley, R. (1996). Double negative (CD4-CD8- alpha beta+) T cells which promote tolerance induction and regulate autoimmunity. Immunol Rev 149, 217-230.

Takeda, K., Hayakawa, Y., Van Kaer, L., Matsuda, H., Yagita, H., and Okumura, K. (2000). Critical contribution of liver natural killer T cells to a murine model of hepatitis. Proc Natl Acad Sci U S A 97, 5498-5503.

Tamura J, Jinbo T, Itoh K, Take H, Matsushima T, Murakami H, Kubota K, Tsuchiya J, Naruse T. Suppressed natural killer cell activity in ulcerative colitis. J Med. 1994;25(5):337-40.

Terabe, M., Matsui, S., Noben-Trauth, N., Chen, H., Watson, C., Donaldson, D. D., Carbone, D. P., Paul, W. E., and Berzofsky, J. A. (2000). NKT cell-mediated repression of tumor immunosurveillance by IL-13 and the IL-4R-STAT6 pathway. Nat Immunol 1, 515-520.

Urban, J. F., Jr., Noben-Trauth, N., Donaldson, D. D., Madden, K. B., Morris, S. C., Collins, M., and Finkelman, F. D. (1998). IL-13, IL-4Ralpha, and Stat6 are required for the expulsion of the gastrointestinal nematode parasite *Nippostrongylus brasiliensis*. Immunity 8, 255-264.

Vainer B, Nielsen OH, Hendel J, Horn T, Kirman I. Colonic expression and synthesis of interleukin 13 and interleukin 15 in inflammatory bowel disease. Cytokine. Oct. 2000;12(10):1531-6.

van Tol EA, Verspaget HW, Pena AS, Lamers CB. Normal inflammatory bowel disease mucosa conceals alterations in natural killer cell activity. Scand J Gastroenterol. Dec. 1992;27(12):999-1005.

Vezys, V., Olson, S., and Lefrancois, L. (2000). Expression of intestine-specific antigen reveals novel pathways of CD8 T cell tolerance induction. Immunity 12, 505-514.

Wills-Karp, M., Luyimbazi, J., Xu, X., Schofield, B., Neben, T. Y., Karp, C. L., and Donaldson, D. D. (1998). Interleukin-13: central mediator of allergic asthma. Science 282, 2258-2261.

Yoshimoto, T., and Paul, W. E. (1994). CD4pos, NK1.1pos T cells promptly produce interleukin 4 in response to in vivo challenge with anti-CD3. J Exp Med 179, 1285-1295.

Zurawski, G., and deVries, J. E. (1994). Interleukin 13, an interleukin 4-like cytokine that acts on monocytes and B cells, but not on T cells. Immunol Today 15, 19-26.

Mintz et al., "Molecular targeting with recombinant cytotoxins of interleukin-13 receptor α2-expressing glioma," Journal of Neuro-Oncology, 64: 117-123, 2003.

Husain et al., "Interleukin-13 receptor-directed cytotoxin for malignant glioma therapy: from bench to bedside," Journal of Neuro-Oncology, 65: 37-48, 2003.

Communication pursuant to Article 94(3) EPC in EP 06 750 435.7, issued Dec. 14, 2010.

Mintz, Akiva et al., Molecular targeting with recombinant cytotoxins of Interleukin-13 receptor α2-expressing glioma, Journal of Neuro-Oncology; vol. 64, pp. 117-123 (2003).

Husain, Syed R., Interleukin-13 receptor-directed cytotoxin for malignant glioma therapy: from bench to bedside, Journal of Neuro-Oncology, vol. 65, pp. 37-48 (2003).

Fuss et al., "Nonclassical CD1d-restricted NK T cells that produce IL-13 characterize an atypical Th2 response in ulcerative colitis," J. Clin. Invest. 113:1491497 (2004).

Heller et al., "Oxazolone Colitis, a Th2 Colitis Model Resembling Ulcerative Colitis, Is Mediated by IL-13-Producing NK-T Cells," Immunity, vol. 17, 629-638 (2002).

Kioi et al., "Mechanism of action of interleukin-13 antagonist (IL-13E13K) in cells expressing various types of IL-4R," Cellular Immunology, vol. 229, No. 1, 41-51 (2004).

Oshima et al., "Characterization of a Powerful High Affinity Antagonist That Inhibits Biological Activities of Human Interleukin-13," Jnl. of Biological Chemistry, vol. 276, No. 18, 15185-15191 (2001).

Podolsky, "Inflammatory Bowel Disease," N Eng J Med, vol. 347, No. 6, 417-429 (2002).

Spencer et al., "Neutralizing IL-4 or IL-13 alters mucosal immunity in late phase colitis of IL-10/-mice," FASEB Journal, vol. 17, No. 7, C30 92003) & AAI Meeting Abstracts (2003).

* cited by examiner

Fig. 5
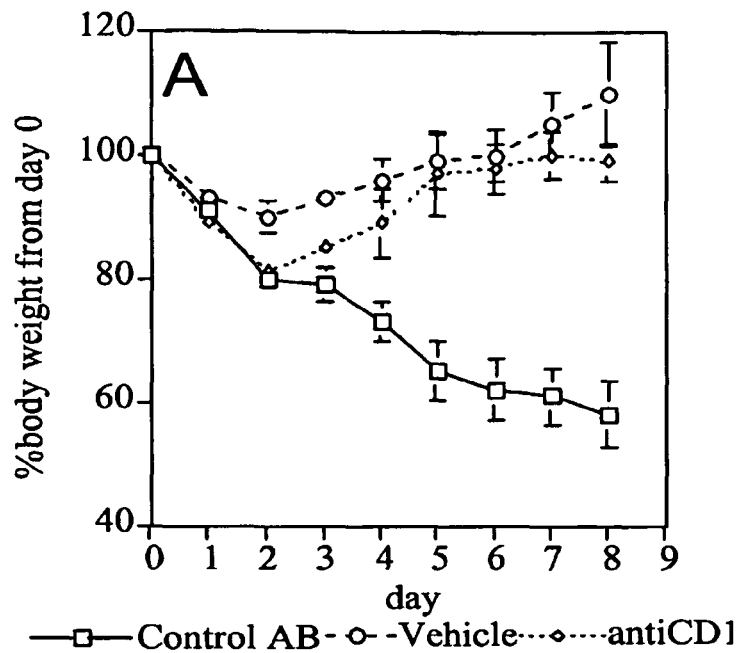
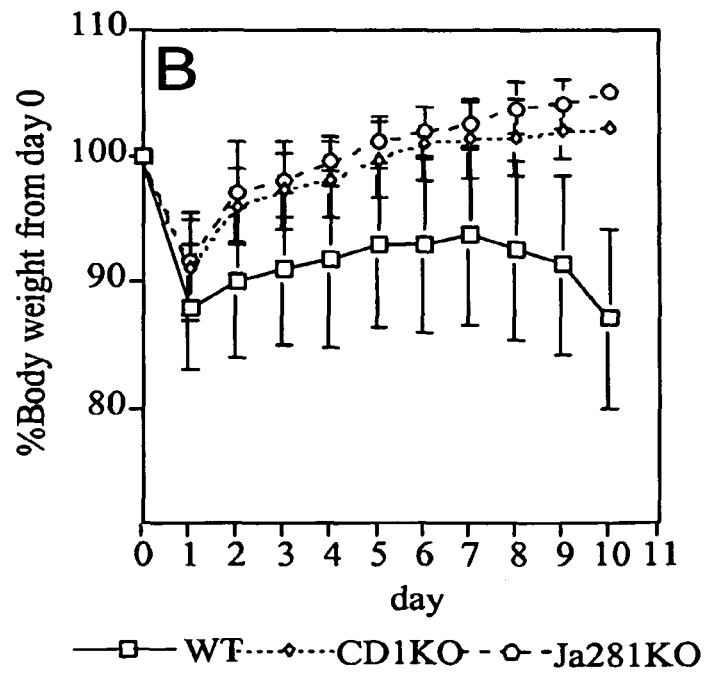

Fig. 6
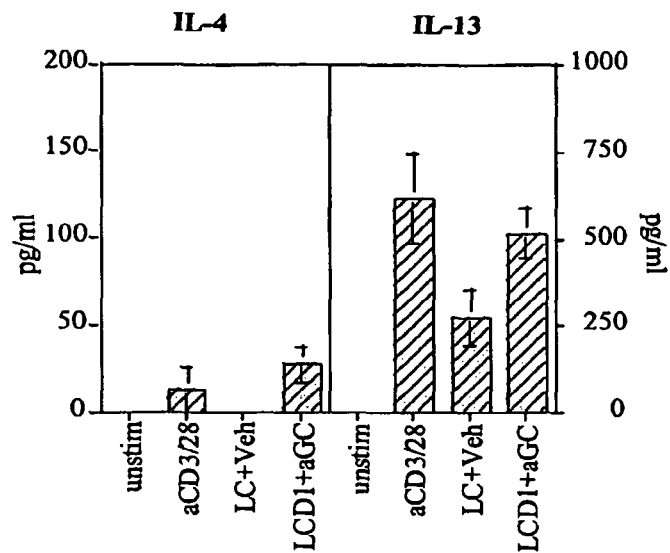
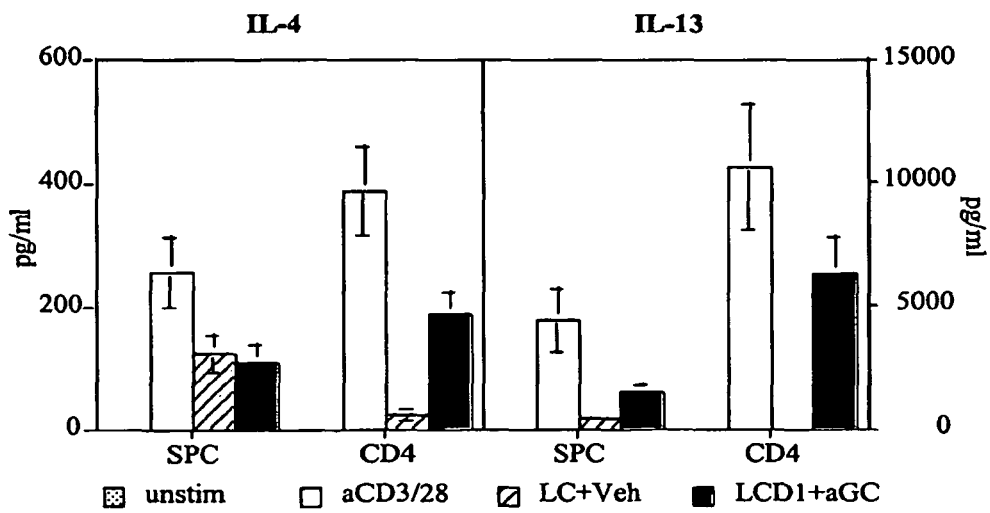

Fig. 10 cont'd
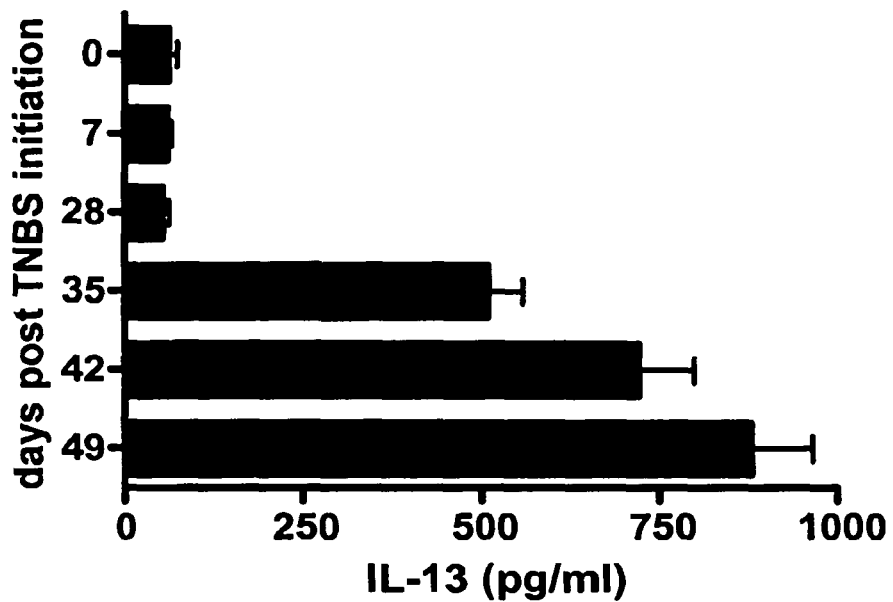
C
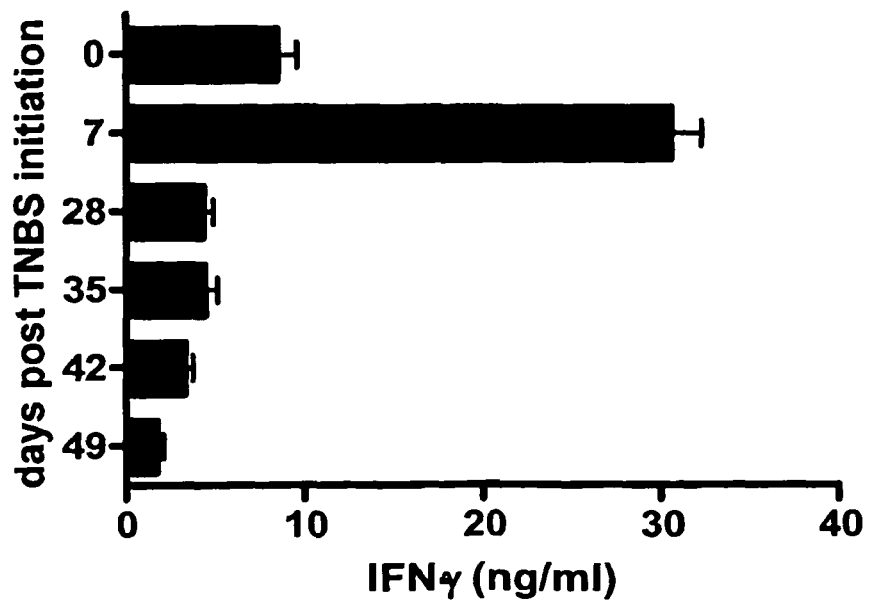
D

Fig. 10 cont'd
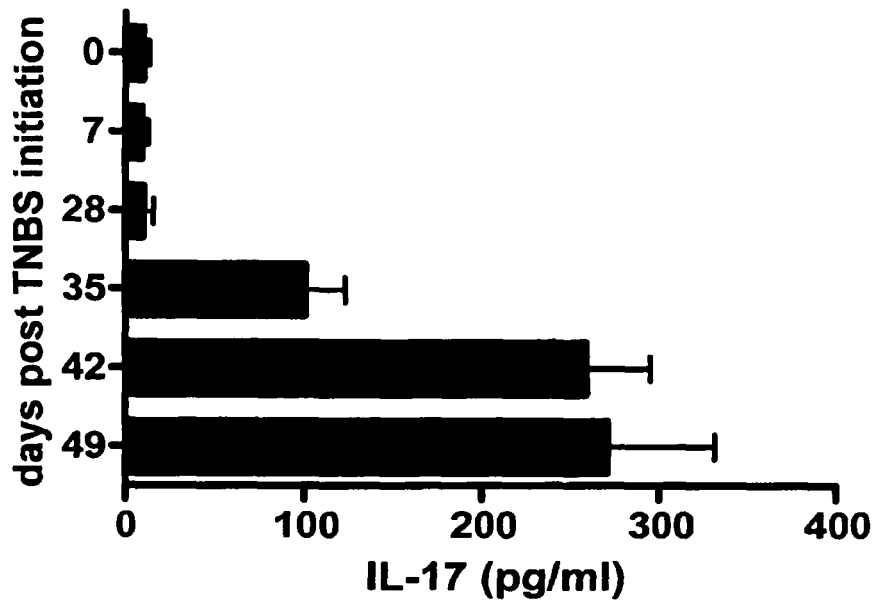
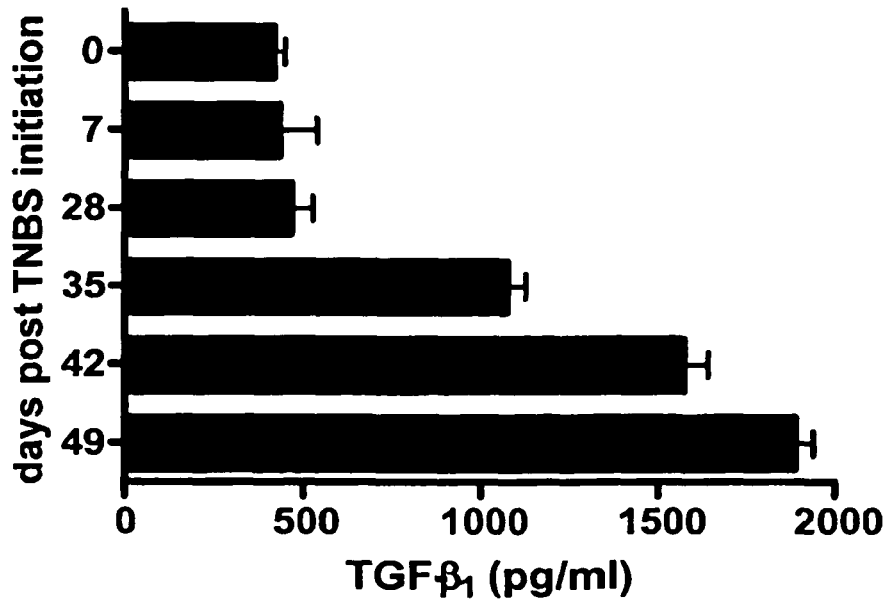

Fig. 12
A
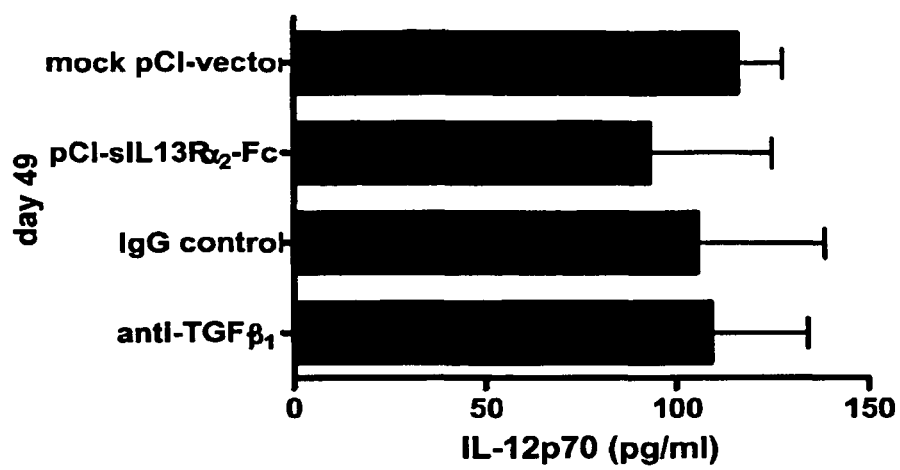
B
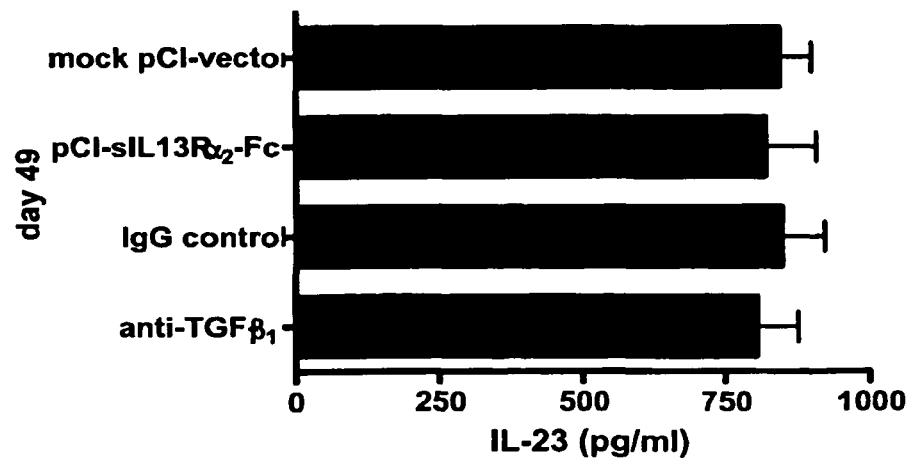

Fig. 12 cont'd
C
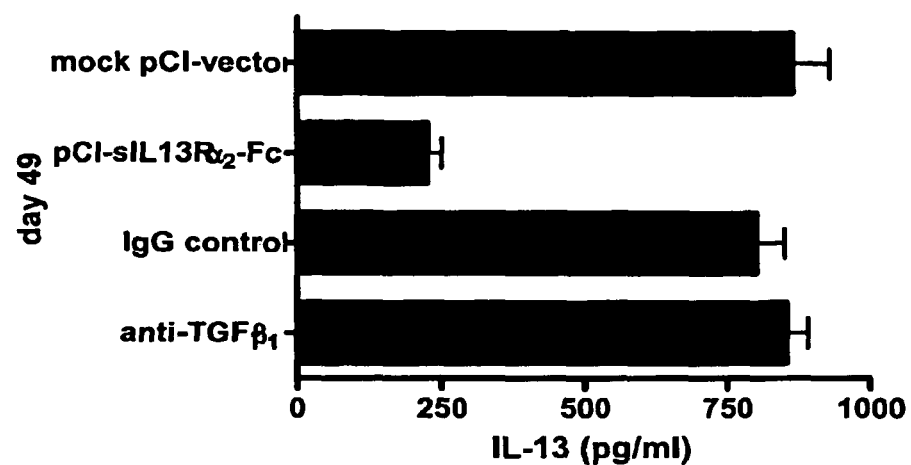
D
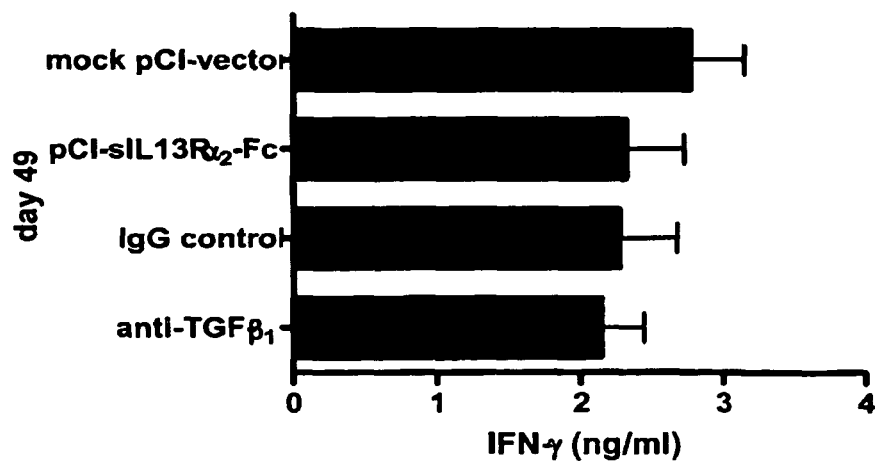

Fig. 12 cont'd
E
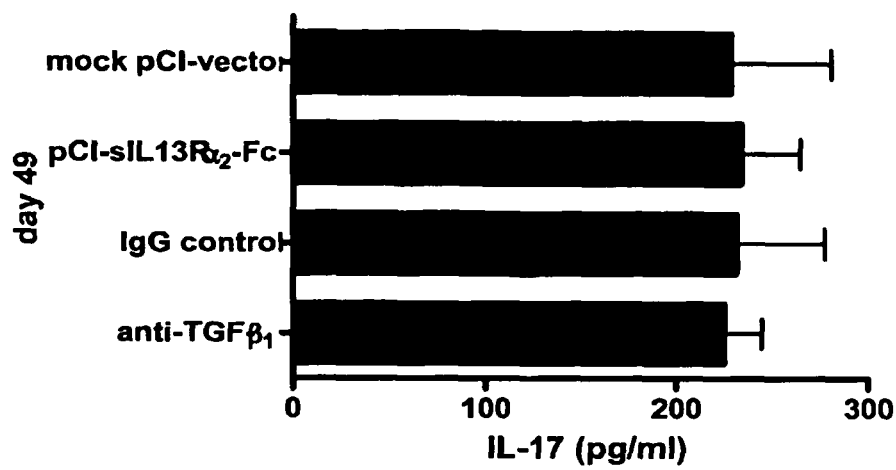
F
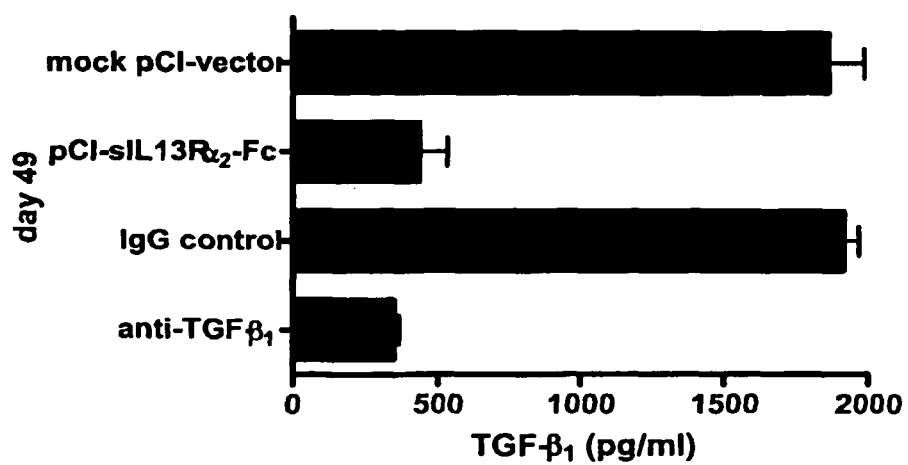

G

Fig. 14
A
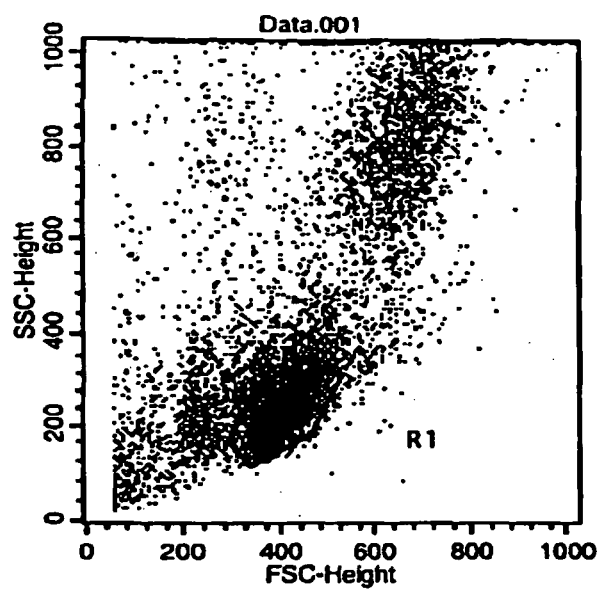
B
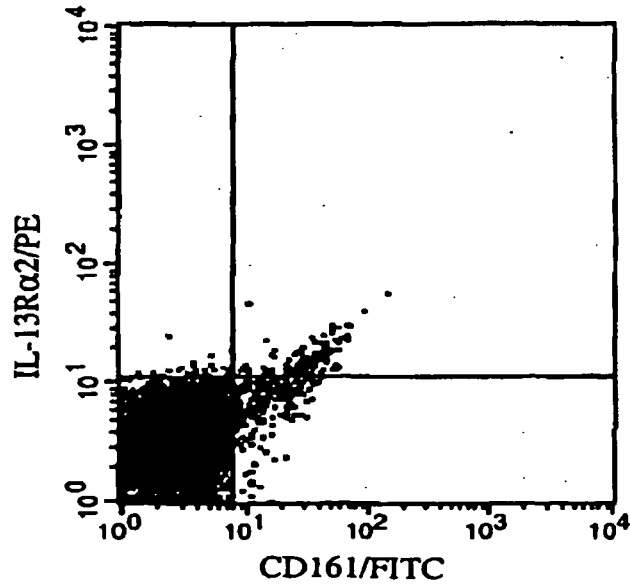

METHODS OF TREATING AND PREVENTING INFLAMMATORY BOWEL DISEASE INVOLVING IL-13 AND NKT CELLS

This application claims priority to U.S. provisional application Ser. No. 60/671,624 filed on Apr. 15, 2005 which is hereby incorporated by this reference in its entirety.

BACKGROUND OF THE INVENTION

Human inflammatory bowel disease (IBD) includes Crohn's disease and ulcerative colitis. Ulcerative colitis is a chronic disease of the colon, or large intestine. The disease is marked by inflammation and ulceration of the colon mucosa, or innermost lining. The inflammation usually begins in the rectum and lower colon, but it may also involve the entire colon, extending up the colon in a continuous manner. In contrast, Crohn's disease can affect any area of the gastrointestinal tract, including the small intestine and colon, is generally non-continuous, and can affect the entire thickness of the bowel wall.

Both Crohn's disease and ulcerative colitis are believed to be due to an abnormal mucosal T cell responsiveness to bacterial antigens in the gut lumen (Sartor, 1995). In people with IBD, the immune system reacts inappropriately, mistaking food, bacteria, and other materials in the intestine for foreign or invading substances. In the process, the body sends white blood cells into the lining of the intestines, where they produce chronic inflammation. These cells then generate harmful products that ultimately lead to ulcerations and bowel injury. When this happens, the patient experiences the symptoms of IBD.

It is estimated that as many as one million Americans have IBD—with that number evenly split between Crohn's disease and ulcerative colitis. Currently, there is no medical cure for IBD, however, current medical treatments are aimed at suppressing the abnormal inflammation in the colon lining and thereby controlling the symptoms. The major classes of medication that are currently used to treat IBD include aminosalicylates, corticosteroids, and immunomodulatory medicines. However, aminosalicylates are only effective in treating mild to moderate episodes of ulcerative colitis, steroids are not recommended for long-term use due to side effects, and the current immunomodulatory medications (e.g., Azathioprine, 6-mercaptopurine, and methotrexate) can take as long as three months before their beneficial effects begin to work. New and improved medical treatments are therefore needed to treat and prevent the symptoms of IBD.

SUMMARY OF THE INVENTION

Provided herein is a method of treating or preventing the inflammatory response of ulcerative colitis in a subject, comprising administering to the subject an effective amount of a substance that inhibits the binding of IL-13 to IL-13 receptors on T-cells, such as NKT cells.

Also provided is a method of treating or preventing inflammatory bowel disease (IBD) in a subject, comprising administering to the subject a therapeutic amount of a substance that modulates IL-13 activity. Thus, provided is a method of treating or preventing Crohn's disease in a subject, comprising administering to the subject a therapeutic amount of a substance that modulates IL-13 activity. Also provided is a method of treating or preventing ulcerative colitis in a subject, comprising administering to the subject a therapeutic amount of a substance that modulates IL-13 activity.

Also provided is a method of specifically delivering an effector molecule to an NKT cell comprising linking the effector molecule to an IL-13 receptor binding molecule (IL13RBM) and delivering to the cell an effective amount of the IL13RBM-linked effector molecule.

Also provided is a method of screening for a substance capable of blocking the binding of IL-13 to IL-13 receptors on NKT cells comprising: a) contacting NKT cells that express IL-13 receptor with the substance in the presence of an IL-13 receptor binding molecule, b) determining the ability of the substance to block binding of the IL-13 receptor binding molecule to the NKT cells contacted with the substance, a reduction in binding in the presence of the substance indicating that the substance is capable of blocking the binding of IL-13 to IL-13 receptors on NKT cells.

Also provided is a method of screening for a substance capable of blocking the binding of IL-13 to IL-13 receptor on NKT cells comprising: a) administering the substance to the animal having MD; and b) determining the ability of the substance to block binding of IL-13 to NKT cells. The animal with colitis can be an accepted animal model of colitis, such as oxazolone colitis as described herein and elsewhere.

Also provided is a method of screening for a substance capable of treating IBD (e.g. colitis or Crohn's disease) comprising a) administering the substance to an animal having IBD (e.g. colitis or Crohn's disease); b) assaying the animal for a reduction in IL-13 levels, a reduction in NKT cell levels or a reduction in binding of IL-13 to NKT cells, a reduction in any of these parameters indicating that the substance is capable of treating IBD.

BRIEF DESCRIPTION OF THE DRAWINGS

The accompanying drawings, which are incorporated in and constitute a part of this specification, illustrate several embodiments of the invention and together with the description, serve to explain the principles of the invention.

FIGS. 1A and 1B show weight loss and mortality, respectively, of mice after pre-sensitization with vehicle (ethanol) or oxazolone and intra-rectal challenge with vehicle or different doses of oxazolone. FIGS. C and E show 5× and 10× magnifications, respectively, of H.E. stained cross-sections from colons of mice 7 days after ethanol pre-sensitization and challenge. FIGS. 1D and 1F show effects after oxazolone pre-sensitization and re-challenge with 1% oxazolone intra-rectally.

FIGS. 5A-B show CD1 antigen presentation and that Jα281 NKT cells are essential for induction of oxazolone colitis. (A) Weight loss of mice after intra-rectal injection of vehicle (circles) or oxazolone after i.v. injection of blocking CD1 antibodies (20H2; diamonds) or control antibody (squares). (B) Weight loss after induction of oxazolone colitis of CD1KO mice (diamonds), Jα281KO mice (circles) and wildtype mice (squares).

FIG. 6 shows cytokine production in response to αGalCer. LPMC (upper panel), splenocytes or spleen CD4 cells (lower panel) were not stimulated (unstim.) or stimulated with plate-bound anti-CD3 and soluble anti-CD28 (aCD3/28), untransfected L-cells and vehicle (LC+Veh.), or CD1 transfected L-cells and 100 ng/ml αGalCer (LCD1+aGC).

FIG. 14 shows a representative flow cytometric analysis of peripheral blood mononuclear cells obtained from a ulcerative colitis patient. Two channel flow cytometric analysis was used to identify cells bearing both NKT cell markers (e.g., CD161) and IL-13 receptors, using antibodies conjugated with appropriate fluorochromes. In subjects with ulcerative colitis, 1.29-6.88% cells were found to co-express CD161 and IL-13Rα2, whereas in controls 0.16-0.38% cells were found to co-express these receptors.

DETAILED DESCRIPTION OF THE INVENTION

Figure 1:
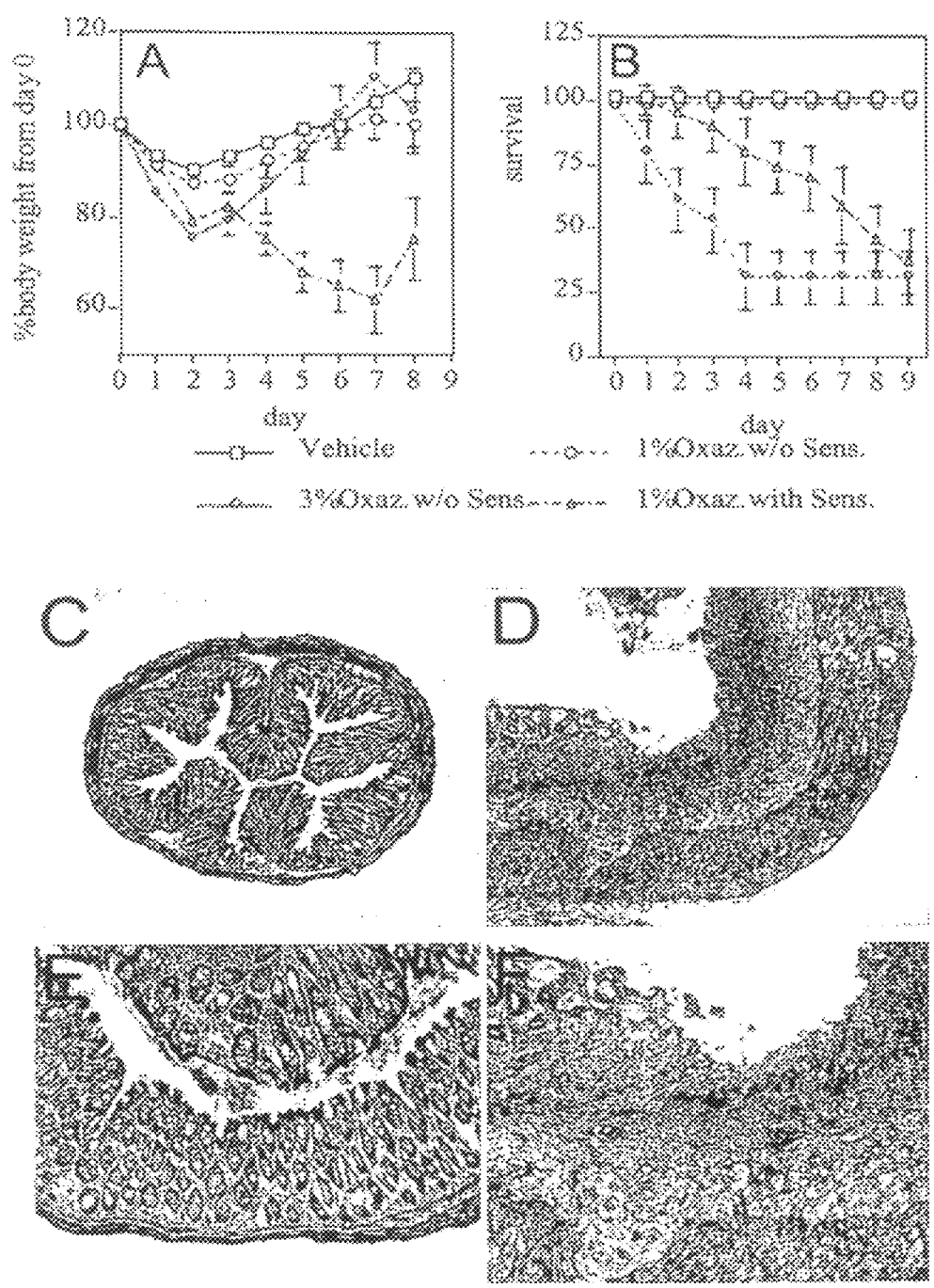
FIGS. 1A-F show that pre-sensitization before intra-rectal challenge with oxazolone leads to a chronic progressive colitis.

The present invention may be understood more readily by reference to the following detailed description of preferred embodiments of the invention and the Examples included therein and to the Figures and their previous and following description.

Before the present methods and compositions are disclosed and described, it is to be understood that this invention is not limited to specific methods or specific substances unless otherwise specified, or to particular reagents unless otherwise specified, as such may, of course, vary. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Thus, for example, reference to "a substance" includes one or more substances, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Methods of Treating or Preventing Ulcerative Colitis

Provided herein is a method of treating or preventing the inflammatory response of ulcerative colitis in a subject, comprising administering to the subject an effective amount of a substance that inhibits the binding of IL-13 to IL-13 receptors on T-cells, such as NKT cells. As disclosed herein, IL-13 receptors on T-cells, such as NKT cells, can be targeted using compositions and methods such as those provided herein to treat or prevent the inflammatory response of inflammatory bowel disease in a subject. As used herein, IL-13 includes all naturally occurring variants that can bind and stimulate IL-13 receptors, such as can be found on NKT cells.

Any animal which is subject to ulcerative colitis can be treated by this method. Therefore, the subject can be any mammal, such as human, and can include but is not limited to mouse, rat, cow, guinea pig, hamster, rabbit, cat, dog, goat, sheep, monkey, horse and chimpanzee.

A T-cell, as disclosed herein, can be any T-lymphocyte (e.g., helper, killer, suppressor) that is present in the gut and expresses an IL-13 receptor. Natural killer T (NKT) cells constitute a unique class of T-lymphocyte lineage that shares some characteristics with NK cells. These cells have an extremely restricted T-cell receptor (TCR) repertoire, consisting of an invariant Va24-JaQ chain preferentially paired with a Vβ11 chain in human beings. Although their natural TCR ligands remain to be identified, NKT cells can be generated and activated by glycolipid antigens such as α-galactosylceramide and glycosyl-phosphatidylinositol in the context of CD1d, a β2-microglobulin-associated major histocompatibility complex class I-like molecule. Human NKT cells express NK-associated C-type lectin NKR-P1 (CD161, the human version of mouse NK1.1) and CD45RO and are heterogeneous in expression of CD4 or CD8. In addition to identification by cell surface markers, NKT cells can be identified by the ability of the cell to recognize a nonpolymorphic class I antigen-presenting molecule, CD1d. For example, NKT cells can be identified functionally by the ability of the cell to produce cytokines, such as IL-13, in response to stimulation by antigen-presenting cells that bear CD1d (Fuss et al. 2004. J. Clin. Invest. 113:1490-7).

Inflammatory Bowel Disease

By "inflammatory bowel disease" (IBD) is meant a chronic recurrent inflammatory disease of unclear etiology affecting the small intestine and colon that includes both Crohn's disease (CD) and ulcerative colitis (UC). Crohn's disease can involve any portion of the intestinal tract but most commonly involves the distal small intestine and/or the colon. Ulcerative colitis involves only the colon, generally limited to the rectum or distal colon. Studies of murine models of CD and UC strongly suggest that both of these diseases are due to dysregulation of the mucosal immune response to antigens in the mucosal microflora (Sartor, R. B. (1995). Gastroenterol Clin North Am 24, 475-507) (Strober W, et al. (2002) Annu. Rev. Immunol. 20:495-549).

By "inflammatory response" or "immune response" is meant the reaction of living tissues to injury, infection or irritation characterized by redness, warmth, swelling, pain, and loss of function produced, as the result of increased blood flow and an influx of immune cells and secretions. Inflammation is the body's reaction to invading infectious microorganisms and results in an increase in blood flow to the affected area, the release of chemicals that draw white blood cells, an increased flow of plasma, and the arrival of monocytes to clean up the debris. Anything that stimulates the inflammatory response is said to be inflammatory.

One of skill in the art would recognize that ulcerative colitis or indeterminate colitis refers to a condition of the colon characterized by a state of inflammation in which one or more of the following histological characteristics are detectable: a superficial inflammation characterized by the presence of epithelial cell loss and patchy ulceration, pronounced depletion of mucin producing-goblet cells, and reduction of the density of the tubular glands. In addition, in the lamina propia, a mixed inflammatory cell infiltrate consisting of lymphocytes and granulocytes (the latter consisting mostly of neutrophils and, to a lesser extent, eosinophils) associated with an exudation of cells into the bowel lumen is observed. Also, the submucosal level can display marked edema with few inflammatory cells, while in the outer muscle layer one of skill in the art would see little or no evidence of inflammation. See e.g. Boirivant et al. *Journal of Experimental Medicine* 188: 1929-1939 (1998). Clinical symptoms can include, but are not limited to, diarrhea, rectal prolapse, weight loss, abdominal pain, and dehydration.

Crohn's disease refers to inflammation affecting any part of the alimentary tract but most often affecting the terminal part of the small bowel and/or the adjacent ascending colon. Frequently, the inflammation is characterized by "skip lesions" consisting of areas of inflammation alternating with area of normal mucosa. The affected area of bowel in Crohn's is marked by erythema, edema and increased friability; at times the bowel is strictured and attached to other abdominal organs or to the bowel wall. Fistulae between the affected bowel and other structures including the skin are not infrequent. Microscopic examination of the tissue in Crohn's disease reveals epithelial erosions, loss of mucin-producing goblet cells and an extensive lymphocytic infiltration involving all layers of the mucosa; this infiltrate sometimes contains giant cells indicative of granuloma formation. When inflammation is present for a long time (chronic), it sometimes can cause scarring (fibrosis). Scar tissue is typically not as flexible as healthy tissue. Therefore, when fibrosis occurs in the intestines, the scarring may narrow the width of the passageway (lumen) of the involved segments of the bowel. These constricted areas are called strictures. The strictures may be mild or severe, depending on how much they block the contents of the bowel from passing through the narrowed area. Clinical signs/symptoms of Crohn's disease can include but are not limited to: cachexia, weight loss, poor growth, abdominal pain, draining fistulae, rectal prolapse and dehydration.

As used herein, "binding" refers to the joining of two or more substances with sufficient specificity to have a chemical or biological effect. Examples of binding include the ionic interactions between a ligand and its receptor or an antibody and its antigen. It is understood that such binding is often a dynamic process wherein the binding is neither permanent nor complete. Thus, binding is not necessarily limited based on a specific avidity or affinity, so long as there is a significant biological or chemical effect of said binding. By "specificity" is meant that binding can be distinguishable over random interactions or background. Both the binding between substances as well as the chemical and biological effects can be measured for the methods provided herein.

Thus, a substance that inhibits the binding of IL-13 to IL-13 receptors on NKT cells can also inhibit the normal biological effect that would have occurred during that interaction. In addition, a substance that binds to an IL-13 receptor on a cell can activate the normal biological effect of the receptor, while concomitantly delivering an effector to the cell that, for example, results in the death of the cell.

By "treating" is meant that an improvement in the disease state, i.e., the inflammatory response of IBD, is observed and/or detected upon administration of a substance disclosed herein. Treatment can range from a positive change in a symptom or symptoms of the disease to complete amelioration of the inflammatory response of IBD (e.g., reduction in severity or intensity of disease, alteration of clinical parameters indicative of the subject's condition, relief of discomfort or increased or enhanced function), as detected by art-known techniques. The methods provided herein can be utilized to treat an established IBD.

By "preventing" is meant that after administration of a substance provided herein to a subject, there is a delay in the onset or reduction in magnitude of symptoms of CD or UC (e.g., inflammation, diarrhea, rectal prolapse, weight loss, abdominal pain etc.). As used throughout, "reverse" or "reversing" means to change to the opposite position, direction, or course, such as in to change the course of a disease from that of getting worse to that of getting better.

IL-13

The substance provided herein that can inhibit the binding of IL-13 to IL-13 receptors on NKT cells can comprise a modified IL-13. A modified IL-13 can also inhibit the binding of IL-13 to IL-13 receptors on epithelial cells in the gut. By "modified IL-13" is meant a non-native IL-13 (i.e., an IL-13 that has been altered, including for example, deletions, insertions, mutations, truncations, chimeras, conjugations, or fusions) but retains substantially the same receptor-binding characteristics of native IL-13. By "native" is meant a naturally occurring form, such as is found in nature. The modified IL-13 can be a modified human IL-13 (hIL-13). Interleukin-13 (IL-13) is a pleiotropic cytokine that is recognized to share many of the properties of IL-4, with which it shares approximately 30% sequence identity. It exhibits IL-4-like activities on monocytes/macrophages and human B cells (Minty et al., Nature, 362: 248 (1993), McKenzie et al. Proc. Natl. Acad. Sci. USA, 90:3735-3739 (1987) ("McKenzie et al."). The nucleotide and amino acid sequences of human IL-13 were determined and set forth in the publication by McKenzie et al., supra, and are also available on the Internet at, for example, the Entrez browser of the National Center for Biotechnology Information (www.ncbi.nlm.nih.gov) under GenBank Accession Number L06801.

The first eighteen amino acid residues of the sequence set forth by McKenzie et al. (through and including the third alanine) are considered in the art to be a signal sequence and the mature IL-13 protein is considered to commence with the nineteenth residue, a serine. SEQ ID NO:1 sets forth the translation (including the signal sequence, amino acids 1-18, and the mature IL-13 sequence, amino acids 19-132) as deposited by McKenzie et al., in GenBank under the accession number noted above. SEQ ID NO: 8 sets forth the mature IL-13 sequence (amino acids 19-132 of SEQ ID NO:1). References herein to particular residues of IL-13, such as residues 92, 110, and 112, and to percentages of identity to IL-13, are to the amino acid sequence of mature human IL-13 (SEQ ID NO:8). SEQ ID NO:2 is the nucleotide sequence for human IL-13, including the signal sequence and non-coding regions.

The modified IL-13 of the provided method can comprise a fragment of IL-13, such that the fragment of IL-13 is capable of binding IL-13 receptor but has a reduced ability to activate said receptor. For example, provided is a polypeptide consisting essentially of the receptor binding domain of IL-13. Three regions of hIL-13 that are required for receptor signaling have been localized to alpha-helices A, C and D. Glutamic acids at positions 13 and 16 in hIL-13 alpha-helix A, arginine and serine at positions 66 and 69 in helix C, and arginine at position 109 in helix D were found to be important in inducing biological signaling because these mutations resulted in the loss and/or gain of functional phenomena (Madhankumar A B, et al. J Biol. Chem. 2002 Nov. 8; 277 (45):43194-205). The IL-13 fragment disclosed herein can also be a mutated IL-13, i.e., an IL-13 fragment that includes an additional mutation (e.g. substitution, addition, internal deletion).

The modified IL-13 of the provided method can be circularly permuted IL-13 (cpIL-13) such that the cpIL-13 is capable of binding IL-13 receptor but has a reduced capacity to activate said receptor. Circular permutation is functionally equivalent to taking a straight-chain molecule, fusing the ends (directly or through a linker) to form a circular molecule, and then cutting the circular molecule at a different location to form a new straight chain molecule with different termini (see, e.g., Goldenberg, et al. J. Mol. Biol., 165: 407-413 (1983) and Pan et al. Gene 125: 111-114 (1993)). Circular permutation thus has the effect of essentially preserving the sequence and identity of the amino acids of a protein while generating new termini at different locations. Circular permutation of IL-13 provides a means by which the native IL-13 protein can be altered to produce new carboxyl and amino termini without diminishing the specificity and binding affinity for the IL-13 receptor on NKT cells. The making and use of cpIL-13 is described in U.S. Pat. No. 6,518,061, incorporated herein by reference in its entirety for this teaching.

It will be appreciated that while circular permutation is described in terms of linking the two ends of a protein and then cutting the circularized protein these steps are not actually required to create the end product. A protein can be synthesized de novo with the sequence corresponding to a circular permutation of the native protein. Thus, the term "circularly permuted IL-13 (cpIL-13)" refers to all IL-13 proteins having a sequence corresponding to a circular permutation of a native IL-13 protein regardless of how they are constructed. Generally, a permutation that retains or improves the binding specificity and/or avidity (as compared to the native IL-13) is preferred. If the new termini interrupt a critical region of the native protein, binding specificity and avidity can be lost.

There are two requirements for the creation of an active circularly permuted protein: 1) the termini in the native protein must be favorably located so that creation of a linkage does not destroy binding specificity and/or avidity; and 2) there must exist an "opening site" where new termini can be formed without disrupting a region critical for protein folding and desired binding activity (see, e.g., Thorton et A J. Mol. Biol., 167: 443-460 (1983)).

When circularly permuting IL-13, it is desirable to use a linker that preserves the spacing between the termini comparable to the unpermuted or native molecule. Generally linkers are either hetero- or homo-bifunctional molecules that contain two reactive sites that can each form a covalent bond with the carboxyl and the amino terminal amino acids respectively. Suitable linkers are well known to those of skill in the art and include, but are not limited to, straight or branched-chain carbon linkers, heterocyclic carbon linkers, or peptide linkers. The most common and simple example is a peptide linker that typically consists of several amino acids joined through peptide bonds to the termini of the native protein. The linkers can be joined to the terminal amino acids through their side groups (e.g., through a disulfide linkage to cysteine). In preferred embodiments, however, the linkers will be joined to the alpha carbon amino and carboxyl groups of the terminal amino acids. Functional groups capable of forming covalent bonds with the amino and carboxyl terminal amino acids are well known to those of skill in the art. For example, functional groups capable of binding the terminal amino group include anhydrides, carbodimides, acid chlorides, activated esters and the like. Similarly, functional groups capable of forming covalent linkages with the terminal carboxyl include amines, alcohols, and the like. The linker can itself be a peptide and be joined to the protein termini by peptide bonds.

IL-13 Mutants

The modified IL-13 of the provided method can be a mutant IL-13 that binds IL-13 receptor but has reduced capacity to activate signaling in said receptor. The mutant IL-13 can be a mutant human IL-13 (hIL-13). The mutant IL-13 can have a higher affinity for IL-13 receptor than native IL-13.

A "mutation" in a polypeptide can be the deletion, addition, or substitution of one or more amino acids in a polypeptide. A polypeptide arising as a result of a mutation is referred to herein as a "mutein." For example, a mutation can be substitution of an amino acid at a particular position in a polypeptide with a different amino acid at that position. Thus, for example, the mutation hIL-13E13K indicates that the native amino acid at position 13 in hIL-13 (glutamic acid, E) is replaced with lysine (K). The mutation does not require an actual removal and substitution of the amino acid(s) in question. The protein can be created de novo with the replacement amino acid in the position(s) of the desired mutation(s) so the net result is equivalent to the replacement of the amino acid in question.

Mutating the glutamic acid ("E") at position 13 to a neutral amino acid, or more preferably an amino acid which carries a positive charge at physiological pH, results in a mutant that is an antagonist of IL-13 (Oshima, Y. and Puri, R. K. (2001) J. Biol. Chem. 276: 15185-15191). That is, in the presence of such a mutant, the activity of endogenous IL-13 is reduced or wholly blocked. This permits the alleviation of conditions in which IL-13 is implicated as a causative or enhancing agent. Such conditions include, for example, asthma, allergic rhinitis, certain cancers, such as Hodgkin's Disease, Kaposi's sarcoma, and renal cell carcinoma, and susceptibility to Leishmaniasis. Remarkably, the presence of a mutation to a neutral amino acid or, more preferably, to a basic acidic acid at position of IL-13 causes the mutant to be an antagonist of IL-13 activity even if the molecule contains other mutations, such as changing the arginine at position 112 to aspartic acid, which would otherwise cause the mutant to be a strong agonist of IL-13 activity. For example, the double mutant IL-13E13KR112D is an antagonist of IL-13 activity (Oshima, Y and Puri R K. FASEB J. 2001 June; 15(8):1469-71) even though the mutant IL-13R112D is a strong agonist of IL-13-mediated activity (Oshima Y, et al. J Biol. Chem. 2000 May 12; 275(19):14375-80).

Mutants of IL-13 in which the glutamic acid at position 13 is changed to a residue with a neutral charge will act as antagonists of IL-13 activity. The glutamic acid at position 13 can be changed to a residue which is neutrally or positively charged at physiological pH. For example, the glutamic acid residue at position 13 in SEQ ID NO:8 can be mutated to lysine (IL-13E13K), arginine (IL-13E13R) or histidine (IL-13E13H). Thus, the modified IL-13 can be the mutant IL-13E13K of SEQ ID NO:8.

The mutant IL-13 disclosed herein can also be a truncated IL-13, i.e., an IL-13 fragment that includes an additional mutation (e.g. substitution, addition, internal deletion).

These and other IL-13 mutants are described in International Patent Application WO99/51643, International Patent Application WO01/25282, International Patent Application WO01/34645, U.S. Pat. No. 5,614,191, U.S. Pat. No. 5,919,456, U.S. Pat. No. 6,296,843, and U.S. Pat. No. 6,576,232, which are herein incorporated by reference in their entirety for the teaching of IL-13 mutants and the sequences thereof.

Chimeras

The substance of the present method can be a chimeric molecule comprising an IL-13 receptor binding molecule (IL13RBM) linked to an effector molecule. As used herein an "IL13RBM" refers to a molecule that binds to an IL-13 receptor with sufficient affinity and specificity to target IL-13 receptors significantly over background. The IL13RBM can be a native IL-13, such as for example hIL-13. In many instances the IL13RBM will not activate the IL-13 receptor. Thus, the IL13RBM can also be a modified IL-13, such as, for example a mutant IL-13 or IL-13 fragment. The IL13RBM can be an antibody against IL-13 receptor. Also, using the molecular model of an IL-13 receptor, other IL13RBM with appropriate structures can be provided.

A "chimeric molecule" is a single molecule created by joining two or more molecules that exist separately in their native state. The single, chimeric molecule has the desired functionality of all of its constituent molecules.

The effector molecule can be any molecule that can be conjugated to an IL13RBM and exert a particular function. The effector molecule typically has a characteristic activity that is desired to be delivered to the target NKT cell. Non-limiting examples of effector molecules include cytotoxins, labels, radionuclides, antibodies, and pharmacological agents.

An IL13RBM conjugated with one or more cytotoxins can be used to kill cells expressing (or overexpressing) an IL-13 receptor, e.g. NKT cells. As used herein, cytotoxins can be any cytotoxic agent (i.e., molecule that can kill a cell after contacting the cell), or a cytotoxic subunit or mutant thereof, that can be conjugated to an IL13RBM. Examples of cytotoxins include, without limitation, radionuclides (e.g., $^{35}S$, $^{14}C$, $^{32}P$, $^{125}I$, $^{131}I$, $^{90}Y$, $^{89}Zr$, $^{201}Tl$, $^{186}Re$, $^{188}Re$, $^{57}Cu$, $^{213}Bi$, $^{211}At$, etc.), conjugated radionuclides, and chemotherapeutic agents. Further examples of cytotoxins include, but are not limited to, antimetabolites (e.g., 5-fluorouricil (5-FU), methotrexate (MTX), fludarabine, etc.), anti-microtubule agents (e.g., vincristine, vinblastine, colchicine, taxanes (such as paclitaxel and docetaxel), etc.), alkylating agents (e.g., cyclophasphamide, melphalan, bischloroethylnitrosurea (BCNU), etc.), platinum agents (e.g., cisplatin (also termed cDDP), carboplatin, oxaliplatin, JM-216, CI-973, etc.), anthracyclines (e.g., doxorubicin, daunorubicin, etc.), antibiotic agents (e.g., mitomycin-C), topoisomerase inhibitors (e.g., etoposide, tenoposide, and camptothecins). The cytotoxin of the present method can further be *Pseudomonas* exotoxin (PE) or a cytotoxic subunit or mutant thereof, Diptheria toxin (DT) or a cytotoxic subunit or mutant thereof, ricin, saporin, gelonin, calicheamycin, doxorubicin, ribotoxin, ribosome inactivating protein, or abrin. The herein disclosed cytotoxins can also be modified to remove their capacity for non-specific binding.

*Pseudomonas* exotoxin A (PE) is an extremely active monomeric protein (molecular weight 66 kD), secreted by *Pseudomonas aeruginosa*, which inhibits protein synthesis in eukaryotic cells through the inactivation of elongation factor 2 (EF-2) by catalyzing its ADP-ribosylation (catalyzing the transfer of the ADP ribosyl moiety of oxidized NAD onto EF-2). PE contains three structural domains that act in concert to cause cytotoxicity. The structure of PE is known in the art and disclosed in, for example, Pastan I, et al. (Annu Rev Biochem. 1992. 61:331-54) and Debinski W, et al. (J. Biol. Chem. 1995. 270(28):16775-80), hereby incorporated herein by reference in their entirety for the teaching of the use of *Pseudomonas* exotoxin A structure and modifications thereto. The sequence for PE can be accessed on the GenBank database via Accession No. K01397 (SEQ ID NO:3). Domain Ia (amino acids 1-252) mediates cell binding. Domain II (amino acids 253-364) is responsible for translocation into the cytosol and domain III (amino acids 400-613) mediates ADP ribosylation of elongation factor 2, which inactivates the protein and causes cell death. The function of domain Ib (amino acids 365-399) remains undefined, although a large part of it, amino acids 365-380, can be deleted without loss of cytotoxicity. Further, removal of domain Ia results in a truncated PE molecule (PE40), which retains full ADP-ribosylation activity. See Siegall et al., J. Biol. Chem. 264: 14256-14261 (1989), hereby incorporated herein by reference in its entirety for its teaching of the use of *Pseudomonas* exotoxin A in a fusion protein.

In addition, the PE molecules can be further modified using site-directed mutagenesis or other techniques known in the art, to alter the molecule for a particular desired application. Means to alter the PE molecule in a manner that does not substantially affect the functional advantages provided by the PE molecules described here can also be used and such resulting molecules are intended to be covered herein.

For maximum cytotoxic properties of a PE molecule, several modifications to the molecule are disclosed. Modifications to the carboxyl terminal sequence of PE affect the translocation of the molecule into the cytosol of target cells. Amino acid sequences which have been found to be effective include, REDLK (SEQ ID NO:5) (as in native PE), REDL (SEQ ID NO:6), RDEL (SEQ ID NO:7), or KDEL (SEQ ID NO:4), repeats of those, or other sequences that function to maintain or recycle proteins into the endoplasmic reticulum, referred to here as "endoplasmic retention sequences". See, for example, Chaudhary et al, Proc. Nad. Acad. Sci. USA 87:308-312 and Seetharam et al, J. Biol. Chem. 266: 17376-17381 (1991).

Deletions of amino acids 365-380 of domain Ib can be made without loss of activity. Further, a substitution of methionine at amino acid position 280 in place of glycine to allow the synthesis of the protein to begin and of serine at amino acid position 287 in place of cysteine to prevent formation of improper disulfide bonds is beneficial.

The IL13RBM can be inserted in replacement for domain Ia. A similar insertion has been accomplished in what is known as the TGFα-PE40 molecule (also referred to as TP40) described in Heimbrook et al., Proc. Natl. Acad. Sci., USA, 87: 4697-4701 (1990) and in U.S. Pat. No. 5,458,878, incorporated herein by reference in their entirety for their teaching of this method.

The IL13RBM of the provided method can be linked to the PE molecule designated PE38. This PE molecule is a truncated form of PE composed of amino acids 253-364 and 381-608. The IL13RBM of the provided method can be linked to PE38 followed by the native sequences REDLK (SEQ ID NO:5) or the mutant sequences KDEL (SEQ ID NO:4) or RDEL (SEQ ID NO:7). Lysines at positions 590 and 606 can optionally be mutated to glutamine. Moreover, PE38 can be further modified to create a variant known as PE38QQR by replacing the lysine residues at positions 509 and 606 by glutamine and replacing the residue at 613 by arginine (Debinski et al. Bioconj. Chem., 5: 40 (1994)). The IL13RBM of the provided method can be linked to the PE molecule designated PE4E. PE4E is a "full length" PE with a mutated and inactive native binding domain where amino acids 57, 246, 247, and 249 are all replaced by glutamates (see, e.g., Chaudhary et al., J. Biol. Chem., 265: 16306 (1995)). Thus, in one aspect, the effector molecule of the provided method is the *Pseudomonas* exotoxin PE35, PE38, PE38 KDEL, PE40, PE4E, or PE38QQR.

The IL13RBM of the provided method can be inserted at a point within domain III of the PE molecule. The IL13RBM can be fused between about amino acid positions 607 and 609 of the PE molecule. This means that the targeting molecule is inserted after about amino acid 607 of the molecule and an appropriate carboxyl end of PE is recreated by placing amino acids about 604-613 of PE after the targeting molecule. Thus, the targeting molecule is inserted within the recombinant PE molecule after about amino acid 607 and is followed by amino acids 604-613 of domain III. The IL13RBM can also be inserted into domain 1b to replace sequences not necessary for toxicity (Debinski, et al. (1991) Mol. Cell. Biol., 11:1751-1753).

The PE molecules can be fused to the targeting molecule (e.g., IL13RBM) by recombinant means. The genes encoding protein chains can be cloned in cDNA or in genomic form by any cloning procedure known to those skilled in the art (see, e.g., Sambrook et al., Molecular Cloning: A Laboratory Manual, Cold Spring Harbor Laboratory, (1989)). Methods of cloning genes encoding PE fused to various ligands are well known to those of skill in the art (see, e.g., Siegall et al., FASEB J, 3:2647-2652 (1989); and Chaudhary et al. Proc. Natl. Acad. Sci. USA, 84: 4538-4542 (1987)).

Those skilled in the art will realize that additional modifications, deletions, insertions and the like can be made to the chimeric molecules of the present method or to the nucleic acid sequences encoding IL-13 receptor-directed chimeric molecules.

Like PE, Diphtheria toxin (DT) kills cells by ADP-ribosylating elongation factor 2 thereby inhibiting protein synthesis. Diphtheria toxin, however, is divided into two chains, A and B, linked by a disulfide bridge. In contrast to PE, chain B of DT, which is on the carboxyl end, is responsible for receptor binding and chain A, which is present on the amino end, contains the enzymatic activity (Uchida et al., Science, 175: 901-903 (1972); Uchida et al. J. Biol. Chem., 248: 3838-3844 (1973)).

The term "Diphtheria toxin" (DT) as used herein refers to full length native DT or to a DT that has been modified. Modifications typically include removal of the targeting domain in the B chain and, more specifically, involve truncations of the carboxyl region of the B chain. The native receptor-binding domain of DT can be removed by truncation of the Diphtheria toxin B chain. For example, the DT can be DT388, wherein the carboxyl terminal sequence beginning at residue 389 is removed, or DT398, wherein the carboxyl terminal sequence beginning at residue 399 is removed (Chaudhary, et al, (1991 Bioch. Biophys. Res. Comm., 180: 545-551). Other examples of DT are known in the art, and these DTs are useful as the cytotoxin moiety of the chimeras disclosed for use in the methods taught herein.

Like the PE chimeric cytotoxins, the DT molecules can be chemically conjugated to an IL-13 molecule or fused to IL-13 by recombinant means. The genes encoding protein chains can be cloned in cDNA or in genomic form by any cloning procedure known to those skilled in the art. Methods of cloning genes encoding DT fused to various ligands are also well known to those of skill in the art (see, e.g., Williams et al. J. Biol. Chem. 265: 11885-11889 (1990)).

Other effector molecules, including other cytotoxins, are described in International Patent Application WO99/51643, International Patent Application WO01/25282, International Patent Application WO01/34645, International Patent Application WO03/047632, U.S. Pat. No. 5,614,191, U.S. Pat. No. 5,919,456, U.S. Pat. No. 6,296,843, U.S. Pat. No. 6,428,788, and U.S. Pat. No. 6,576,232, which are all herein incorporated by reference in the entirety for the teaching of effector molecules and IL-13 chimeras.

Detectable Labels

Detectable labels suitable for use as the effector molecule component of the chimeric molecules of this invention include any composition detectable by spectroscopic, photochemical, biochemical, immunochemical, electrical, optical or chemical means. Useful labels in the present invention include magnetic beads (e.g. DynabeadSTM), fluorescent dyes (e.g., fluorescein isothiocyanate, texas red, rhodamine, green fluorescent protein, and the like), radiolabels (e.g., $^{3}$H, $^{125}$I, $^{35}$S, $^{14}$C, or $^{32}$P),) enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads.

Means of detecting such labels are well known to those of skill in the art. Thus, for example, radiolabels can be detected using photographic film or scintillation counters, fluorescent markers can be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

Pharmacological Agents

Other suitable effector molecules include pharmacological agents or encapsulation systems containing various pharmacological agents. Thus, the targeting molecule of the chimeric molecule can be attached directly to a drug that is to be delivered directly to the NKT cell. Such drugs are well known to those of skill in the art and include, but are not limited to, doxirubicin, ribotoxin, vinblastine, genistein, an antisense molecule, and the like. Doxirubicin and ribotoxin are nonimmunogenic and can therefore be used in multiple applications.

Disclosed is an IL13RBM conjugated to one or more delivery vehicles. Such conjugates can be used to deliver other substances such as a drug to cells expressing a receptor to which IL-13 binds. Any delivery vehicle that can be conjugated to an IL13RBM can be used. Examples of such delivery vehicles include liposomes and lipids (e.g., micelles). Liposomes encapsulating drugs or micelles including drugs can also be used. Methods for preparing liposomes attached to proteins are well known to those of skill in the art. See, for example, U.S. Pat. No. 4,957,735; and Connor et al., *Pharm. Ther.*, 28: 341-365 (1985).

Nucleic Acids

IL13RBM conjugated with one or more nucleic acids can be used to specifically target delivery of the nucleic acid(s) to a target cell (e.g., one expressing a receptor to which IL-13 binds). Any nucleic acid that can be conjugated to an IL13RBM can be used. The nucleic acids can be attached directly to the IL13RBM, attached via a linker, or complexed with or encapsulated in another moiety (e.g., a lipid, a liposome, a viral coat, or the like) that is attached to the IL13RBM. The nucleic acid can provide any of number of effector functions. For example, a nucleic acid encoding one or more proteins can be used to deliver a particular enzymatic activity, substrate, and/or epitope to a target cell. For these applications or others where expression (e.g. transcription or translation) of the nucleic acid is desired, the nucleic acid is preferably a component of an expression cassette that includes all the regulatory sequences necessary to express the nucleic acid in the cell. Suitable expression cassettes typically include promoter initiation and termination codons, and are selected to optimize expression in the target cell. Methods of constructing suitable expression cassettes are well known to those of skill in the art.

Conjugation

The targeting molecule and the effector molecule can be attached by any of a number of means well known to those of skill in the art. Thus, the effector molecule can be conjugated (e.g., covalently bonded) to an IL13RBM by any method known in the art for conjugating two such molecules together. For example, the IL13RBM can be chemically derivatized with an effector molecule either directly or using a linker (spacer). Several methods and reagents (e.g., cross-linkers) for mediating this conjugation are known. See, e.g., catalog of Pierce Chemical Company; and Means and Feeney, *Chemical Modification of Proteins*, Holden-Day Inc., San Francisco, Calif. 1971. Various procedures and linker molecules for attaching various compounds including radionuclide metal chelates, toxins, and drugs to proteins (e.g., to antibodies) are described, for example, in European Patent Application No. 188,256; U.S. Pat. Nos. 4,671,958; 4,659, 839; 4,414,148; 4,699,784; 4,680,338; 4,569,789; and 4,589,071; and Borlinghaus et al. *Cancer Res.* 47: 4071-4075 (1987). In particular, production of various immunotoxins is well-known within the art and can be found, for example in "Monoclonal Antibody—Toxin Conjugates: Aiming the Magic Bullet," Thorpe et al., *Monoclonal Antibodies in Clinical Medicine*, Academic Press, pp. 168-190 (1982); Waldmann (1991) *Science,* 252: 1657; and U.S. Pat. Nos. 4,545,985 and 4,894,443.

Where the effector molecule is a polypeptide, the chimeric molecule including the IL13RBM molecule and the effector can be a fusion protein. A "fusion protein" refers to a polypeptide formed by the joining of two or more polypeptides through a peptide bond formed between the amino terminus of one polypeptide and the carboxyl terminus of another polypeptide. The fusion protein can be formed by the chemical coupling of the constituent polypeptides or it can be expressed as a single polypeptide from nucleic acid sequence encoding the single contiguous fusion protein. A single chain fusion protein is a fusion protein having a single contiguous polypeptide backbone. Fusion proteins can be prepared using conventional techniques in molecular biology to join the two genes in frame into a single nucleic acid, and then expressing the nucleic acid in an appropriate host cell under conditions in which the fusion protein is produced.

One of skill will appreciate that the targeting molecule and effector molecules can be joined together in any order. Thus, where the targeting molecule is a polypeptide, the effector molecule can be joined to either the amino or carboxy termini of the targeting molecule. The targeting molecule can also be joined to an internal region of the effector molecule, or conversely, the effector molecule can be joined to an internal location of the targeting molecule, as long as the attachment does not interfere with the respective activities of the molecules.

In some circumstances, it is desirable to free the effector molecule from the IL13RBM when the chimeric molecule has reached its target site. Therefore, chimeric conjugates comprising linkages that are cleavable in the vicinity of the target site can be used when the effector is to be released at the target site. Cleaving of the linkage to release the effector molecule from the IL13RBM can be prompted by enzymatic activity or conditions to which the conjugate is subjected either inside the target cell or in the vicinity of the target site. A number of different cleavable linkers are known to those of skill in the art. See, e.g., U.S. Pat. Nos. 4,618,492; 4,542,225; and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient's complement system. In view of the large number of methods that have been reported for attaching a variety of radiodiagnostic compounds, radiotherapeutic compounds, drugs, toxins, and other agents to antibodies one skilled in the art will be able to determine a suitable method for attaching a given effector molecule to a IL-13 molecule.

Soluble IL-13 Receptors

The substance provided herein that can inhibit the binding of IL-13 to IL-13 receptors on NKT cells can comprise a soluble IL-13 receptor. A soluble IL-13 receptor can, for example, be an IL-13 receptor linked to the constant region (Fc) of an immunoglobulin (i.e., a cytokine trap). The soluble IL-13 receptor of the provided method can comprise IL-13Rα or IL-13Rα2. The IL-13Rα can be rat IL-13Rα, or fragments thereof. The sequence for this receptor can be accessed on the GenBank database via Accession No. AY044251. The IL-13Rα can also be the mouse IL-13Ra, or fragments thereof. The sequence for this receptor can be accessed on the GenBank database via Accession No. 580963. The IL-13Rα can also be the human IL-13Rα, or fragments thereof. The sequence for this receptor can be accessed on the GenBank database via Accession No. U62858.

The IL-13Rα2 can be the human IL-13Rα2, or fragments thereof. The sequence for this receptor can be accessed on the GenBank database via Accession No. NM_000640. The IL-13Rα2 can also be the mouse IL-13Rα2, or fragments thereof. The sequence for this receptor can be accessed on the GenBank database via Accession No. U65747.

Antibodies

The substance provided herein that can inhibit the binding of IL-13 to IL-13 receptors on NKT cells can comprise an antibody. As used herein, the term "antibody" encompasses, but is not limited to, whole immunoglobulin (i.e., an intact antibody) of any class. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (k) and lambda (l), based on the amino acid sequence of their constant domains. Depending on the amino acid sequence of the constant domain of their heavy chains, immunoglobulins can be assigned to different classes. There are five major classes of human immunoglobulins: IgA, IgD, IgE, IgG and IgM, and several of these can be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

The antibody of the provided method can be antibodies against human IL-13 (Dolganov, et al. "Coexpression of the interleukin-13 and interleukin-4 genes correlates with their physical linkage in the cytokine gene cluster on human chromosome 5q23-31" *Blood* 87 (8), 3316-3326 (1996)). The sequence of human IL-13 can be accessed on GenBank via Accession No. U31120 and is incorporated herein in its entirety by this reference. The antibodies of the provided method can also be antibodies against mouse IL-13 (Brown, et al. "A family of small inducible proteins secreted by leukocytes are members of a new superfamily that includes leukocyte and fibroblast-derived inflammatory agents, growth factors, and indicators of various activation processes" *J. Immunol.* 142 (2), 679-687 (1989)). This sequence can be accessed on the GenBank database via Accession No. NM_008355 and is incorporated herein it its entirety by this reference.

The antibody of the provided method can be an antibody against IL-13 receptor. Such an antibody is an IL13RBM of the method.

The term "variable" is used herein to describe certain portions of the variable domains that differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies (see Kabat E. A. et al., "Sequences of Proteins of Immunological Interest," National Institutes of Health, Bethesda, Md. (1987)). The constant domains are not involved directly in binding an antibody to an antigen, but exhibit various effector functions, such as participation of the antibody in antibody-dependent cellular toxicity.

As used herein, the term "antibody or fragments thereof" encompasses chimeric antibodies and hybrid antibodies, with dual or multiple antigen or epitope specificities, and fragments, such as F(ab')2, Fab', Fab, scFv and the like, including hybrid fragments. Thus, fragments of the antibodies that retain the ability to bind their specific antigens are provided. For example, fragments of antibodies which maintain IL-13, IL-13Rα, or IL-13Rα2 binding activity are included within the meaning of the term "antibody or fragment thereof." Such antibodies and fragments can be made by techniques known in the art and can be screened for specificity and activity according to the methods set forth in the Examples and in general methods for producing antibodies and screening antibodies for specificity and activity (See Harlow and Lane. Antibodies, A Laboratory Manual. Cold Spring Harbor Publications, New York, (1988)).

Also included within the meaning of "antibody or fragments thereof" are conjugates of antibody fragments and antigen binding proteins (single chain antibodies) as described, for example, in U.S. Pat. No. 4,704,692, the contents of which is hereby incorporated by reference herein in its entirety.

Optionally, the antibodies are generated in other species and "humanized" for administration in humans. Humanized forms of non-human (e.g., murine) antibodies are chimeric immunoglobulins, immunoglobulin chains or fragments thereof (such as Fv, Fab, Fab', F(ab')2, scFv or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies can also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., *Nature,* 321:522-525 (1986); Riechmann et al., Nature, 332:323-327 (1988); and Presta, *Curr. Op. Struct. Biol.,* 2:593-596 (1992)).

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., *Nature,* 321:522-525 (1986); Riechmann et al., *Nature,* 332:323-327 (1988); Verhoeyen et al., *Science,* 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody (Sims et al., *J. Immunol.*, 151:2296 (1993); Chothia et al., *J. Mol. Biol.*, 196:901 (1987)). Another method uses a particular framework derived from the consensus sequence of all human antibodies of a particular subgroup of light or heavy chains. The same framework can be used for several different humanized antibodies (Carter et al., *Proc. Natl. Acad. Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding (see, WO 94/04679, published 3 Mar. 1994).

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge (see, e.g., Jakobovits et al., *Proc. Natl. Acad. Sci. USA*, 90:2551-255 (1993); Jakobovits et al., Nature, 362:255-258 (1993); Bruggemann et al., *Year in Immunol.*, 7:33 (1993)). Human antibodies can also be produced in phage display libraries (Hoogenboom et al., *J. Mol. Biol.*, 227:381 (1991); Marks et al., *J. Mol. Biol.*, 222:581 (1991)). The techniques of Cote et al. and Boerner et al. are also available for the preparation of human monoclonal antibodies (Cole et al., Monoclonal Antibodies and Cancer Therapy, Alan R. Liss, p. 77 (1985); Boerner et al., *J. Immunol.*, 147(1):86-95 (1991)).

The antibody of the present method can be a monoclonal antibody. The term "monoclonal antibody" as used herein refers to an antibody obtained from a substantially homogeneous population of antibodies, i.e., the individual antibodies comprising the population are identical except for possible naturally occurring mutations that can be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired activity (See, U.S. Pat. No. 4,816,567 and Morrison et al., *Proc. Natl. Acad. Sci. USA*, 81:6851-6855 (1984)).

Monoclonal antibodies can be prepared using hybridoma methods, such as those described by Kohler and Milstein, Nature, 256:495 (1975) or Harlow and Lane. Antibodies, A Laboratory Manual. Cold Spring Harbor Publications, New York, (1988). In a hybridoma method, a mouse or other appropriate host animal, is typically immunized with an immunizing agent to elicit lymphocytes that produce or are capable of producing antibodies that will specifically bind to the immunizing agent. Alternatively, the lymphocytes can be immunized in vitro. The immunizing agent can comprise IL-13 or fragment thereof (e.g., IL13RBM), or IL-13 receptor (e.g., IL-13Ra, or IL-13Rα2) or fragment thereof. Traditionally, the generation of monoclonal antibodies has depended on the availability of purified protein or peptides for use as the immunogen. More recently DNA based immunizations have been employed to elicit strong immune responses and generate monoclonal antibodies. In this approach, DNA-based immunization is used, wherein DNA encoding IL-13 or fragment thereof (e.g., IL13RBM), or soluble IL-13 receptor (e.g., IL-13Ra, or IL-13Rα2) or fragment thereof expressed as a fusion protein with human IgG1 is injected into the host animal according to methods known in the art (e.g., Kilpatrick K E, et al. Gene gun delivered DNA-based immunizations mediate rapid production of murine monoclonal antibodies to the Flt-3 receptor. *Hybridoma*. 1998 December; 17(6):569-76; Kilpatrick K E et al. High-affinity monoclonal antibodies to PED/PEA-15 generated using 5 µg of DNA. *Hybridoma*. 2000 August; 19(4):297-302, which are incorporated herein by referenced in full for the methods of antibody production) and as described in the examples.

An alternate approach to immunization with either purified protein or DNA is to use antigen expressed in baculovirus. The advantages to this system include ease of generation, high levels of expression, and post-translational modifications that are highly similar to those seen in mammalian systems. This results in the display of the foreign proteins on the surface of the virion. This method allows immunization with whole virus, eliminating the need for purification of target antigens.

Generally, either peripheral blood lymphocytes ("PBLs") are used in methods of producing monoclonal antibodies if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice* Academic Press, (1986) pp. 59-103). Immortalized cell lines are usually transformed mammalian cells, including myeloma cells of rodent, bovine, equine, and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells. Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies (Kozbor, *J. Immunol.*, 133:3001 (1984); Brodeur et al., "Monoclonal Antibody Production Techniques and Applications" Marcel Dekker, Inc., New York, (1987) pp. 51-63). The culture medium in which the hybridoma cells are cultured can then be assayed for the presence of monoclonal antibodies directed against IL-13 or fragment thereof (e.g., IL13RBM), or soluble IL-13 receptor (e.g., IL-13Rα, or IL-13Rα2) or fragment thereof. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art, and are described further in the Examples below or in Harlow and Lane *Antibodies, A Laboratory Manual* Cold Spring Harbor Publications, New York, (1988).

After the desired hybridoma cells are identified, the clones can be subcloned by limiting dilution or FACS sorting procedures and grown by standard methods. Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, protein G, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies disclosed herein can be readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA can be placed into expression vectors, which are then transfected into host cells such as simian COS cells, Chinese hamster ovary (CHO) cells, plasmacytoma cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Optionally, such a non-immunoglobulin polypeptide is substituted for the constant domains of an antibody of the provided method or substituted for the variable domains of one antigen-combining site of an antibody of the present method to create a chimeric bivalent antibody comprising one antigen-combining site having specificity for IL-13 or fragment thereof (e.g., IL13RBM), or soluble IL-13 receptor (e.g., IL-13Rα, or IL-13Rα2) or fragment thereof and another antigen-combining site having specificity for a different antigen.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994, U.S. Pat. No. 4,342,566, and Harlow and Lane, Antibodies, A Laboratory Manual, Cold Spring Harbor Publications, New York, (1988). Papain digestion of antibodies typically produces two identical antigen binding fragments, called Fab fragments, each with a single antigen binding site, and a residual Fc fragment. Pepsin treatment yields a fragment, called the F(ab')2 fragment, that has two antigen combining sites and is still capable of cross-linking antigen.

The Fab fragments produced in the antibody digestion also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')2 fragment is a bivalent fragment comprising two Fab' fragments linked by a disulfide bridge at the hinge region. Fab'-SH is the designation herein for Fab' in which the cysteine residue(s) of the constant domains bear a free thiol group. Antibody fragments originally were produced as pairs of Fab' fragments which have hinge cysteines between them. Other chemical couplings of antibody fragments are also known.

An isolated immunogenically specific paratope or fragment of the antibody is also provided. A specific immunogenic epitope of the antibody can be isolated from the whole antibody by chemical or mechanical disruption of the molecule. The purified fragments thus obtained are tested to determine their immunogenicity and specificity by the methods taught herein. Immunoreactive paratopes of the antibody, optionally, are synthesized directly. An immunoreactive fragment is defined as an amino acid sequence of at least about two to five consecutive amino acids derived from the antibody amino acid sequence.

One method of producing proteins comprising the antibodies disclosed herein is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the antibody of the provided method, for example, can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant. *Synthetic Peptides: A User Guide*. W.H. Freeman and Co., N.Y. (1992); Bodansky and Trost., Ed. (1993) *Principles of Peptide Synthesis*. Springer-Verlag Inc., NY. Alternatively, the peptide or polypeptide is independently synthesized in vivo as described above. Once isolated, these independent peptides or polypeptides can be linked to form an antibody or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen et al., *Biochemistry*, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. *Science*, 266:776-779 (1994)). The first step is the chemoselective reaction of an unprotected synthetic peptide-alpha-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Baggiolini et al. (1992) *FEBS Lett.* 307: 97-101; Clark-Lewis et al., *J. Biol. Chem.*, 269:16075 (1994); Clark-Lewis et al., *Biochemistry*, 30:3128 (1991); Rajarathnam et al., *Biochemistry* 33:6623-30 (1994)).

Alternatively, unprotected peptide segments are chemically linked where the bond formed between the peptide segments as a result of the chemical ligation is an unnatural (non-peptide) bond (Schnolzer, M et al. *Science*, 256:221 (1992)). This technique has been used to synthesize analogs of protein domains as well as large amounts of relatively pure proteins with full biological activity (deLisle Milton et al., *Techniques in Protein Chemistry* IV. Academic Press, New York, pp. 257-267 (1992)).

Provided are fragments of antibodies which have bioactivity. The polypeptide fragments of the provided method can be recombinant proteins obtained by cloning nucleic acids encoding the polypeptide in an expression system capable of producing the polypeptide fragments thereof, such as an adenovirus or baculovirus expression system. For example, one can determine the active domain of an antibody from a specific hybridoma that can cause a biological effect associated with the interaction of the antibody with IL-13 or fragment thereof (e.g., IL13RBM), or soluble IL-13 receptor (e.g., IL-13Rα, or IL-13Rα2) or fragment thereof. For example, amino acids found to not contribute to either the activity or the binding specificity or affinity of the antibody can be deleted without a loss in the respective activity. For example, in various embodiments, amino or carboxy-terminal amino acids are sequentially removed from either the native or the modified non-immunoglobulin molecule or the immunoglobulin molecule and the respective activity assayed in one of many available assays. In another example, a fragment of an antibody comprises a modified antibody wherein at least one amino acid has been substituted for the naturally occurring amino acid at a specific position, and a portion of either amino terminal or carboxy terminal amino acids, or even an internal region of the antibody, has been replaced with a polypeptide fragment or other moiety, such as biotin, which can facilitate in the purification of the modified antibody. For example, a modified antibody can be fused to a maltose binding protein, through either peptide chemistry or cloning the respective nucleic acids encoding the two polypeptide fragments into an expression vector such that the expression of the coding region results in a hybrid polypeptide. The hybrid polypeptide can be affinity purified by passing it over an amylose affinity column, and the modified antibody receptor can then be separated from the maltose binding region by cleaving the hybrid polypeptide with the specific protease factor Xa. (See, for example, New England Biolabs Product Catalog, 1996, pg. 164.). Similar purification procedures are available for isolating hybrid proteins from eukaryotic cells as well.

The fragments, whether attached to other sequences or not, include insertions, deletions, substitutions, or other selected modifications of particular regions or specific amino acids residues, provided the activity of the fragment is not significantly altered or impaired compared to the nonmodified antibody or antibody fragment. These modifications can provide for some additional property, such as to remove or add amino acids capable of disulfide bonding, to increase its bio-longevity, to alter its secretory characteristics, etc. In any case, the fragment must possess a bioactive property, such as binding activity, regulation of binding at the binding domain, etc. Functional or active regions of the antibody can be identified by mutagenesis of a specific region of the protein, followed by expression and testing of the expressed polypeptide. Such methods are readily apparent to a skilled practitioner in the art and can include site-specific mutagenesis of the nucleic acid encoding the antigen. (Zoller et al. *Nucl. Acids Res.* 10:6487-500 (1982).

A variety of immunoassay formats can be used to select antibodies that selectively bind with a particular protein, variant, or fragment. For example, solid-phase ELISA immunoassays are routinely used to select antibodies selectively immunoreactive with a protein, protein variant, or fragment thereof. See Harlow and Lane. (*Antibodies, A Laboratory Manual*. Cold Spring Harbor Publications, New York, (1988)), for a description of immunoassay formats and conditions that could be used to determine selective binding. The binding affinity of a monoclonal antibody can, for example, be determined by the Scatchard analysis of Munson et al., (*Anal. Biochem.*, 107:220 (1980).

Also provided is an antibody reagent kit comprising containers of the monoclonal antibody or fragment thereof of provided method and one or more reagents for detecting binding of the antibody or fragment thereof to IL-13 or fragment thereof (e.g., IL13RBM), or soluble IL-13 receptor (e.g., IL-13Ra, or IL-13Rα2) or fragment thereof receptor molecule. The reagents can include, for example, fluorescent tags, enzymatic tags, or other tags. The reagents can also include secondary or tertiary antibodies or reagents for enzymatic reactions, wherein the enzymatic reactions produce a product that can be visualized.

Screening Methods/Product-by-Process

The substance of the provided method can comprise a molecule capable of blocking the binding of IL-13 to IL-13 receptor on NKT cells, wherein the molecule is produced by the process of 1) contacting NKT cells that express IL-13 receptor with the molecule, 2) assaying the cell for the ability of IL-13 to bind the NKT cells contacted with the molecule, and 3) producing the molecule. Also provided herein is a molecule produced by this process.

Also provided is a method of screening for a substance capable of blocking the binding of IL-13 to IL-13 receptors on NKT cells, comprising: a) contacting NKT cells that express IL-13 receptor with a candidate molecule, b) assaying the cell for the ability of endogenous IL-13 to bind the NKT cells contacted with the molecule.

The ability of endogenous IL-13 to bind IL-13 receptors on NKT cells in vitro can be evaluated using standard methods known in the art, such as, for example, using two channel flow cytometric analysis to identify cells bearing both NKT cell markers (e.g., CD161) and IL-13 bound to IL-13 receptors, using antibodies conjugated with appropriate fluorochromes.

Also provided is a method of screening for a substance capable of blocking the binding of IL-13 to IL-13 receptor on NKT cells comprising: a) administering the substance to an animal having IBD; and b) assaying the animal for an effect on the ability of IL-13 to bind NKT cells that results in the reduction of the inflammatory response of the colitis.

Also provided is a method of screening for a substance capable of treating IBD (e.g. colitis or Crohn's disease) comprising a) administering the substance to an animal having IBD (e.g. colitis or Crohn's disease); b) assaying the animal for a reduction in IL-13 levels, a reduction in NKT cell levels or a reduction in binding of IL-13 to NKT cells, a reduction in any of these parameters indicating that the substance if capable of treating IBD.

The ability of a substance to reduce the inflammatory inducing effect of IL-13 can be determined by evaluating the histological and clinical manifestations, as set forth herein, of the animal with colitis before and after administration of the substance of interest and quantitating the amount of reduction of the inflammation. One of skill in the art can also determine if the substance reduces the number of NKT cells, as determined in lamina propia cells or PBM using methods standard in the art and those described herein One of skill in the art can also evaluate the inflammatory inducing effect of IL-13 by measuring the amount of IL-13 in inflammatory tissue. These methods include, but are not limited to, ELISA, PCR, FACS analysis, reverse-transcriptase-polymerase chain reaction and ELISPOT, Northern blots, Southern blots, and Western blots.

The animal in which the colitis is produced can be any mammal and can include but is not limited to mouse, rat, guinea pig, hamster, rabbit, cat, dog, goat, monkey, and chimpanzee. The colitis can be produced in the animal by any method known in the art. For example, the colitis can be produced by introducing into the colon of the animal an effective amount of a hapten reagent. As an example, the hapten reagent can be trinitrobenzene sulfonic acid (TNBS) or oxazolone (4-ethoxymethylene-2-phenyl-2-oxazolin-5-one).

Th1-mediated colitis can be induced in mice using TNBS. Acute TNBS-colitis can be induced in SJL or C57BL10 mice using a single dose of TNBS. Briefly, 2.5 mg of TNBS (pH 1.5-2.0; Sigma Aldrich, St Louis, Mo.) in 50% ethanol is administered intrarectally in a total volume of 150 ul to lightly anesthetized mice. To establish a chronic model of TNBS colitis Balb/c are administered weekly dosages of TNBS per rectum in the following manner. Mice are administered 1.5 mg of TNBS (delivered in a 50% ethanol vehicle in a total volume of 150 ul) for weeks 1-2, 2.0 mg of TNBS for weeks 3-4, and 2.5 mg of TNBS for weeks 5-6.

Th2-mediated colitis can be induced in mice with oxazolone. Briefly, mice are presensitized by painting the skin with 0.2 mL 3% oxazolone in 100% ethanol; 5 days after presensitization mice are challenged intra-rectally with 150 µl 1% oxazolone in 50% ethanol under general anesthesia with isoflurane (Baxter, Deerfield, Ill.).

Method of Treating IBD

Provided herein is a method of treating or preventing inflammatory bowel disease (IBD) in a subject, comprising administering to the subject a therapeutic amount of a substance that modulates IL-13 activity. IBD includes both ulcerative colitis (UC) and Crohn's disease (CD). The fact that CD and UC differ from one another both clinically and pathologically suggests different immune processes in the two diseases. In particular, CD is marked by a transmural, granulomatous inflammatory process that is usually associated with Th1 immune responses; whereas UC is a more superficial disease in which epithelial damage is an over-riding factor, and autoantibodies are usually present that are generally markers of Th2 responses (Podolsky D K. (2002) N. Engl. J. Med. 347:417-429). These differences are also borne out by studies of the immune profiles in CD and UC that show that CD is associated with a predominant IL-12-directed IFN-γ response, a hallmark of a Th1 inflammation, whereas in UC this type of response is not present, and a Th2 IL-13 response appears to be driving the inflammation.

Despite the predominant Th1 response in CD, activated lamina propria $CD4^+$ T cells from patients with CD are shown herein to produce increased amounts of IL-13, however the increase is rather modest compared to that seen with cells from patients with UC. Furthermore, the cells producing IL-13 in CD are $CD4^+$ T cells (i.e., conventional T cells) whereas the cells producing IL-13 in UC are NKT cells. The latter is indicated by the fact that they produce IL-13 in response to stimulation by antigen-presenting cells that bear CD1d, a defining feature of NKT cells (Fuss et al. 2004. J. Clin: Invest. 113:1490-7).

In a chronic model of TNBS-colitis (i.e., a CD model), wherein TNBS is administered per rectum to BALB/c mice each week for as long as 6-8 weeks, the mice develop a chronic intestinal inflammation marked by colonic erythema and dilatation at the macroscopic level and transmural cell infiltration of the lamina propria at the microscopic level; however, the inflammation is lower in intensity than that observed in the acute model of TNBS-colitis and consequently the mice do not exhibit progressive weight loss and survive for long periods of time. Early in the course of this colitis, cells from the lamina propria of the mice produce large amounts of IFN-γ, indicating the presence of a Th1 T cell-mediated inflammation similar to that in acute TNBS-colitis and CD. However, at about 3-4 weeks after initiation of TNBS administration, the colonic cells begin to produce IL-23 and, concomitantly, begin to produce less IFN-γ and more IL-17. These cytokines are found in more chronic states of Th1 inflammations. Then, 4-5 weeks after initiation of TNBS administration, the cells begin to produce IL-13 and, a week later, TGF-β. At this point one begins to see the occurrence of fibrosis in the colonic lesions. However, if mice are administered IL-13Rα2-Fc, a substance that blocks the binding of IL-13 to its receptor, the mice do not produce TGF-β and do not develop fibrosis.

This model of colitis shows that IL-13 is not strictly associated with a Th2 T cell-mediated inflammation, and can occur along with a Th1 T cell-mediated inflammation. In addition, it shows that IL-13, through its induction of TGF-β, induces fibrosis. Further, the IL-13 production by cells from patients with CD is involved the fibrosis that occurs in this disease.

The provided method can be used to treat or prevent CD or UC. Thus, provided is a method of treating or preventing Crohn's disease in a subject, comprising administering to the subject a therapeutic amount of a substance that modulates IL-13 activity. In one aspect, the disclosed method can reverse or prevent the development of fibrosis in these subjects. Also provided is a method of treating or preventing ulcerative colitis in a subject, comprising administering to the subject a therapeutic amount of a substance that modulates IL-13 activity.

The substance that modulates IL-13 activity can be any such substance whether now known or later identified. In one aspect, the substance that modulates IL-13 activity can be any of the compositions described in WO2004001655 "METHODS OF TREATING AND PREVENTING COLITIS INVOLVING IL-13 AND NK-T CELLS," which is hereby incorporated herein by reference in its entirety for its teaching of IL-13 activity modulating agents. In another aspect, the substance that modulates IL-13 activity can be any of the herein disclosed substances that block the binding of IL-13 to IL-13 receptors on NKT cells. Thus, the substance of the present method can be a modified IL-13, such as a mutant IL-13 or a chimeric IL-13. Thus, provided herein is a method of treating or preventing ulcerative colitis or Crohn's disease in a subject, comprising administering to the subject a therapeutic amount of a mutant IL-13. Further provided is a method of treating or preventing ulcerative colitis in a subject, comprising administering to the subject a therapeutic amount of an IL-13 receptor binding molecule (IL13RBM) linked to an effector molecule. The effector molecule can be any effector molecule provided herein.

Delivery of Effector to NKT

Disclosed herein is the expression of IL-13 receptors on NKT cells in the ulcerative colitis gut. Thus, provided is a method of specifically delivering an effector molecule to an NKT cell to treat UC. The method can comprise linking the effector molecule to an IL13RBM and delivering to the cell an effective amount of the IL13RBM-linked effector molecule. For the treatment or prevention of UC, the NKT cell is located in the gut of a subject with ulcerative colitis.

The term "specifically deliver" as used herein refers to the preferential association of a molecule with a cell or tissue bearing a particular target molecule or marker and not to cells or tissues lacking that target molecule. It is, of course, recognized that a certain degree of non-specific interaction can occur between a molecule and a non-target cell or tissue. Nevertheless, specific delivery can be distinguished as mediated through specific recognition of the target molecule. Typically specific delivery results in a much stronger association between the delivered molecule and cells bearing the target molecule than between the delivered molecule and cells lacking the target molecule.

The IL13RBM of the provided method can be a native or modified IL-13, such as for example human IL-13, mutant human IL-13, or a fragment thereof, or the IL13RBM can be a soluble IL-13 receptor (e.g., IL-13Rα, or IL-13Rα2) or fragment thereof. The effector molecule can be conjugated to the IL13RBM or the IL13RBM-linked effector molecule can be a fusion protein. The effector molecule of the provided method can either enhance or inhibit the activity of the NKT cell. The effector molecule can be any effector molecule disclosed herein. In one aspect, the effector molecule is a cytotoxin, a label, a radionuclide, a drug, a liposome, or an antibody. For example, the effector molecule can be *Pseudomonas* exotoxin PE35, PE38, PE38 KDEL, PE40, PE4E, or PE38QQR.

Administration

The substances provided herein can be administered in a number of ways depending on whether local or systemic treatment is desired, and on the area to be treated. The disclosed substances can be administered, for example, intravenously, mucosally, by inhalation, intranasally, intrarectally, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, antioxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like can be necessary or desirable.

Compositions for oral administration include powders or granules, suspensions or solutions in water or non-aqueous media, capsules, sachets, or tablets. Thickeners, flavorings, diluents, emulsifiers, dispersing aids dr binders can be desirable.

Some of the compositions can potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Dose

The substances provided herein can be delivered at effective amounts or concentrations. An effective concentration or amount of a substance is one that results in treatment or prevention of the inflammatory response of IBD. Effective dosages and schedules for administering the provided substance can be determined empirically, and making such determinations is within the skill in the art. Those skilled in the art will understand that the dosage of the provided substances that must be administered will vary depending on, for example, the subject that will receive the substance, the route of administration, the particular type of substance used and other drugs being administered. One of skill in the art can utilize in vitro assays to optimize the in vivo dosage of a particular substance, including concentration and time course of administration.

The dosage ranges for the administration of the substances are those large enough to produce the desired effect in which the symptoms of the disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary, and can be administered in one or more dose administrations daily, for one or several days.

For example, guidance in selecting appropriate doses when the provided substance is an antibody is found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389.

A typical daily dosage of the provided substance might range from about 1 μg/kg to up to 100 mg/kg of body weight or more per day, depending on the factors mentioned above. In one aspect, treatment can consist of a single/daily dosage of 1 mg to 20 mg/kg of body weight of a substance provided herein. In another aspect, the substance is infused during a period from 10 minutes to 48 hours. As another example, soluble receptors and antibodies provided herein can be administered at 1, 2, 3, 4, 5, 6, 7, 8, 9, or 10 mg/kg. As another example, modified IL-13 comprising cytotoxins can be administered at 1, 10, 100, 200, 300, 400, 500, 600, 700, 800, 900, or 1000 µg/kg. As another example, mutant IL-13 can be administered at 1 to 10 µg/kg.

The blood pressure, pulse and temperature of the subjects can be monitored prior to and at 30 minute intervals during the two hour infusion period. Subjects can be given a laboratory evaluation consisting of a complete blood count (CBC) with differential, platelet count, SMA-18 chemistry profile, erythrocyte sedimentation rate (ESR) and a C-reactive protein assay at 1) the time of infusion; 2) 24 hours after infusion; 3) 72 hours after infusion; 4) two weeks after the last infusion; 5) four weeks after the last infusion; (6) six weeks after the last infusion; and 7) eight weeks after the last infusion.

Subjects can also undergo routine colonoscopy with video surveillance at the time of the infusion of a substance provided herein and again at two, four, six and eight weeks after the last infusion. Additionally, serum samples from the subjects can be assayed by ELISA for IL-13 activity and/or NKT cell activity levels to monitor drug efficacy. Also, tissue biopsy samples obtained during colonoscopy can be cultured for purified, isolated lamina propia cells and assayed as well. Purified PBM can also be isolated, cultured and assayed.

For example, to evaluate the efficacy of treatment of humans with a disorder characterized by colitis, such as for example, ulcerative colitis, with a substance that modulates IL-13 activity, the following studies can be performed. Patients with active inflammation of the colon and/or the terminal ileum who have failed standard medical therapy, which can include prednisone and/or other immunomodulators known in the art (parenterally or orally) for control of the disorder can be selected. Drug efficacy can be monitored via colonoscopy. Patients can be randomized to two different protocols. In one protocol, subjects can remain on initial medication and in the second protocol, subjects can have their medication tapered after receiving the substance that modulates IL-13 activity.

Following administration of a substance for treating, inhibiting, or preventing IBD, the efficacy of the therapeutic substance can be assessed in various ways well known to the skilled practitioner. For instance, one of ordinary skill in the art will understand that a substance provided herein is efficacious in treating or inhibiting inflammation of an established IBD in a subject by observing that the substance reduces inflammation or prevents a further increase in inflammation. Inflammation can be measured by methods that are known in the art, for example, using tissue biopsies to assess tissue damage or antibody assays to detect the presence of inflammatory cytokines in a sample (e.g., bodily fluids, but not limited to, blood) from a subject or patient, or by measuring the cytokine levels in the patient. Efficacy of the treatment can also be determined by measuring the number of NKT cells in the subject (e.g. in the colon or peripheral blood) with inflammation from IBD. A treatment that inhibits an initial or further increase in NKT cells or IL-13 levels in a subject or patient with inflammation of an established IBD, or that results in a decrease in the number of NKT cells or IL-13 levels in a subject or patient with inflammation of an established colitis, is an efficacious treatment.

The substances provided herein can be administered prophylactically to patients or subjects who are at risk for having IBD or who have been newly diagnosed with IBD. In subjects who have been newly diagnosed with IBD but who have not yet displayed an established colitis or the inflammatory response of an established colitis (as measured by biopsy or other assays for detecting the inflammation due to colitis) in blood or other body fluid, efficacious treatment with an substance provided herein partially or completely inhibits the appearance of IBD symptoms and/or onset of UC or CD.

Co-administration

Also disclosed are methods for the treatment or prevention of the inflammatory response of IBD comprising co-administering any of the herein provided substances with another therapeutic agent. Other therapeutic agents can include, but are not limited to, antibodies, such as an anti-IL-4 antibody, cytokines, or immunomodulatory agents.

Examples of these cytokines, antibodies and immunomodulatory agents that can be employed in the methods provided herein include, but are not limited to, Azathioprine, 6-mercaptopurine, methotrexate, WIG, antisera against lymphocyte membrane antigens (i.e. antithymocyte serum (ATS), antithymocyte globulin (ATG), antilymphocyte serum (ALS), antilymphocyte globulin (ALG), anti-CD3, anti-CD4, anti-CD8)), anti-TNFα, anti-IFNγ, antisense STAT4 oligonucleotides, anti-ICAM1, antisense ICAM-1 oligonucleotides, anti-CD40L, anti-CD25 (anti-Tag), and IL-10. Other cytokines, antibodies and/or immunomodulators can be administered according to the methods of provided herein both to treat an acute episode of disease or to maintain the subject's condition in a non-inflammatory state.

Nucleic Acid Approaches for Delivery

The substances of the provided method can also be administered in vivo and/or ex vivo to patients or subjects as a nucleic acid preparation (e.g., DNA or RNA) that encodes a substance, such that the patient's or subject's own cells take up the nucleic acid and produce and secrete the encoded substances. Thus, the substance of the provided method can comprise an isolated nucleic acid encoding a modified IL-13, as disclosed herein.

Nucleic acids can be in the form of naked DNA or RNA, or the nucleic acids can be in a vector for delivering the nucleic acids to the cells, whereby the nucleic acid is under the transcriptional regulation of a promoter, as would be well understood by one of ordinary skill in the art. Thus, the substance of the provided method can comprise a vector comprising a nucleic acid encoding a modified IL-13, as disclosed herein.

The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector provided herein can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

As one example, vector delivery can be via a viral system, such as a retroviral vector system which can package a recombinant retroviral genome (see e.g., Pastan et al., *Proc. Natl. Acad. Sci. U.S.A.* 85:4486, 1988; Miller et al., *Mol. Cell. Biol.* 6:2895, 1986). The recombinant retrovirus can then be used to infect and thereby deliver to the infected cells nucleic acid encoding, for example, a modified IL-13. The exact method of introducing the altered nucleic acid into mammalian cells is, of course, not limited to the use of retroviral vectors. Other techniques are widely available for this procedure including the use of adenoviral vectors (Mitani et al., *Hum. Gene Ther.* 5:941-948, 1994), adeno-associated viral (AAV) vectors (Goodman et al., *Blood* 84:1492-1500, 1994), lentiviral vectors (Naidini et al., *Science* 272:263-267, 1996), and pseudotyped retroviral vectors (Agrawal et al., *Exper. Hematol.* 24:738-747, 1996). Physical transduction techniques can also be used, such as liposome delivery and receptor-mediated and other endocytosis mechanisms (see, for example, Schwartzenberger et al., *Blood* 87:472-478, 1996) to name a few examples. This method can be used in conjunction with any of these or other commonly used gene transfer methods.

As one example, provided nucleic acid is delivered to the cells of a subject in an adenovirus vector, the dosage for administration of adenovirus to humans can range from about $10^7$ to $10^9$ plaque forming units (pfu) per injection but can be as high as $10^{12}$ pfu per injection (Crystal, *Hum. Gene Ther.* 8:985-1001, 1997; Alvarez and Curiel, *Hum. Gene Ther.* 8:597-613, 1997). A subject can receive a single injection, or, if additional injections are necessary, they can be repeated at six month intervals (or other appropriate time intervals, as determined by the skilled practitioner) for an indefinite period and/or until the efficacy of the treatment has been established.

Parenteral administration of the provided nucleic acid or vector, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein. For additional discussion of suitable formulations and various routes of administration of therapeutic compounds, see, e.g., *Remington: The Science and Practice of Pharmacy* (19th ed.) ed. A. R. Gennaro, Mack Publishing Company, Easton, Pa. 1995.

Pharmaceutically Acceptable Carriers

The substances provided herein, can be used therapeutically in combination with a pharmaceutically acceptable carrier. By "pharmaceutically acceptable" is meant a material that is not biologically or otherwise undesirable, i.e., the material can be administered to a subject, along with the substance, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions can include carriers, thickeners, diluents, buffers, preservatives, surface active agents and the like in addition to the molecule of choice. Pharmaceutical compositions can also include one or more active ingredients such as antimicrobial agents, anti-inflammatory agents, anesthetics, and the like.

Suitable carriers and their formulations are described in *Remington: The Science and Practice of Pharmacy* ((19th ed.) ed. A. R. Gennaro, Mack Publishing Company, Easton, Pa. 1995). Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers can be more preferable depending upon, for instance, the route of administration and concentration of substance being administered.

Compositions Identified by Screening with Disclosed Compositions/Combinatorial Chemistry/Computer Assisted Drug Design The disclosed compositions, such as IL-13 or fragment thereof (e.g., IL13RBM), or soluble IL-13 receptor (e.g., IL-13Rα, or IL-13Rα2) or fragment thereof, can be used as targets for any molecular modeling technique to identify either the structure of the disclosed compositions or to identify potential or actual molecules, such as small molecules, which interact in a desired way with the disclosed compositions.

It is understood that when using the disclosed compositions in modeling techniques, molecules, such as macromolecular molecules, will be identified that have particular desired properties such as inhibition or stimulation of the target molecule's function. The molecules identified and isolated when using the disclosed compositions, such as IL-13 or fragment thereof (e.g., IL13RBM), or soluble IL-13 receptor (e.g., IL-13Rα, or IL-13Rα2) or fragment thereof, are also disclosed. Thus, the products produced using the molecular modeling approaches that involve the disclosed compositions, such as, IL-13 or fragment thereof (e.g., IL13RBM), or soluble IL-13 receptor (e.g., IL-13Rα, or IL-13Rα2) or fragment thereof are also considered herein disclosed.

Thus, one way to isolate molecules that bind a molecule of choice is through rational design. This is achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159-166; Ripka, *New Scientist* 54-57 (Jun. 16, 1988); McKinaly and Rossmann, 1989 *Annu. Rev. Pharmacol. Toxiciol.* 29, 111-122; Perry and Davies, *QSAR: Quantitative Structure-Activity Relationships in Drug Design* pp. 189-193 (Alan R. Liss, Inc. 1989); Lewis and Dean, 1989 *Proc. R. Soc. Lond.* 236, 125-140 and 141-162; and, with respect to a model enzyme for nucleic acid components, Askew, et al., 1989 *J. Am. Chem. Soc.* 111, 1082-1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of molecules specifically interacting with specific regions of DNA or RNA, once that region is identified.

Although described above with reference to design and generation of compounds which could alter binding, one could also screen libraries of known compounds, including natural products or synthetic chemicals, and biologically active materials, including proteins, for compounds which alter binding specificity for IL-13 or any other composition described herein.

Compositions with Similar Functions

It is understood that the compositions disclosed herein have certain functions, such as binding IL-13Rα or IL-13Rα2. Disclosed herein are certain structural requirements for performing the disclosed functions, and it is understood that there are a variety of structures which can perform the same function which are related to the disclosed structures, and that these structures will ultimately achieve the same result, for example inhibition of the binding of IL-13 to NKT cells or the delivery of an effector molecule to an NKT cell.

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

EXAMPLES

Example 1

NKT Cells in IBD

A mouse model of oxazolone colitis was utilized to study Th2 cytokine production. In the Th2 model of oxazolone colitis, colitis is induced by the intra-rectal administration of the haptenating agent oxazolone in an ethanol vehicle. In this colitis, initial toxic effects of the inducing agent lead to a flooding of the lamina propria with bacterial antigens and thus the induction of an immune response that leads to further inflammation. The latter is driven by the production of Th2 cytokines since the inflammation is characterized by increased IL-4 and IL-5 secretion and the inflammation can be ameliorated by the administration of anti-IL-4 (Boirivant et al., 1998).

Oxazolone colitis is mediated by NKT cells capable of producing large amounts of Th2 cytokines when stimulated by either anti-CD3 or αGalCer. Initially, this consists of IL-4 secretion, which is rapidly superceded by IL-13 secretion. This IL-13 response originates from NKT cells responding to CD1-mediated antigen presentation and appears to be a key component of the inflammation, as neutralization of IL-13 prevents development of oxazolone colitis. Given the resemblance of oxazolone colitis in mice to ulcerative colitis in humans, these data indicate that similar treatment of human inflammatory disease would be effective.

Male C57Bl/10 mice were obtained from a breeding facility maintained by the National Cancer Institute (NCl, Bethesda, Md.) and were housed under specific pathogen free (SPF) conditions. 5 to 7 week old mice were used for all experiments. B6x129Sv-CD1 KO mice were received from Exley/Balk (Cui et al., 1997; Smiley et al., 1997), C57Bl/6-Ja281 KO mice were a generous gift from Dr. Taniguchi (Cui et al., 1997) bred at the animal facility at Brigham and Women's Hospital, Harvard Medical School, Boston, Mass. Oxazolone (4-Ethoxymethylene-2-Phenyl-2-Oxazoline-5-One) was obtained from Sigma-Aldrich (St. Louis, Mo.).

In order to presensitize mice a 2×2 cm field of the abdominal skin was shaved and 200 μl of a 3% (w/v) solution in 100% ethanol applied. 5 days after presensitization mice were rechallenged intra-rectally with 150 μl 1% Oxalone in 50% ethanol or only 50% ethanol (i.e. vehicle) under general anesthesia with isoflurane (Baxter, Deerfield, Ill.). Intra-rectal injection was administered with a polyurethane umbilical catheter (Sherwood, St. Louis, Mo.). Neutralization of IL-13 in vivo was performed with IL-13Rα2-Fc. Mice received 5×200 μg of control protein or IL-13Rα2-FcN starting on the day before presensitization i.v. and then every other day i.p. Depletion of NK1.1+ cells was achieved by injecting 250 μg anti-mouse NK1.1 monoclonal antibodies (clone PK136) i.v. 48 h before and after sensitization. Control mice received mouse IgG2a. FACS analysis of spleenocytes from treated animals showed that NK as well as NKT cells were completely depleted. Antigen presentation by CD1 molecules was blocked in vivo with anti-mouse CD1.1 (clone 20H2, gift from A. Bendelac) Mice were injected with 1 mg antibody every 2 days.

Mice were euthanized 5 days after induction of colitis. The colons were removed and segments fixed in formalin (Fisher, Fair Lawn, N.J.). After paraffin embedding 5 μm sections were cut and stained with Hematoxylin/Eosin (Lerner, New Haven, Conn.).

Splenocytes (SPC), mesenteric lymph node cells (MLNC) or lamina propria cells were isolated on day 2 or day 7 after colitis induction. Cells were isolated as described in detail in Current Protocols of Immunology (Scheiffele, 2002). In brief, LPMC were isolated after removal of epithelial cells by incubation of colon strips in HBSS/2.5 mMEDTA. Mononuclear cells were released by digesting the tissue in ISCOVES media supplemented with 10% FCS, 200 U/ml collagenase (Roche, Indianapolis, Ind.), 10 μg/ml DNAse 1 (Roche) and 1 μg/ml Gentamicin (BioWhittaker, Walkersville, Md.). Finally, leukocytes were separated from epithelial cells by centrifugation in a PERCOLL gradient (Amersham, Piscataway, N.J.) of 33% and 66%. MLN cells and spleenocytes were isolated by grinding the tissue in a petri dish and filtering the cell suspension through a 40 μm mesh. Spleen cells were treated with ACK lysis buffer to lyse red blood cells (Biosource, Camarillo, Calif.). Initially CD3 cells were isolated with mouse T-cell selection columns (R&D, Minneapolis, Minn.) according to the manufacturer's instructions. Purified CD4 cells were positively selected with CD4-beads and MACS mini columns (Miltenyi, Auburn, Calif.) according to the manufacturer's instructions. Cells were cultured in RPM1640 supplemented with 10% FCS, 20 mM HEPES, 5% NCTC, 2 mM Glutamine, 50 µg/mlPenicillin/Streptomycin, 50 µg/ml Gentamicin, 50 µM 2-mercaptoethanol, and 50 U rhu IL-2. T cells were stimulated in vitro with plate bound anti-CD3 (10 µg/ml 2C11, Pharmingen, San Diego, Calif.) and soluble anti-CD28 (1 µg/ml clone 37.51, Pharmingen). To stimulate lymphocytes with αGalCer a fibroblast cell line (L-929) transfected with mouse CD1 as antigen presenting cells was used. L-cells were treated for 1.5 h with Mitomycin C and seeded at $1 \times 10^5$ cells/ml. αGalactosyl-Ceramide (αGalCer;Kirin, Tokyo, Japan) or vehicle was added at 100 ng/ml. Lymphocyte concentration was generally $1 \times 10^6$ cells/ml. After 48 h culture, supernatants were harvested and stored at $-20°$ C. until further analysis. IL-4 and IL-5 were measured with OptEIA ELISA sets from Pharmingen. IL-13 was measured with a Quantikine M ELISA kit from R&D (Minneapolis, Minn.).

Cells were stained with antibodies to CD3 (2C11), CD4 (RM4-5), NK1.1 (PK136), Ly49C (5E6), Ly6C (AL-21), and DX5 after incubation with FpBlock (2.4G2) (all BD Pharmingen). Surface staining was analyzed on a FACScanner (Becton-Dickinson, Mansfield, Mass.). Relative numbers were calculated with CellQuest software after gating on living lymphocytes in the scatter diagram.

Figure 2:
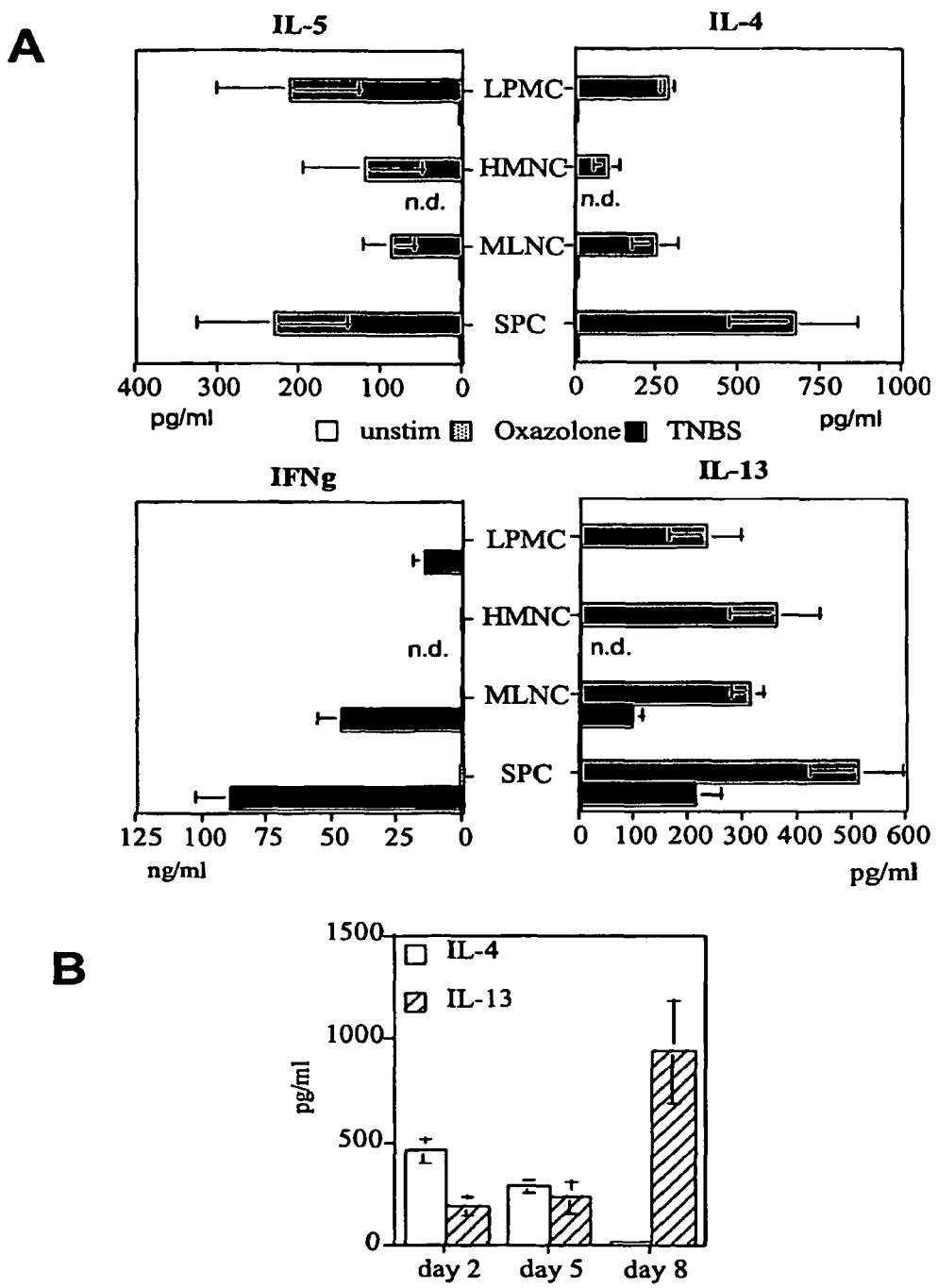
FIGS. 2A-B show cytokine production from lymphocytes from mice with oxazolone colitis. (A) Lamina propria mononuclear cells (LPMC), hepatic mononuclear cells (HMNC), mesenteric lymph node cells (MLNC) and splenocytes (SPC) were isolated on day 5 after induction of oxazolone colitis (gray) or acute TNBS (black) colitis and stimulated in vitro for 48 h with plate-bound anti-CD3 and anti-CD28. Cytokine concentrations were measured in supernatants by ELISA. (B) LPMC were isolated on day 2, 5 or 8 after induction of oxazolone colitis. LPMC were stimulated as above, and the concentrations of IL-4 (open) and IL-13 (striped) measured in the supernatants. A very small amount of IL-13 is produced by LPMC, MLNC, or SPC in the acute model of TNBS-colitis. However, as described below, a much greater production of IL-13 is observed in a chronic model of TNBS in BALB/c mice.

To obtain a more long-lived, chronic inflammatory response on the oxazolone colitis mouse model, mice were presensitized with 3% oxazolone by skin painting 5 days before rectal challenge and then injected intrarectally 1% oxazolone to induce colitis. As shown in FIG. 1A, only pre-sensitized mice developed colitis and progressive weight loss, whereas naïve animals did not develop any inflammation. In addition, as shown in FIG. 1B, the colitis induced in this case led to a chronic progressive wasting and weight loss so that after 7-10 days most animals had lost 40% of their initial body weight and were moribund. Histological examination of the colon at days 7-10 showed a massive bowel wall edema and infiltration by leukocytes. The superficial layers of the mucosa show dense infiltrations with small polynuclear granulocytes and large ulcerations interrupting the layer of enterocytes are present. As shown in FIG. 1D+E, this histopathological picture is similar to that seen in human ulcerative colitis, indicating that a similar pathological mechanism contributes to tissue damage in both inflammations. Finally, as shown in FIG. 2A, mononuclear cells isolated from the lamina propria (LPMC), mesenteric lymph nodes (MLNC), or spleen (SPC), and then stimulated with anti-CD3/anti-CD28 in vitro produced large amounts of Th2 cytokines (IL-4, IL-5, IL-13) but only low levels of IFN-γ. On the contrary LPMC isolated from mice with TNBS colitis produce undetectable levels of IL-4 and IL-5, and only low levels of IL-13, but very high amounts of TNFα.

Figure 3:
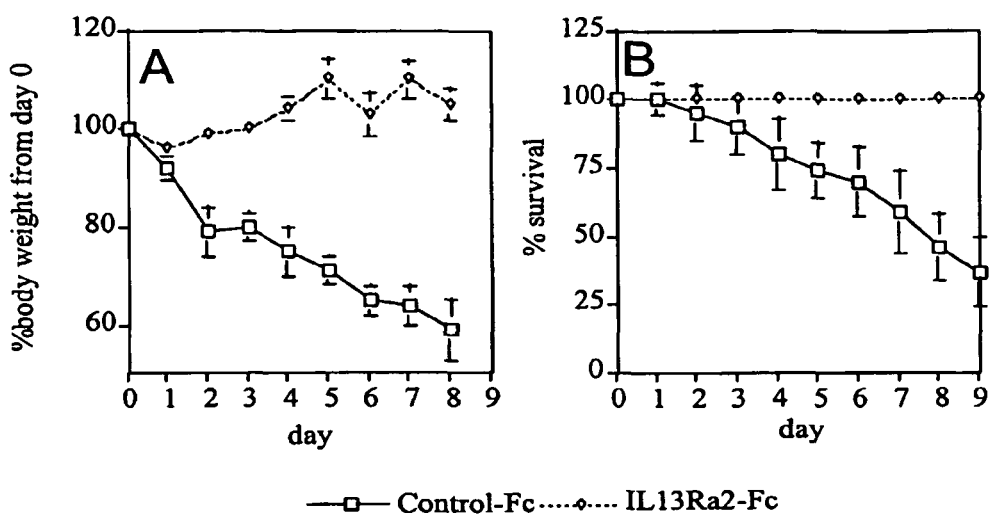
FIGS. 3A-B show that neutralization of IL-13 prevents induction of oxazolone colitis. (A) Weight loss and (B) mortality from mice with oxazolone colitis treated with IL-13Rα2-Fc (diamonds) or control-protein (squares).
Figure 15:
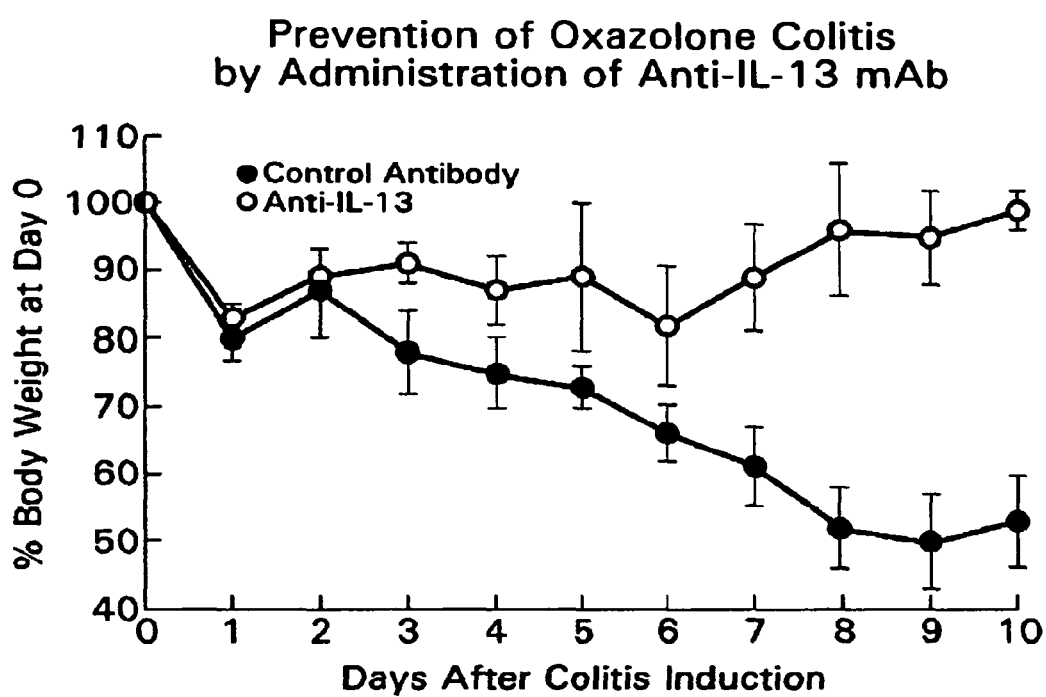
FIG. 15 shows weight curves of mice administered Oxazolone per rectum on Day 0 and injected with anti-IL-13 mAB (500 ug IP) or control antibody of the same Ig isotype on Days 0, 1 and 3.

IL-4 production by LPMC isolated at different time points during the course of oxazolone colitis gradually decreased. In contrast, IL-13 production by LPMC (as well as MLMC or spleen MC) during the same timeframe increased (FIG. 2B). This phenomenon has been observed in other animal models mediated by Th2 cells (Minty et al., 1997; Urban et al., 1998). To establish a pathogenic role for IL-13 in oxazolone colitis, IL-13 was neutralized by in vivo administration of IL-13Rα2 fused to the Fc portion of human IgG1 (IL-13Rα2-Fc) at the time of intra-rectal oxazolone administration. The α2 chain of the IL-13 receptor has a 100 fold higher affinity to IL-13 than the α1 chain, but only the latter transmits an intracellular signal after engagement. The IL-13Rα2-Fc fusion protein binds IL-13 and has been shown to neutralize IL-13 bioactivity in vivo (Donaldson et al., 1998). As shown in FIG. 3, mice treated with IL-13Rα2-Fc were protected from induction of oxazolone colitis: after an initial transient weight loss similar to that seen with ethanol alone, they regained their initial body weight by day 3 and on day 5 colonic histology was indistinguishable from that of mice that were given ethanol alone. Likewise, as shown in FIG. 15, mice treated with anti-IL13 monoclonal antibodies (500 ug IP) maintained initial body weight after oxazolone colitis induction as compared to that of mice that were given isotype control IgG.

Figure 4:
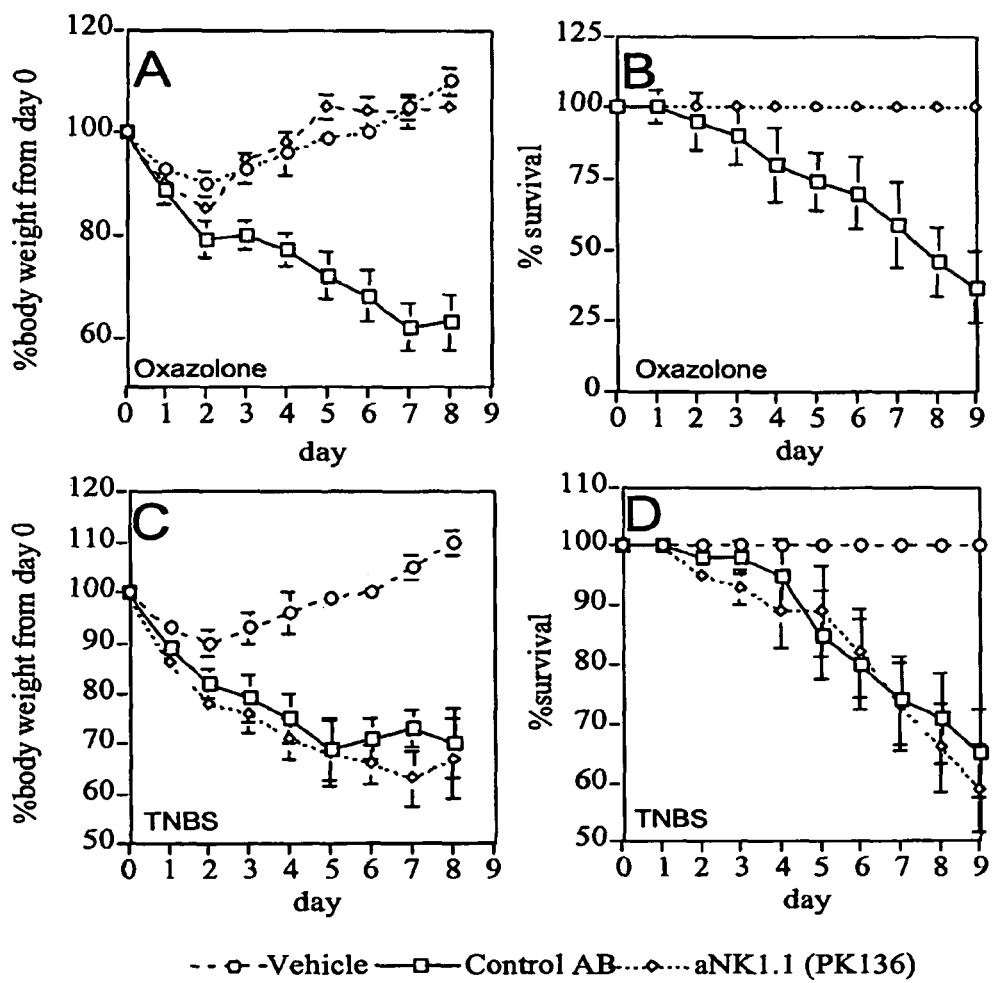
FIGS. 4A-D show that depletion of NK1.1 lymphocytes protects mice from oxazolone colitis but not TNBS colitis. Weight loss (A+C) and mortality (B+D) after induction of oxazolone colitis (A+B) or TNBS colitis (C+D) or injection of vehicle (ethanol; circles). Mice were injected wih control antibody (squares) or depleted of NK1.1 cells with PK136 (diamonds).

As alluded to above, mononuclear cells isolated from mice with oxazolone colitis produce increased amounts of IL-13 in vitro when stimulated with anti-CD3 and anti-CD28. However, when these mononuclear cells were purified by a negative selection column to enrich for CD3-positive cells, this stimulation led to greatly decreased IL-13 production. Since the selection column contains glass beads coated with anti-mouse IgG, it retains cells that express Fc-receptors (CD16 or CD32) and are coated with immunoglobulins; thus it was possible that IL-13 production by anti-CD3-stimulated LPMC in oxazolone colitis requires an Fc-receptor-positive cell. In addition to mast cells and B-lymphocytes, NK and NKT cells express CD16 (Koyasu, 1994) and are capable of producing IL-13 (Terabe et al., 2000). To investigate if either of the latter two cell types is involved, mice were depleted of NK1.1 cells by repeated injection of monoclonal anti-NK1.1 antibody (PK136) before challenge with oxazolone. Such treatment depleted all NK and NKT cells, as determined by DX5 and NK1.1 staining of splenocytes. As shown in FIG. 4A+B, it was found that depleted mice did not develop weight loss or macroscopic/microscopic evidence of colonic inflammation and did not manifest increased Th2 cytokine production after intra-rectal challenge with oxazolone.

In further studies to determine if this pathogenic role for NK1.1 positive cells is specific for oxazolone colitis, NK1.1-depleted C57Bl/10 mice were compared with untreated C57Bl/10 mice in their susceptibility to TNBS-colitis, a Th1 model of colitis resembling human Crohn's disease. As shown in FIG. 4C+D, depletion of NK1.1+ cells does not significantly influence weight loss or mortality of mice with TNBS colitis, and notably, there was a trend to higher weight loss in depleted mice. These results suggest that cells bearing NK1.1 in the mucosa play, if anything, an inhibitory role for the induction of a Th1 inflammation in TNBS-colitis, an effect previously noted in other models of Th1-mediated intestinal inflammations (Saubermann et al., 2000).

Whereas the above studies show that oxazolone colitis is mediated by NK1.1-positive cells they do not provide information on whether the latter cells are NK cells or NKT cells, as NK1.1 is present on both of these cell types. To address this issue, whether oxazolone colitis was affected by blockade of antigen presentation by CD1 molecules which affects activation of NKT cells but not the activation of NK cells was examined. This was accomplished by administration of a monoclonal anti-CD1 antibody that has been shown to block CD1 in vivo without depleting NKT cells and without affecting antigen-presentation by MHC class II (Park et al., 1998). As shown in FIG. 5, administration of this antibody at the time of intra-rectal oxazolone administration prevented development of oxazolone colitis.

As shown in FIG. 5B, these results were confirmed with studies of CD1-KO mice, in which it was shown that intra-rectal administration of oxazolone to pre-sensitized mice do not develop colitis nor a colonic Th2 response. Despite the absence of NKT cells the CD1-KO mice have been shown to be fully capable of mounting Th2 responses (Smiley et al., 1997). Thus, this result cannot be attributed to an intrinsic failure of the CD1 KO to mount a Th2 response.

Finally it was found that Ja281 KO mice are resistant to the induction of oxazolone colitis (FIG. 5B). While most CD1 restricted NKT cells utilize the canonical Val4Ja281TCR, some results suggested the existence of NKT cells with other TCRs. These "atypical" NKT cells are present in the Ja281-KO mouse, but proved to be insufficient to induce an inflammatory response. Taken together, data from the antibody-treated and KO mice show that oxazolone colitis is dependent on the induction of T cells by CD1-restricted antigens and that the T cells are NK1.1+Ja281+CD16+CD4+ cells.

In further studies whether or not NKT cells infiltrate the lamina propria of mice with oxazolone colitis was determined. However, this goal is made difficult by the fact that whereas NK1.1 is a frequent marker of NKT cells, T cells with NKT cell function have also been identified in the NK1.1-negative population. In addition, most NKT cell markers are dependent on the levels of cell activation. Thus, NKT cells lose their expression of NK1.1 upon activation (Chen and Paul, 1997) and another NK/NKT cell marker, Ly49C, is upregulated in activated NKT cells. Beside activation, NKT cells from different tissues co-express different surrogate markers of NK cell function together with the TCR. With these limitations in mind, it was found that during the course of oxazolone colitis total lymphocyte numbers expand significantly in the lamina propria (~10-fold), liver (~6 fold), mesenteric lymph nodes (~50 fold) and spleen (~2 fold). Moreover, in the lamina propria and in the liver the relative number of NKT cells expands in relation to other cell populations. Thus, in the lamina propria from untreated mice 7% (NK1.1) or 0.4% (Ly49C) of the T cells co-express an NKT cell marker. After induction of oxazolone colitis 21% of the infiltrating T-cells are NK1.1 positive and 34% are Ly49C positive. In the liver, where the highest percentage of NKT cells can be found, NK1.1 expression on CD3 positive cells increases from 9.9% to 48% of cells, while Ly49C expression is low. For unknown reasons, NKT cells are absent from mesenteric lymph nodes even after colitis induction: at this site, less than 1% of the cells can be identified as NKT cells. Finally, in the spleen of untreated mice 3.1% of CD3-positive cells are NK1.1+, and after induction of oxazolone colitis 5.1% become NK1.1 positive, while the number of Ly49C+ cells increases from 0.6% to 28%. To summarize these findings, T cells with surrogate markers of NKT cell function expand in the lamina propria, the liver and the spleen.

Finally, to investigate the cytokine production of the LPMC and SPC in response to antigen presented by CD1, these cells were stimulated with αGalCer, a synthetic glycolipid that has been found to activate most NKT cell lines in a CD1-dependent fashion (Kawano et al., 1997). MHC-class II restricted T cells and NK cells are not affected by αGalCer; thus stimulation with αGalCer represents a way to assess NKT cell activation in unseparated cell mixtures. As shown in FIG. 6, when LPMC or SPC from mice with oxazolone colitis were stimulated with αGalCer they produced large amounts of Th2 cytokines, including very high amounts of IL-13. In addition, CD4-positive cells isolated by MACS from LPMC or SPC also responded to αGalCer with very high IL-13 production, indicating that many of the CD4+ cells in cell populations from mice with oxazolone colitis are CD1-restricted NKT cells.

In studies comparing Crohn's disease patients with ulcerative colitis patients, increased IL-13 production from lamina propia cells of ulcerative colitis patients was observed as compared to Crohn's disease patients. FACS data comparing the two groups also showing an increased number of NKT cells in the peripheral blood and lamina propria from ulcerative colitis patients as compared to Crohn's disease patients.

Example 2

Use of Modified IL-13 to Inhibit Ulcerative Colitis

A unique subset of inflammatory cells (natural killer T cells, or NKT cells) produce high levels of IL-13 in a mouse model of the human disease (oxazolone colitis) as well as in patients with UC. IL-13 is required for, or enhances, NKT cells' toxic effects, including their ability to lyse mucosal epithelial cells.

As disclosed herein, oxazolone colitis can be prevented by pretreatment with IL-13 inhibitors. These observations not only shed light on a previously unknown mechanism of this disease but also suggest the importance of developing anti-IL-13 strategies to treat UC. Disclosed herein is the use of two families of IL-13 antagonists for the treatment of UC. The IL-13 antagonist can be a mutant IL-13. As an example, IL-13E13K has a higher affinity for IL-13 receptor than native IL-13 but does not activate signaling in the receptor; it thus blocks the function of normal IL-13. The IL-13 antagonist can further comprise an IL-13 linked to an effector molecule. As an example, IL-13PE consists of IL-13 bound to *pseudomonas* toxin; it is thus capable of killing cells that bind IL-13 including the NKT cells mentioned above. Thus, these two families of molecules can be used to specifically disrupt inflammatory IL-13-mediated effects in UC.

Figure 7:
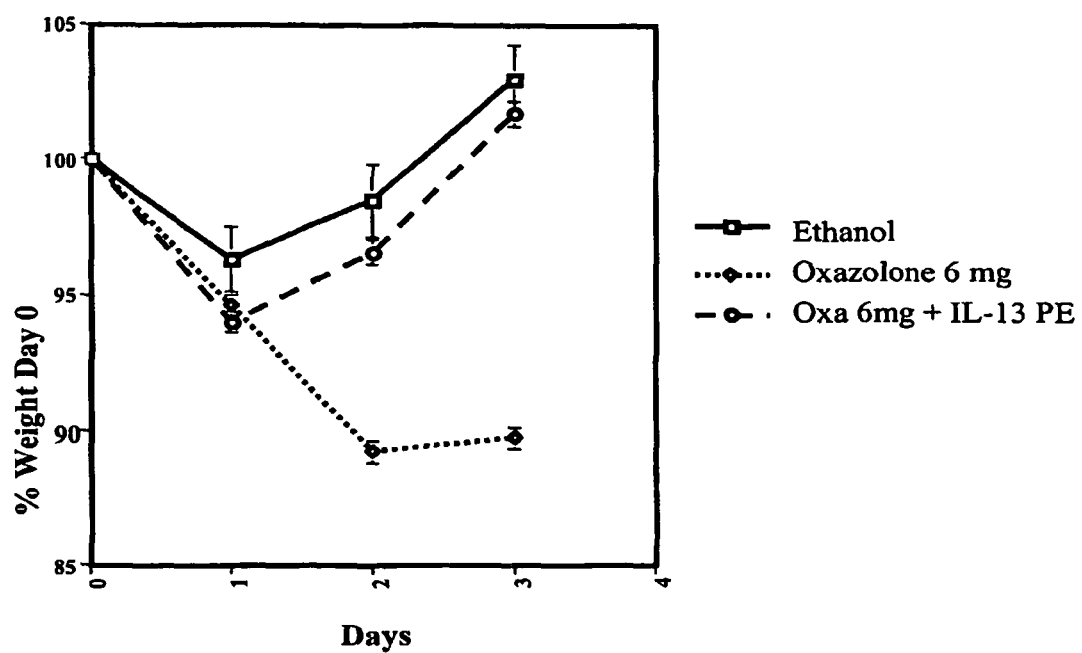
FIG. 7 shows a weight graph of Oxazolone colitis mice treated with an IL-13 *pseudomonas* toxin (IL13PE38).

FIG. 7 shows a weight graph for the experiments relating to treating Oxazolone colitis mice treated with an IL-13 *pseudomonas* exotoxin (IL-13PE38). There were 10 mice in each group. The groups consisted of ethanol treated alone, Oxazolone colitis mice, Oxazolone colitis mice treated with IL-13PE38. The colitis was induced by intrarectal injection of 6 mg of Oxazolone dissolved in 45% ethanol. Each mouse received 150 μl of this solution. Ethanol alone treated mice received 150 ul of 45% ethanol. Mice that received IL-13PE38 treatment received 5 μg of IL-13PE on Day −1 prior to Oxazolone administration, 5 μg on Day 0 and 5 μg on Day +1 of Oxazolone administration. As can be seen from the weight curves IL-13PE38 treated mice improved significantly in weight. Histological analysis of the colons also revealed little or no inflammation on Day 3 after Oxazolone administration.

Mice with oxazolone-induced colitis treated with IL-13PE demonstrated significantly less weight loss. In addition, cells in their mesenteric lymph nodes (MLN) secreted markedly less IL-13. MLN cells ($10^6$ cells) were stimulated with polyclonal stimuli consisting of anti-CD3/CD28. MLN cells from mice with oxazolone colitis not administered IL-13PE38 secreted 544 pg/ml in response to the stimuli, whereas cells from mice with oxazolone colitis treated with IL-13PE38 secreted 7 pg/ml in response to the stimuli.

Example 3

IL-13 in Chronic TNBS-Colitis

Figure 8:
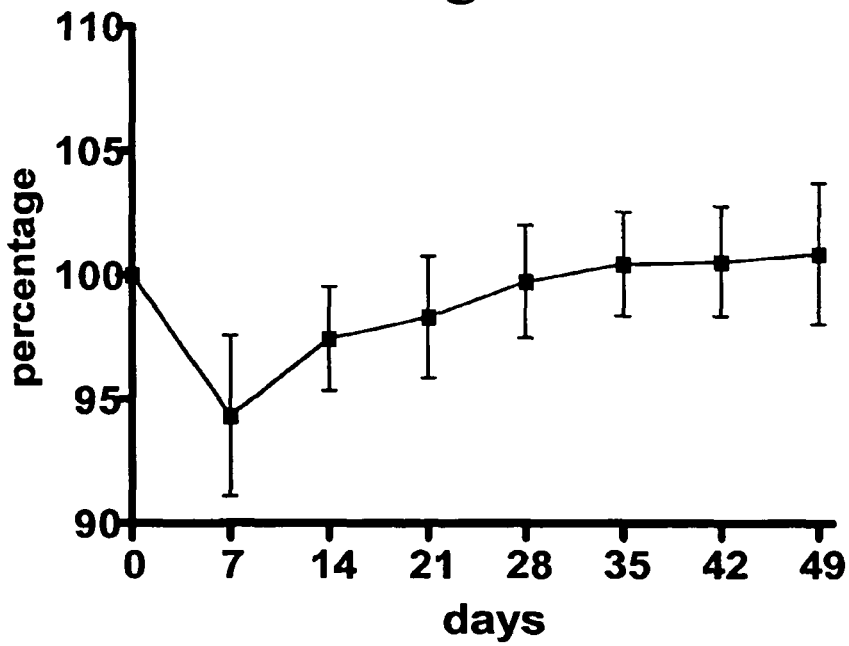
FIG. 8 shows a weight curve of Balb/c mice that received weekly intra-rectal administration of TNBS.

A chronic model of TNBS-colitis has been developed, wherein TNBS is administered per rectum to BALB/c mice each week for as long as 6-8 weeks. FIG. 8 shows a weight curve for mice during this administration. These mice develop a chronic intestinal inflammation marked by colonic erythema and dilatation at the macroscopic level and transmural cell infiltration of the lamina propria at the microscopic level; however, the inflammation is lower in intensity than that observed in the acute model of TNBS-colitis and consequently the mice do not exhibit progressive weight loss and survive for long periods of time.

Figure 9:
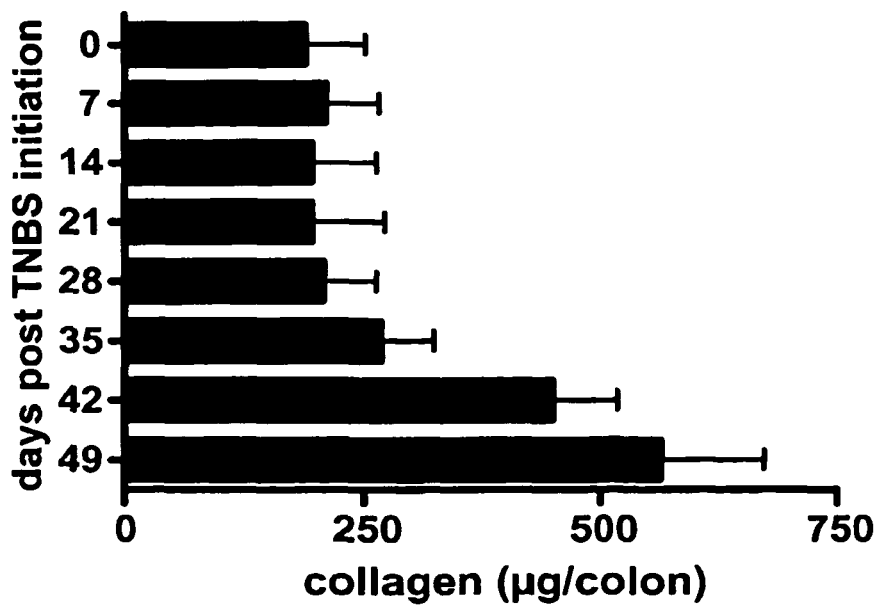
FIG. 9 shows collagen quantification from colon specimens. Chronic intestinal inflammation is established and increased amount of collagen formation is observed. Collagen formation coincides with the occurrence of fibrosis.
Figure 10:
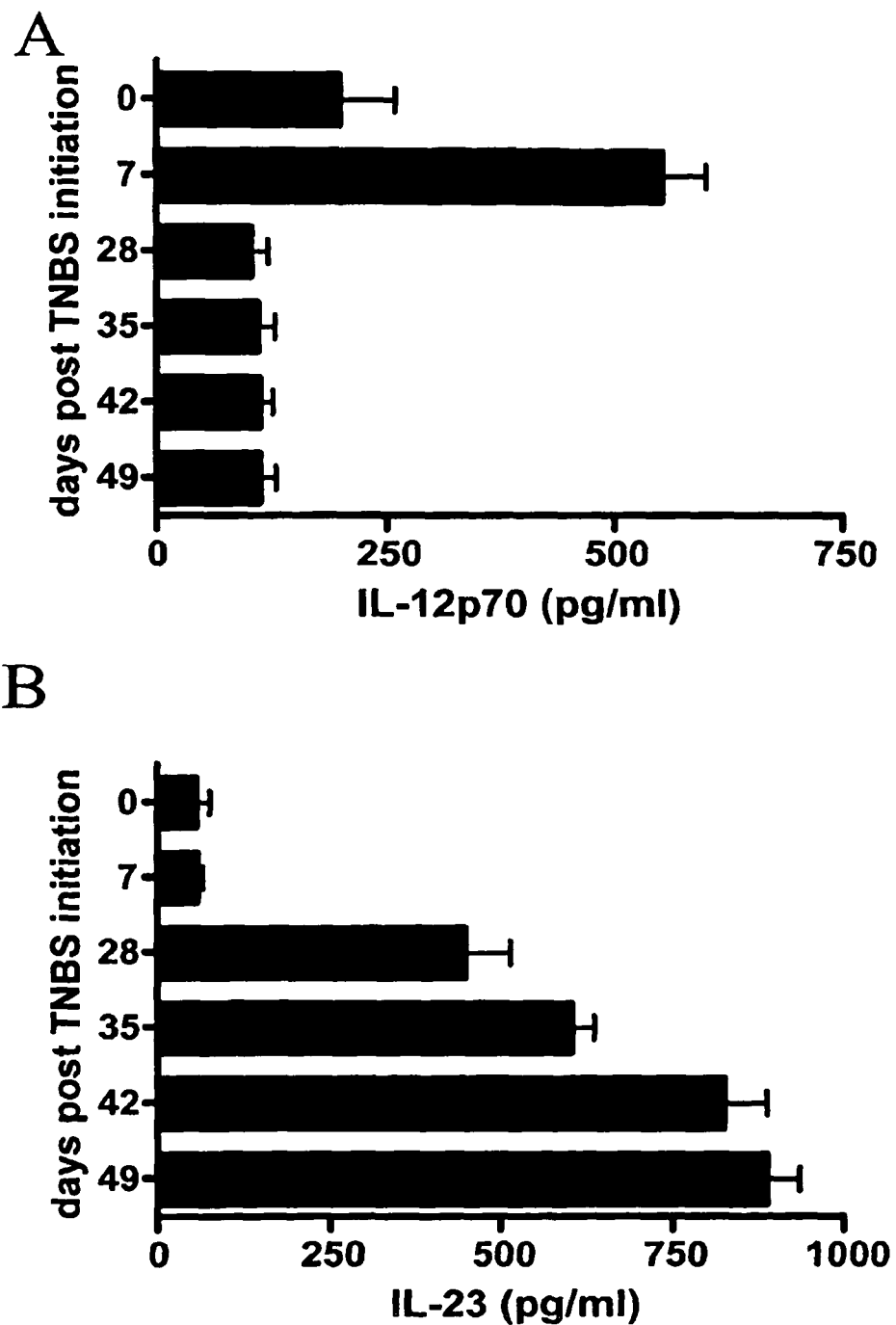
FIG. 10 shows cytokine measurement obtained on a weekly basis of colon tissue from Balb/c mice subjected to weekly TNBS administration. Initially, a Th1 mediated response is found (increased IL-12 and IFN-gamma). However, later in the disease process, increased amounts of IL-13 and TGF-beta are observed.
Figure 10:
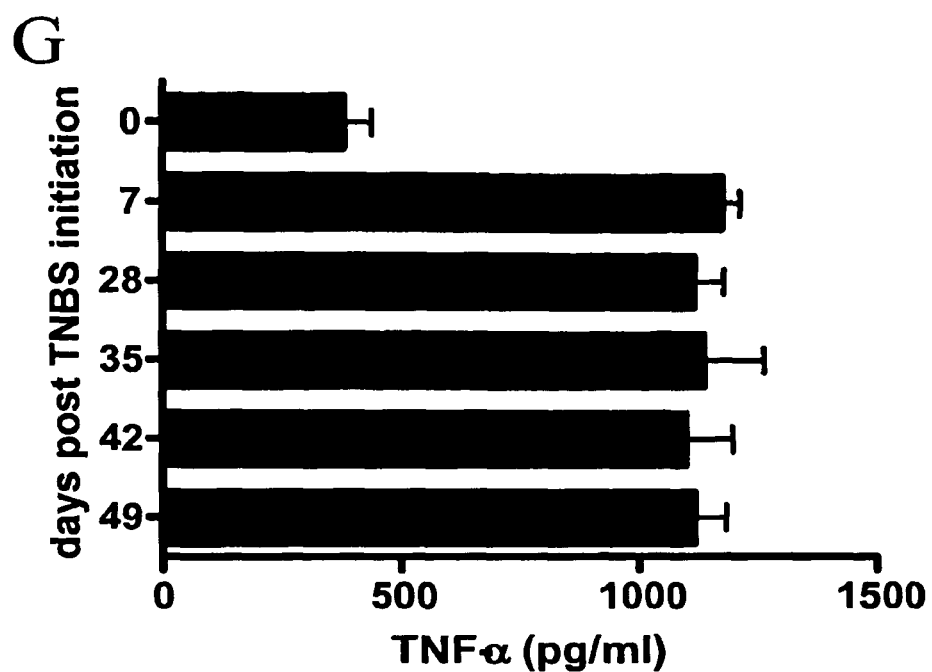

Early in the course of this colitis, cells from the lamina propria of the mice produce large amounts of IFN-γ, indicating the presence of a Th1 T cell-mediated inflammation similar to that in acute TNBS-colitis and CD (FIG. 10). However, at about 3-4 weeks after initiation of TNBS administration, the colonic cells begin to produce IL-23 and, concomitantly, begin to produce less IFN-γ and more IL-17 (FIG. 10). Then, 4-5 weeks after initiation of TNBS administration, the cells begin to produce IL-13 and, a week later, TGF-β (FIG. 10). At this point one begins to see the occurrence of fibrosis in the colonic lesions. Collagen formation, which is a good indicator of fibrosis, coincides with the occurrence of fibrosis (FIG. 9).

Figure 11:
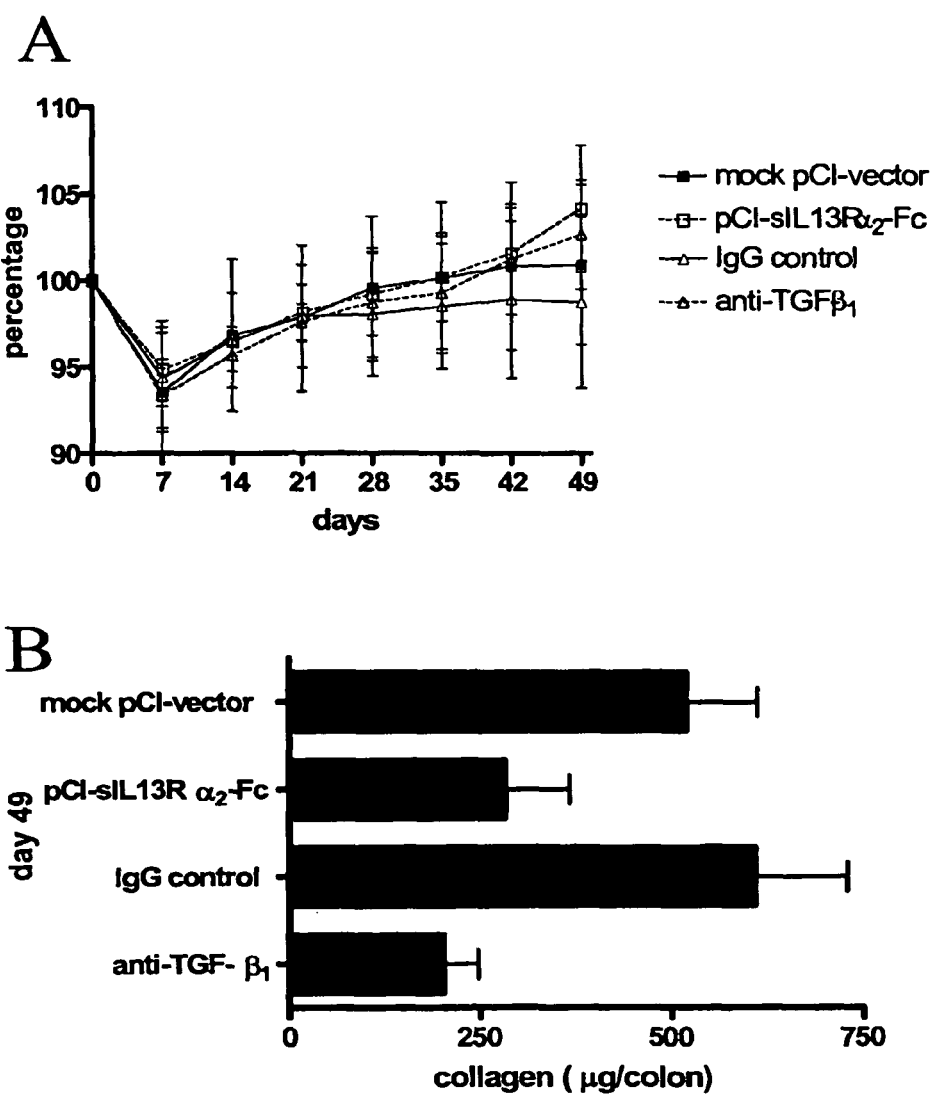
FIG. 11 shows mice with chronic TNBS-colitis that were treated (starting at 5 weeks in the time course of experiments) with either a plasmid that contains a blocking IL-13Rα2-Fc fusion protein or anti-TGF-β antibodies. Each treatment, but not control mock plasmid or control antibodies, leads to resolution of collagen formation and ensuing fibrosis.
Figure 12:
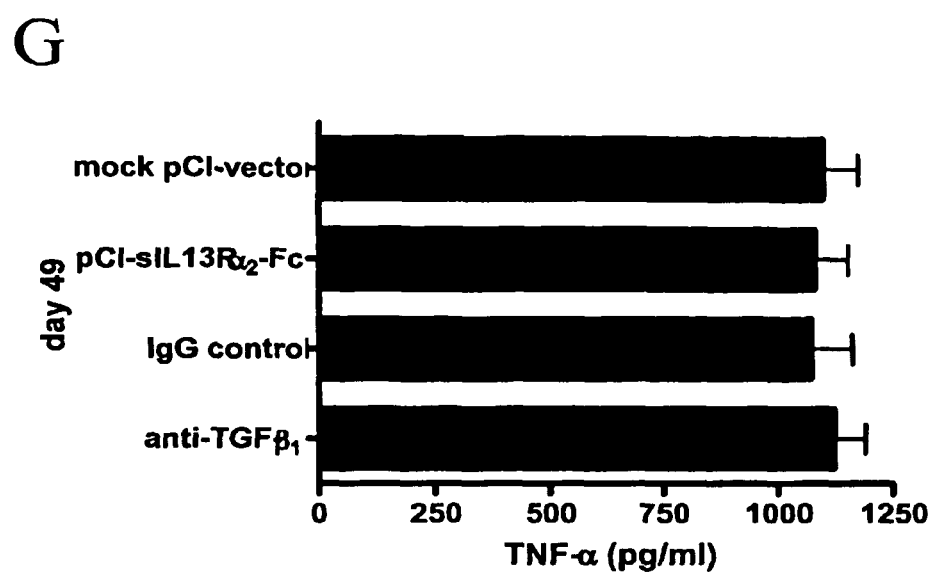
FIG. 12 shows cytokine measurement from mice treated with a plasmid containing IL-13Rα2-Fc fusion protein or anti-TGF-β. IL-13Rα2-Fc fusion protein leads to downmodulation of both IL-13 and TGF-beta while anti-TGF-β leads to downmodulation of TGF-β, but not IL-13.

However, if mice are administered IL-13Rα2-Fc, a substance that blocks the binding of IL-13 to its receptor, the mice do not produce TGF-β (FIG. 12) and do not develop fibrosis (FIG. 11).

Example 4

IL-13 Expression by Circulating T-cells (e.g., NKT Cells) Cells

Figure 13:
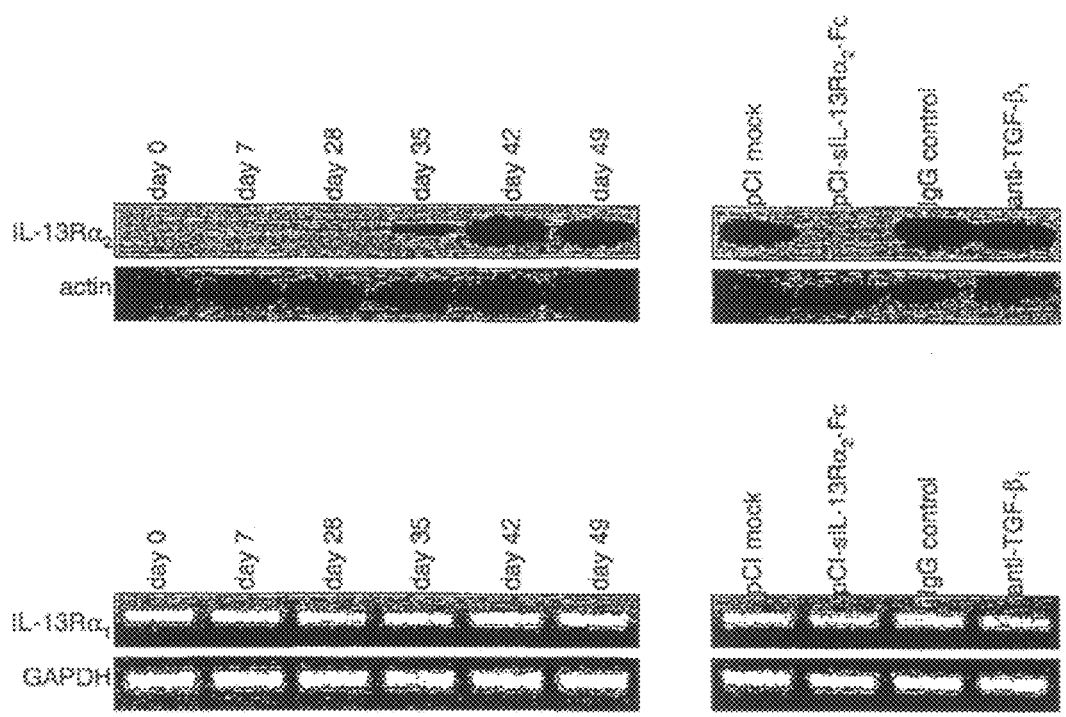
FIG. 13 demonstrates IL-13Rα2 and IL-13Rα1 expression in the chronic model of TNBS-colitis. Increased expression of IL-13Rα2 occurs in the latter stages of the disease process, whereas IL-13Rα1 is constitutively expressed.

As shown in FIG. 13, there is an increased expression of IL-13Rα2 in gut cells of mice in the latter stages of the disease process of chronic TNBS-colitis. In contrast, IL-13Rα1 is constitutively expressed in the gut of both control and diseased mice.

Analysis of peripheral blood monocuclear cells from ulcerative colitis and normal control subject population reveals that there are an increased number of NKT cells that express an IL-13 receptor (i.e., IL-13Rα2) in subjects with ulcerative colitis. Two channel flow cytometric analysis was used to identify cells bearing both NKT cell markers (e.g., CD161) and IL-13 receptors, using antibodies conjugated with appropriate fluorochromes. In subjects with ulcerative colitis, 1.29-6.88% cells were found to express this receptor whereas in controls 0.16-0.38% cells were found to express this receptor (FIG. 14).

Example 5

IL-13 Expression by T-cells (e.g., NKT Cells) Cells in Gut

An increase in the number of T-cells (e.g., NKT cells) that express an IL-13 receptor (e.g., IL-13Rα2) during inflammation in the gut during ulcerative colitis, acute Crohn's or chronic Crohn's disease is demonstrated by the following method. Gut cells isolated from control subjects or subjects with IBD are analyzed by two channel flow cytometric analysis using antibodies specific for T-cell markers (e.g., CD161 for NKT cells) and antibodies specific for IL-13 receptors (e.g., IL-13Rα2) to detect T-cells bearing an IL-13 receptor. Other methods known in the art for detecting co-expression of cell-surface proteins can also be used. By one or more of these methods is demonstrated that disease progression of IBD, e.g., ulcerative colitis, acute Crohn's or chronic Crohn's disease, involves an increase in the number of T-cells (e.g., NKT cells) expressing IL-13 receptor(s) in the affected gut. Further, as disclosed herein, this expression of IL-13 receptors by T-cells (e.g., NKT cells) is involved in inflammation and/or fibrosis in the gut during IBD, which can be inhibited by the compositions and methods provided herein.

Throughout this application, various publications are referenced. The disclosures of these publications in their entireties, as well as the references cited in these publications, are hereby incorporated by reference into this application in order to more fully describe the state of the art to which this invention pertains.

REFERENCES

Balk, S. P., Bleicher, P. A., and Terhorst, C. (1989). Isolation and characterization of a cDNA and gene coding for a fourth CD1 molecule. Proc Natl Acad Sci USA 86, 252-256.

Bendelac, A. (1995). Positive selection of mouse NK1+T cells by CD1-expressing cortical thymocytes. J Exp Med 182, 2091-2096.

Bleicher, P. A., Balk, S. P., Hagen, S. J., Blumberg, R. S., Flotte, T. J., and Terhorst, C. (1990). Expression of murine CD1 on gastrointestinal epithelium. Science 250, 679-682.

Blumberg, R. S., Terhorst, C., Bleicher, P., McDermott, F. V., Allan, C. H., Landau, S. B., Trier, J. S., and Balk, S. P. (1991). Expression of a nonpolymorphic MHC class I-like molecule, CD1D, by human intestinal epithelial cells. J Immunol 147, 2518-2524.

Boirivant, M., Fuss, I. J., Chu, A., and Strober, W. (1998). Oxazolone colitis: A murine model of T helper cell type 2 colitis treatable with antibodies to interleukin 4. J Exp Med 188, 1929-1939.

Brown, M. A., and Hural, J. (1997). Functions of IL-4 and control of its expression. Crit. Rev Immunol 17, 1-32.

Ceponis, P. J., Botelho, F., Richards, C. D., and McKay, D. M. (2000). Interleukins 4 and 13 increase intestinal epithelial permeability by a phosphatidylinositol 3-kinase pathway. Lack of evidence for STAT 6 involvement. J Biol Chem 275, 29132-29137.

Chen, H., and Paul, W. E. (1997). Cultured NK1.1+CD4+ T cells produce large amounts of IL-4 and IFN-gamma upon activation by anti-CD3 or CD1. J Immunol 159, 2240-2249.

Cui, J., Shin, T., Kawano, T., Sato, H., Kondo, E., Toura, I., Kaneko, Y., Koseki, H., Kanno, M., and Taniguchi, M. (1997). Requirement for Valpha14 NKT cells in IL-12-mediated rejection of tumors. Science 278, 1623-1626.

Donaldson, D. D., Whitters, M. J., Fitz, L. J., Neben, T. Y., Finnerty, H., Henderson, S. L., O'Hara, R. M., Jr., Beier, D. R., Turner, K. J., Wood, C. R., and Collins, M. (1998). The murine IL-13 receptor alpha 2: molecular cloning, characterization, and comparison with murine IL-13 receptor alpha 1. J Immunol 161, 2317-2324.

Fiorentino, D. F., Zlotnik, A., Vieira, P., Mosmann, T. R., Howard, M., Moore, K. W., and O'Garra, A. (1991). IL-10 acts on the antigen-presenting cell to inhibit cytokine production by Th1 cells. J Immunol 146, 3444-3451.

Fort, M. M., Cheung, J., Yen, D., Li, J., Zurawski, S. M., Lo, S., Menon, S., Clifford, T., Hunte, B., Lesley, R., et al. (2001). IL-25 induces IL-4, IL-5, and IL-13 and Th2-associated pathologies in vivo. Immunity 15, 985-995.

Fuss, I. J., Neurath, M., Boirivant, M., Klein, J. S., de la Motte, C., Strong, S. A., Fiocchi, C., and Strober, W. (1996). Disparate CD4+ lamina propria (LP) lymphokine secretion profiles in inflammatory bowel disease. Crohn's disease LP cells manifest increased secretion of IFN-gamma, whereas ulcerative colitis LP cells manifest increased secretion of IL-5. J Immunol 157, 1261-1270.

Gumperz, J. E., Roy, C., Makowska, A., Lum, D., Sugita, M., Podrebarac, T., Koezuka, Y., Porcelli, S. A., Cardell, S., Brenner, M. B., and Behar, S. M. (2000). Murine CD1d-restricted T cell recognition of cellular lipids. Immunity 12, 211-221.

Hayakawa, K., Lin, B. T., and Hardy, R. R. (1992). Murine thymic CD4+ T cell subsets: a subset (ThyO) that secretes diverse cytokines and overexpresses the V beta 8 T cell receptor gene family. J Exp Med 176, 269-274.

Ishikawa, H., Hisaeda, H., Taniguchi, M., Nakayama, T., Sakai, T., Maekawa, Y., Nakano, Y., Zhang, M., Zhang, T., Nishitani, M., et al. (2000). CD4(+) v(alpha)14 NKT cells play a crucial role in an early stage of protective immunity against infection with *Leishmania major*. Int Immunol 12, 1267-1274.

Kaneko, Y., Harada, M., Kawano, T., Yamashita, M., Shibata, Y., Gejyo, F., Nakayama, T., and Taniguchi, M. (2000). Augmentation of Valpha14 NKT cell-mediated cytotoxicity by interleukin 4 in an autocrine mechanism resulting in the development of concanavalin A-induced hepatitis. J Exp Med 191, 105-114.

Kawano, T., Cui, J., Koezuka, Y., Toura, I., Kaneko, Y., Motoki, K., Ueno, H., Nakagawa, R., Sato, H., Kondo, E., et al. (1997). CD1d-restricted and TCR-mediated activation of valpha14 NKT cells by glycosylceramides. Science 278, 1626-1629.

Koyasu, S. (1994). CD3+ CD16+NK1.1+B220+ large granular lymphocytes arise from both alpha-beta TCR+CD4− CD8− and gamma-delta TCR+CD4−CD8− cells. J Exp Med 179, 1957-1972.

Kumar, H., Belperron, A., garthold, S. W., and Bockenstedt, L. K. (2000). Cutting edge: CD1d deficiency impairs murine host defense against the spirochete, *Borrelia burgdorferi*. J Immunol 165, 4797-4801.

Lantz, O., and Bendelac, A. (1994). An invariant T cell receptor alpha chain is used by a unique subset of major histocompatibility complex class I-specific CD4+ and CD4-8− T cells in mice and humans. J Exp Med 180, 1097-1106.

Lee, P. T., Benlagha, K., Teyton, L., and Bendelac, A. (2002). Distinct functional lineages of human V(alpha)24 natural killer T cells. J Exp Med 195, 637-641.

Minty, A., Asselin, S., Bensussan, A., Shire, D., Vita, N., Vyakarnam, A., Wijdenes, J., Ferrara, P., and Caput, D. (1997). The related cytokines interleukin-13 and interleukin-4 are distinguished by differential production and differential effects on T lymphocytes. Eur Cytokine Netw 8, 203-213.

Madhankumar A B, Mintz A, Debinski W. Alanine-scanning mutagenesis of alpha-helix D segment of interleukin-13 reveals new functionally important residues of the cytokine. J Biol. Chem. 2002 Nov. 8; 277(45):43194-205.

Miyamoto, K., Miyake, S., and Yamamura, T. (2001). A synthetic glycolipid prevents autoimmune encephalomyelitis by inducing TH2 bias of natural killer T cells. Nature 413, 531-534.

Mizoguchi, A., Mizoguchi, E., and Bhan, A. K. (1999). The critical role of interleukin 4 but not interferon gamma in the pathogenesis of colitis in T-cell receptor alpha mutant mice. Gastroenterology 116, 320-326.

Moore, K. W., O'Garra, A., de Waal Malefyt, R., Vieira, P., and Mosmann, T. R. (1993). Interleukin-10. Annu Rev Immunol 11, 165-190.

Neurath, M. F., Fuss, I., Kelsall, B. L., Stuber, E., and Strober, W. (1995). Antibodies to interleukin 12 abrogate established experimental colitis in mice. J Exp Med 182, 1281-1290.

Oshima, Y., Puri, R. K. (2001) Characterization of a powerful high affinity antagonist that inhibits biological activities of human interleukin-13. J. Biol. Chem. 276: 15185-15191.

Oshima Y, Puri R K. A novel interleukin 13 (IL-13) antagonist that blocks the biological activity of human IL-13 in immune and nonimmune cells. FASEB J. 2001 June; 15(8):1469-71.

Oshima Y, Joshi B H, Puri R K. Conversion of interleukin-13 into a high affinity agonist by a single amino acid substitution. J Biol. Chem. 2000 May 12; 275(19):14375-80

Park, S. H., Roark, J. H., and Bendelac, A. (1998). Tissue-specific recognition of mouse CD1 molecules. J Immunol 160, 3128-3134.

Parronchi, P., Romagnani, P., Annunziato, F., Sampognaro, S., Becchio, A., Giannarini, L., Maggi, E., Pupilli, C., Tonelli, F., and Romagnani, S. (1997). Type 1 T-helper cell predominance and interleukin-12 expression in the gut of patients with Crohn's disease. Am J Pathol 150, 823-832.

Podolsky D K. Inflammatory bowel disease. N. Engl. J. Med. 2002; 347:417-429.

Puri, R. K., Leland, P. Obiri, N. l., Husain, S. R., Kreitman, R. J., Haas, G. P., Pastan, I., Debinski, W. (1996). Targeting of interleukin-13 receptor on human renal cell carcinoma cells by a recombinant chimeric protein composed of interleukin-13 and a truncated form of *Pseudomonas* exotoxin A (PE38QQR). Blood: 4333-4339.

Roark, J. H., Park, S. H., Jayawardena, J., Kavita, U., Shannon, M., and Bendelac, A. (1998). CD1.1 expression by mouse antigen-presenting cells and marginal zone B cells. J Immunol 160, 3121-3127.

Sartor, R. B. (1995). Current concepts of the etiology and pathogenesis of ulcerative colitis and Crohn's disease. Gastroenterol Clin North Am 24, 475-507.

Saubermann, L. J., Beck, P., De Jong, Y. P., Pitman, R. S., Ryan, M. S., Kim, H. S., Exley, M., Snapper, S., Balk, S. P., Hagen, S. J., et al. (2000). Activation of natural killer T cells by alpha-galactosylceramide in the presence of CD1d provides protection against colitis in mice. Gastroenterology 119, 119-128.

Scheiffele, F., Fuss, I. (2002). Induction of TNBS colitis in mice, Vol 15.19, John Wiley & Sons, Inc.).

Smiley, S. T., Kaplan, M. H., and Grusby, M. J. (1997). Immunoglobulin E production in the absence of interleukin-4-secreting CD1-dependent cells. Science 275, 977-979.

Sonoda, K. H., Exley, M., Snapper, S., Balk, S. P., and Stein-Streilein, J. (1999). CD1-reactive natural killer T cells are required for development of systemic tolerance through an immune-privileged site. J Exp Med 190, 1215-1226.

Spada, F. M., Koezuka, Y., and Porcelli, S. A. (1998). CD1d-restricted recognition of synthetic glycolipid antigens by human natural killer T cells. J Exp Med 188, 1529-1534.

Strober, S., Cheng, L., Zeng, D., Palathumpat, R., Dejbakhsh-Jones, S., Huie, P., and Sibley, R. (1996). Double negative (CD4−CD8− alpha beta+) T cells which promote tolerance induction and regulate autoimmunity. Immunol Rev 149, 217-230.

Strober W, Fuss I J, Blumberg R S. The immunology of mucosal models of inflammation. Annu. Rev. Immunol. 2002; 20:495-549.

Takeda, K., Hayakawa, Y., Van Kaer, L., Matsuda, H., Yagita, H., and Okumura, K. (2000). Critical contribution of liver natural killer T cells to a murine model of hepatitis. Proc Natl Acad Sci USA 97, 5498-5503.

Terabe, M., Matsui, S., Noben-Truath, N., Chen, H., Watson, C., Donaldson, D. D., Carbone, D. P., Paul, W. E., and Berzofsky, J. A. (2000). NKT cell-mediated repression of tumor immunosurveillance by IL-13 and the IL-4R-STAT6 pathway. Nat Immunol 1, 515-520.

Urban, S. F., Jr., Noben-Truth, N., Donaldson, D. D., Madden, K. B., Morris, S. C., Collins, M., and Finkelman, F. D. (1998). IL-13, IL-4Ralpha, and Stat6 are required for the expulsion of the gastrointestinal nematode parasite *Nippostrongylus brasiliensis*. Immunity 8, 255-264.

Vezys, V., Olson, S., and Lefrancois, L. (2000). Expression of intestine-specific antigen reveals novel pathways of CD8 T cell tolerance induction. Immunity 12, 505-514.

Wills-Karp, M., Luyimbazi, J., Xu, X., Schofield, B., Neben, T. Y., Karp, C. L., and Donaldson, D. D. (1998). Interleukin-13: central mediator of allergic asthma. Science 282, 2258-2261.

Yoshimoto, T., and Paul, W. E. (1994). CD4pos, NK1.1pos T cells promptly produce interleukin 4 in response to in vivo challenge with anti-CD3. J Exp Med 179, 1285-1295.

Zurawski, G., and de Vries, J. E. (1994). Interleukin 13, an interleukin 4-like cytokine that acts on monocytes and B cells, but not on T cells. Immunol Today 15, 19-26.

SEQUENCES (Human IL-13 protein [signal sequence (underlined) and mature])  SEQ ID NO: 1
MALLLTTVIALTCLGGFASPGPVPPSTALRELIEELVNITQNQKAPLCNGSWSINTAGMYCAALESLIN

VSGCSAIEKTQRMLSQFCPHKVSAGQFSSLHVRDTKIEVAQFVKDLLLHLKKLFREGRFN (Human IL-13 cDNA)  SEQ ID NO: 2
```
   1 ttcggcatcc gctcctcaat cctctcctgt tggcactggg cctcatggcg cttttgttga
  61 ccacggtcat tgctctcact tgccttggcg gctttgcctc cccaggccct gtgcctcct
 121 ctacagccct cagggagctc attgaggagc tggtcaacat cacccagaac cagaaggctc
 181 cgctctgcaa tggcagcatg gtatggagca tcaacctgac agctggcatg tactgtgcag
 241 ccctggaatc cctgatcaac gtgtcaggct gcagtgccat cgagaagacc cagaggatgc
 301 tgagcggatt ctgcccgcac aaggtctcag ctgggcagtt ttccagcttg catgtccgag
 361 acaccaaaat cgaggtggcc cagtttgtaa aggacctgct cttacattta aagaaacttt
 421 ttcgcgaggg acggttcaac tgaaacttcg aaagcatcat tatttgcaga gacaggacct
 481 gactattgaa gttgcagatt catttttctt tctgatgtca aaaatgtctt gggtaggcgg
 541 gaaggagggt tagggagggg taaaattcct tagcttagac ctcagcctgt gctgcccgtc
 601 ttcagcctag ccgacctcag ccttcccctt gccagggct cagcctggtg ggcctcctct
 661 gtccagggcc ctgagctcgg tggacccagg gatgacatgt ccctacaccc ctcccctgcc
 721 ctagagcaca ctgtagcatt acagtgggtg ccccccttgc cagacatgtg gtgggacagg
 781 gacccacttc acacacaggc aactgaggca gacagcagct caggcacact tcttcttggt
 841 cttatttatt attgtgtgtt atttaaatga gtgtgtttgt caccgttggg gattggggaa
 901 gactgtggct gctggcactt ggagccaagg gttcagagac tcagggcccc agcactaaag
 961 cagtggaccc caggagtccc tggtaataag tactgtgtac agaattctgc tacctcactg
1021 gggtcctggg gcctcggagc ctcatccgag gcagggtcag gagaggggca gaacagccgc
1081 tcctgtctgc cagccagcag ccagctctca gccaacgagt aatttattgt ttttcctcgt
1141 atttaaatat taaatatgtt agcaaagagt taatatatag aagggtacct tgaacactgg
1201 gggaggggac attgaacaag ttgtttcatt gactatcaaa ctgaagccag aaataaagtt
1261 ggtgacagat
```

(*Pseudomonas* exotoxin A (PE))  SEQ ID NO: 3
MHLIPHWIPLVASLGLLAGGSSASAAEEAFDLWNECAKACVLDLKDGVRSSRMSVDPAIADTNGQGVLHYSM

VLEGGNDALKLAIDNALSITSDGLTIRLEGGVEPNKPVRYSYTRQARGSWSLNWLVPIGHEKPSNIKVFIHE

LNAGNQLSHMSPIYTIEMGDELLAKLARDATFFVRAHESNEMQPTLAISHAGVSVVMAQTQPRREKRWSEWA

SGKVLCLLDPLDGVYNYLAQQRCNLDDTWEGKIYRVLAGNPAKHDLDIKPTVISHRLHFPEFFSLAALTAHQ

ACHLPLETFTRHTQPRGWEQLEQCGYPVQRLVALYLAARLSWNQVDQVIRNALASPGSGGDLGEAIREQPEQ

ARLALTLAAAESERFVRQGTGNDEAGAANADVVSLTCPVAAGECAGPADSGDALLERNYPTGAEFLGDGGDV

SFSTRGTQNWTVERLLQAHRQLEERGYVFVGYHGTFLEAAQSIVFGGVRARSQDLDAIWRGFYIAGDPALAY

| SEQUENCES | |
|---|---|
| GYAQDQEPDARGRIRNGALLRVYVPRSSLPGFYRTSLTLAAPEAAGEVERLIGHPLPLRLDAITGPEEEGGR<br>LETILGWPLAERTVVIPSAIPTDPRNVGGDLDPSSIPDKEQAISALPDYASQPGKPPREDLK | |
| KDEL | SEQ ID NO: 4 |
| REDLK | SEQ ID NO: 5 |
| REDL | SEQ ID NO: 6 |
| RDEL | SEQ ID NO: 7 |
| (Human IL-13 protein [mature])<br>SPGPVPPSTALRELIEELVNITQNQKAPLCNGSMVWSINLTAGMYCAALESLINVSGCSAIEKTQRMLSGFC<br>PHKVSAGQFSSLHVRDTKIEVAQFVKDLLLHLKKLFREGRFN | SEQ ID NO: 8 |

We claim:

1. A method of treating Crohn's disease (CD) or ulcerative colitis (UC) in inflammatory bowel disease in a subject comprising administering to the subject an effective amount of a substance that inhibits the binding of IL-13 to IL-13 receptors on NKT cells, wherein the substance comprises a modified IL-13, wherein the modified IL-13 comprises a mutation consisting of substituting a glutamic acid residue at position 13 of native human IL-13 (hIL-13) with a neutrally charged or positively charged amino acid residue, and wherein the modified IL-13 is linked to an effector molecule, wherein the effector molecule comprises a cytotoxin or radionuclide.

2. The method of claim 1, wherein the method reduces or eliminates the formation of fibrosis caused by CD or UC.

3. The method of claim 1, wherein the modified IL-13 binds the IL-13 receptors but has reduced capacity to activate signaling in said receptors.

4. The method of claim 3, wherein the modified IL-13 has a higher affinity for the IL-13 receptors than native human IL-13.

5. The method of claim 1, wherein the positively charged amino acid residue lysine or arginine.

6. The method of claim 1, wherein the modified IL-13 comprises the mutein hIL-13E13K of SEQ ID NO:8.

7. The method of claim 1, wherein the modified IL-13 linked to an effector molecule comprises a fusion protein.

8. The method of claim 7, wherein the effector molecule is conjugated to the modified IL-13.

9. The method of claim 7, wherein the cytotoxin is selected from a group consisting of *Pseudomonas* exotoxin or a cytotoxic subunit or mutant thereof comprising cytotoxic activity, Diptheria toxin or a cytotoxic subunit or mutant thereof comprising cytotoxic activity, ricin, saporin, gelonin, calicheamycin, doxorubicin, ribotoxin, ribosome in-activating protein, and abrin.

10. The method of claim 9, wherein the *Pseudomonas* exotoxin is selected from a group consisting of PE35, PE38, PE38 KDEL, PE40, PE4E, and PE38QQR.

* * * * *

```
                            SEQUENCE LISTING

<160> NUMBER OF SEQ ID NOS: 8

<210> SEQ ID NO 1
<211> LENGTH: 132
<212> TYPE: PRT
<213> ORGANISM: Homo sapiens

<400> SEQUENCE: 1

Met Ala Leu Leu Leu Thr Thr Val Ile Ala Leu Thr Cys Leu Gly Gly
 1               5                  10                  15

Phe Ala Ser Pro Gly Pro Val Pro Pro Ser Thr Ala Leu Arg Glu Leu
            20                  25                  30

Ile Glu Glu Leu Val Asn Ile Thr Gln Asn Gln Lys Ala Pro Leu Cys
        35                  40                  45

Asn Gly Ser Met Val Trp Ser Ile Asn Leu Thr Ala Gly Met Tyr Cys
    50                  55                  60

Ala Ala Leu Glu Ser Leu Ile Asn Val Ser Gly Cys Ser Ala Ile Glu
65                  70                  75                  80

Lys Thr Gln Arg Met Leu Ser Gly Phe Cys Pro His Lys Val Ser Ala
                85                  90                  95

Gly Gln Phe Ser Ser Leu His Val Arg Asp Thr Lys Ile Glu Val Ala
            100                 105                 110

Gln Phe Val Lys Asp Leu Leu Leu His Leu Lys Lys Leu Phe Arg Glu
        115                 120                 125

Gly Arg Phe Asn
    130

<210> SEQ ID NO 2
<211> LENGTH: 1270
<212> TYPE: DNA
<213> ORGANISM: Homo sapiens

<400> SEQUENCE: 2
ttcggcatcc gctcctcaat cctctcctgt tggcactggg cctcatggcg cttttgttga      60
ccacggtcat tgctctcact tgccttggcg gctttgcctc cccaggccct gtgcctcct     120 ctacagccct cagggagctc attgaggagc tggtcaacat cacccagaac cagaaggctc     180
cgctctgcaa tggcagcatg gtatggagca tcaacctgac agctggcatg tactgtgcag     240
ccctggaatc cctgatcaac gtgtcaggct gcagtgccat cgagaagacc cagaggatgc     300
tgagcggatt ctgcccgcac aaggtctcag ctgggcagtt ttccagcttg catgtccgag     360
```

| | | |
|---|---|---|
| acaccaaaat cgaggtggcc cagtttgtaa aggacctgct cttacattta aagaaacttt | 420 | |
| ttcgcgaggg acggttcaac tgaaacttcg aaagcatcat tatttgcaga gacaggacct | 480 | |
| gactattgaa gttgcagatt cattttctt tctgatgtca aaaatgtctt gggtaggcgg | 540 | |
| gaaggagggt tagggagggg taaaattcct tagcttagac ctcagcctgt gctgcccgtc | 600 | |
| ttcagcctag ccgacctcag ccttcccctt gcccagggct cagcctggtg ggcctcctct | 660 | |
| gtccagggcc ctgagctcgg tggacccagg gatgacatgt ccctacaccc ctcccctgcc | 720 | |
| ctagagcaca ctgtagcatt acagtgggtg ccccccttgc cagacatgtg gtgggacagg | 780 | |
| gacccacttc acacacaggc aactgaggca gacagcagct caggcacact tcttcttggt | 840 | |
| cttatttatt attgtgtgtt atttaaatga gtgtgtttgt caccgttggg gattggggaa | 900 | |
| gactgtggct gctggcactt ggagccaagg gttcagagac tcagggcccc agcactaaag | 960 | |
| cagtggaccc caggagtccc tggtaataag tactgtgtac agaattctgc tacctcactg | 1020 | |
| gggtcctggg gcctcggagc ctcatccgag gcagggtcag gagaggggca gaacagccgc | 1080 | |
| tcctgtctgc cagccagcag ccagctctca gccaacgagt aatttattgt ttttcctcgt | 1140 | |
| atttaaatat taatatgtt agcaaagagt taatatatag aagggtacct tgaacactgg | 1200 | |
| gggaggggac attgaacaag ttgtttcatt gactatcaaa ctgaagccag aaataaagtt | 1260 | |
| ggtgacagat | 1270 | |

<210> SEQ ID NO 3
<211> LENGTH: 638
<212> TYPE: PRT
<213> ORGANISM: Artificial Sequence
<220> FEATURE:
<223> OTHER INFORMATION: Description of Artificial Sequence: note = Synthetic Construct

<400> SEQUENCE: 3

```
Met His Leu Ile Pro His Trp Ile Pro Leu Val Ala Ser Leu Gly Leu
 1               5                  10                  15

Leu Ala Gly Gly Ser Ser Ala Ser Ala Ala Glu Glu Ala Phe Asp Leu
            20                  25                  30

Trp Asn Glu Cys Ala Lys Ala Cys Val Leu Asp Leu Lys Asp Gly Val
        35                  40                  45

Arg Ser Ser Arg Met Ser Val Asp Pro Ala Ile Ala Asp Thr Asn Gly
    50                  55                  60

Gln Gly Val Leu His Tyr Ser Met Val Leu Glu Gly Gly Asn Asp Ala
65                  70                  75                  80

Leu Lys Leu Ala Ile Asp Asn Ala Leu Ser Ile Thr Ser Asp Gly Leu
                85                  90                  95

Thr Ile Arg Leu Glu Gly Gly Val Glu Pro Asn Lys Pro Val Arg Tyr
            100                 105                 110

Ser Tyr Thr Arg Gln Ala Arg Gly Ser Trp Ser Leu Asn Trp Leu Val
        115                 120                 125

Pro Ile Gly His Glu Lys Pro Ser Asn Ile Lys Val Phe Ile His Glu
    130                 135                 140

Leu Asn Ala Gly Asn Gln Leu Ser His Met Ser Pro Ile Tyr Thr Ile
145                 150                 155                 160

Glu Met Gly Asp Glu Leu Leu Ala Lys Leu Ala Arg Asp Ala Thr Phe
                165                 170                 175

Phe Val Arg Ala His Glu Ser Asn Glu Met Gln Pro Thr Leu Ala Ile
            180                 185                 190
```

```
Ser His Ala Gly Val Ser Val Val Met Ala Gln Thr Gln Pro Arg Arg
        195                 200                 205

Glu Lys Arg Trp Ser Glu Trp Ala Ser Gly Lys Val Leu Cys Leu Leu
    210                 215                 220

Asp Pro Leu Asp Gly Val Tyr Asn Tyr Leu Ala Gln Gln Arg Cys Asn
225                 230                 235                 240

Leu Asp Asp Thr Trp Glu Gly Lys Ile Tyr Arg Val Leu Ala Gly Asn
                245                 250                 255

Pro Ala Lys His Asp Leu Asp Ile Lys Pro Thr Val Ile Ser His Arg
            260                 265                 270

Leu His Phe Pro Glu Gly Gly Ser Leu Ala Ala Leu Thr Ala His Gln
        275                 280                 285

Ala Cys His Leu Pro Leu Glu Thr Phe Thr Arg His Arg Gln Pro Arg
    290                 295                 300

Gly Trp Glu Gln Leu Glu Gln Cys Gly Tyr Pro Val Gln Arg Leu Val
305                 310                 315                 320

Ala Leu Tyr Leu Ala Ala Arg Leu Ser Trp Asn Gln Val Asp Gln Val
                325                 330                 335

Ile Arg Asn Ala Leu Ala Ser Pro Gly Ser Gly Gly Asp Leu Gly Glu
            340                 345                 350

Ala Ile Arg Glu Gln Pro Glu Gln Ala Arg Leu Ala Leu Thr Leu Ala
        355                 360                 365

Ala Ala Glu Ser Glu Arg Phe Val Arg Gln Gly Thr Gly Asn Asp Glu
    370                 375                 380

Ala Gly Ala Ala Asn Ala Asp Val Val Ser Leu Thr Cys Pro Val Ala
385                 390                 395                 400

Ala Gly Glu Cys Ala Gly Pro Ala Asp Ser Gly Asp Ala Leu Leu Glu
                405                 410                 415

Arg Asn Tyr Pro Thr Gly Ala Glu Phe Leu Gly Asp Gly Asp Val
            420                 425                 430

Ser Phe Ser Thr Arg Gly Thr Gln Asn Trp Thr Val Glu Arg Leu Leu
        435                 440                 445

Gln Ala His Arg Gln Leu Glu Glu Arg Gly Tyr Val Phe Val Gly Tyr
    450                 455                 460

His Gly Thr Phe Leu Glu Ala Ala Gln Ser Ile Val Phe Gly Gly Val
465                 470                 475                 480

Arg Ala Arg Ser Gln Asp Leu Asp Ala Ile Trp Arg Gly Phe Tyr Ile
                485                 490                 495

Ala Gly Asp Pro Ala Leu Ala Tyr Gly Tyr Ala Gln Asp Gln Glu Pro
            500                 505                 510

Asp Ala Arg Gly Arg Ile Arg Asn Gly Ala Leu Leu Arg Val Tyr Val
        515                 520                 525

Pro Arg Ser Ser Leu Pro Gly Phe Tyr Arg Thr Ser Leu Thr Leu Ala
    530                 535                 540

Ala Pro Glu Ala Ala Gly Glu Val Glu Arg Leu Ile Gly His Pro Leu
545                 550                 555                 560

Pro Leu Arg Leu Asp Ala Ile Thr Gly Pro Glu Glu Glu Gly Gly Arg
                565                 570                 575

Leu Glu Thr Ile Leu Gly Trp Pro Leu Ala Glu Arg Thr Val Val Ile
            580                 585                 590

Pro Ser Ala Ile Pro Thr Asp Pro Arg Asn Val Gly Gly Asp Leu Asp
        595                 600                 605
```

```
Pro Ser Ser Ile Pro Asp Lys Glu Gln Ala Ile Ser Ala Leu Pro Asp
    610                 615                 620

Tyr Ala Ser Gln Pro Gly Lys Pro Pro Arg Glu Asp Leu Lys
625                 630                 635

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 4

Lys Asp Glu Leu
  1

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 5

Arg Glu Asp Leu Lys
  1               5

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 6

Arg Glu Asp Leu
  1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: note =
      Synthetic Construct

<400> SEQUENCE: 7

Arg Asp Glu Leu
  1

<210> SEQ ID NO 8
<211> LENGTH: 114
<212> TYPE: PRT
<213> ORGANISM: Homo sapiens

<400> SEQUENCE: 8

Ser Pro Gly Pro Val Pro Pro Ser Thr Ala Leu Arg Glu Leu Ile Glu
  1               5                  10                  15

Glu Leu Val Asn Ile Thr Gln Asn Gln Lys Ala Pro Leu Cys Asn Gly
                 20                  25                  30

Ser Met Val Trp Ser Ile Asn Leu Thr Ala Gly Met Tyr Cys Ala Ala
             35                  40                  45
```

-continued

```
Leu Glu Ser Leu Ile Asn Val Ser Gly Cys Ser Ala Ile Glu Lys Thr
    50                  55                  60

Gln Arg Met Leu Ser Gly Phe Cys Pro His Lys Val Ser Ala Gly Gln
65              70                  75                      80

Phe Ser Ser Leu His Val Arg Asp Thr Lys Ile Glu Val Ala Gln Phe
                85                  90                  95

Val Lys Asp Leu Leu Leu His Leu Lys Lys Leu Phe Arg Glu Gly Arg
            100                 105                 110

Phe Asn
```